United States Patent
Grunden et al.

(10) Patent No.: US 10,526,615 B2
(45) Date of Patent: Jan. 7, 2020

(54) TRANSGENIC EXPRESSION OF ARCHAEA SUPEROXIDE REDUCTASE

(71) Applicant: North Carolina State University, Raleigh, NC (US)

(72) Inventors: Amy Michele Grunden, Holly Springs, NC (US); Heike Sederoff, Raleigh, NC (US); Roopa D. Yalamanchili, Cary, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 15/836,465

(22) Filed: Dec. 8, 2017

(65) Prior Publication Data

US 2018/0371489 A1 Dec. 27, 2018

Related U.S. Application Data

(63) Continuation of application No. 14/900,775, filed as application No. PCT/US2014/043393 on Jun. 20, 2014.

(60) Provisional application No. 61/838,817, filed on Jun. 24, 2013.

(51) Int. Cl.
 *C12N 15/82* (2006.01)
 *C12N 9/02* (2006.01)

(52) U.S. Cl.
 CPC ....... *C12N 15/8279* (2013.01); *C12N 9/0089* (2013.01); *C12N 15/8282* (2013.01)

(58) Field of Classification Search
 None
 See application file for complete search history.

(56) References Cited

U.S. PATENT DOCUMENTS

| | | |
|---|---|---|
| 5,689,040 A | 11/1997 | Harada et al. |
| 7,208,318 B2 | 4/2007 | Hain et al. |
| 7,301,070 B2 | 11/2007 | Dehesh |
| 2011/0207189 A1 | 8/2011 | Burgard et al. |
| 2011/0268865 A1 | 11/2011 | Kebeish et al. |
| 2012/0064622 A1 | 3/2012 | Fischer et al. |
| 2012/0145950 A1 | 6/2012 | Mahulikar et al. |
| 2014/0150135 A1 | 5/2014 | Grunden et al. |

FOREIGN PATENT DOCUMENTS

| | | |
|---|---|---|
| WO | WO 2009/037279 A1 | 3/2009 |
| WO | WO 2009/079529 A2 | 6/2009 |
| WO | WO 2011/021190 A1 * | 2/2011 |
| WO | WO 2011/095528 A1 | 8/2011 |
| WO | WO 2014/085261 A1 | 6/2014 |

OTHER PUBLICATIONS

Pyrococcus furiosus superoxide reductase DSM 3638, GenBank accession No. AAL81405, published Feb. 24, 2009.*
Pinto et al., 2010, Biochimica et Biophysica Acta 1804: 285-297.*
Sankaran et al., 2010, Computers and Electronics in Agriculture 72: 1-13.*
Millar et al., 2006, Current Opinion in Plant Biology 9: 610-615.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Im et al., 2009, Plant Physiology 151: 893-904.*
Ji, 2007, PhD Thesis, North Carolina State University, pp. 1-218.*
Glaser and Soll, 2004, In: Molecular Biology and Biotechnology of Plant Organelles, H. Daniell and C. Chase, eds., pp. 385-417.*
Aoshima et al. "A novel oxalosuccinate-forming enzyme involved in the reductive carboxylation of 2-oxoglutarate in *Hydrogenobacter thermophilus* TK-6", *Mol Microbiol* 62:748-59 (2006).
Bai et al. Plasmid construction for genetic modification of dicotyledonous plants with glycolate oxidizing pathway. *Genet. Mol. Res.* 10(3):1356-1363 (2011).
Bar-Even et al. "Design and analysis of synthetic carbon fixation pathways" *Proc Natl Acad Sci* USA 107:8889-94 (2010).
Bate et al., "An Invertase Inhibitor from Maize Localizes to the Embryo surrounding Region during Early Kernel Development", *Plant Physiology* 134 (1): 246-254 (2004).
Buchanan et al. "A reverse KREBS cycle in photosynthesis: consensus at last" *Photosynth Res*, 1990. 24: p. 47-53.
Buck at al, "Cloning and expression of the succinyl-CoA synthetase genes of *Escherichia coli* K12", J Gen Microbiol, 132, 1753-62. (1986).
Cheng et al. "The Miniature1 seed locus of maize encodes a cell wall invertase required for normal development of endosperm and maternal cells in the pedicel", *Plant Cell*, 8(6):971-983 (1996).
Flexas et al., "Tobacco aquaporin NtAQP1 is involved in mesophyll conductance to CO2 in vivo" *Plant J*, 2006. 48(3): p. 427-39.
Fridman et al. "Zooming in on a quantitative trait for tomato yield using interspecific introgressions" *Science* 305(5691):1786-1789 (2004).

(Continued)

*Primary Examiner* — Bratislav Stankovic
(74) *Attorney, Agent, or Firm* — Myers Bigel, P.A.

(57) ABSTRACT

This invention provides a stably transformed plant, plant part and/or plant cell, comprising a heterologous polynucleotide encoding a superoxide reductase (SOR) from an archaeon species, wherein said stably transformed plant, plant cell, and/or plant part has increased disease resistance. The invention further provides a method of increasing disease resistance in a plant, plant cell, or plant part, comprising: introducing into said plant, plant cell, or plant part a heterologous polynucleotide encoding a superoxide reductase from an archaeon species to produce a stably transformed plant, plant cell, or plant part, thereby producing a plant, plant part, or plant cell having increased disease resistance as compared to a control. Additionally provided are plants, plant parts, and plant cells produced by the methods of the invention, as well as progeny and products produced therefrom.

2 Claims, 3 Drawing Sheets
Specification includes a Sequence Listing.

(56) References Cited

OTHER PUBLICATIONS

GenBank® Database Accession No. AAG19513.1, putative 2-ketoglutarate ferredoxin oxidoreductase [*Halobacterium* sp. NRC-1], Jan. 31, 2014, 2 pages.
GenBank® Database Accession No. AAG19514.1, putative 2-ketoglutarate ferredoxin oxidoreductase [*Halobacterium* sp. NRC 1], Jan. 31, 2014, 2 pages.
GenBank® Database Accession No. AB076021.1, "Chlorobium limicola Cl-idh gene for isocitrate dehydrogenase, complete cds", Jun. 13, 2002, 2 pages.
GenBank® Database Accession No. ACICU_02687 isocitrate dehydrogenase [Acinetobacter baumannii ACICU], Updated Apr. 12, 2014; 4 pages.
GenBank® Database Accession No. AGSL01000085.1, "Pseudomonas stutzeri ATCC 14405 = CCUG 16156 contig00098, whole genome shotgun sequence" (Region from base 52,360-53,765), Mar. 5, 2012, 2 pages.
GenBank® Database Accession No. AGSL01000085.1, "Pseudomonas stutzeri ATCC 14405 = CCUG 16156 contig00098, whole genome shotgun sequence" (Region from base 50,522-52,339), Mar. 5, 2012, 2 pages.
GenBank® Database Accession No. BAC00856.1 isocitrate dehydrogenase [Chlorobium limicola], Jun. 13, 2002, 1 page.
GenBank® Database Accession No. EHY78620.1, "pyruvate carboxylase subunit B [Pseudomonas stutzeri ATCC 14405 = CCUG 16156]", Mar. 5, 2012, 2 pages.
GenBank® Database Accession No. EHY78621.1, "pyruvate carboxylase subunit A [Pseudomonas stutzeri ATCC 14405 = CCUG 16156]", Mar. 5, 2012, 1 page.
GenBank® Database Accession No. Kole_1227 isocitrate dehydrogenase (NADP(+)) [Kosmotoga olearia TBF 19,5.1], Updated Apr. 12, 2014, 2 pages.
GenBank® Database Accession No. Mmc1_1749 pyruvate flavodoxin/ferredoxin oxidoreductase domain-containing protein [Magnetococcus marinus MC-1], Updated Apr. 12, 2014 2 pages.
GenBank® Database Accession No. Mmc1_1750 pyruvate ferredoxin/flavodoxin oxidoreductase subunit beta [Magnetococcus marinus MC-1], Updated Apr. 12, 2014, 2 pages.
GenBank® Database Accession No. NC_000913.2, "*Escherichia coli* str. K-12 substr. MG1655, complete gpnome", (Region from base 763,403-772,237), Jul. 22, 2013, 7 pages.
GenBank® Database Accession No. NC_000913.2, "*Escherichia coil* str. K-12 substr. MG1655, complete genome", (Region from base 763,403-764,272), Jul. 22, 2013, 3 pages.
GenBank® Database Accession No. NC_002607.1, "*Halobacterium* sp. NRC-1 chromosome, complete genome", (Region from base 856,660-858,582), Jun. 27, 2013, 2 pages.
GenBank® Database Accession No. NC_002607.1, "*Halobacterium* sp. NRC-1 chromosome, complete genome", (Region from base 855,719-856,657), Jun. 27, 2013, 2 pages.
GenBank® Database Accession No. NC_003450.3, "Corynebacterium glutarnicum ATCC 13032, complete genome", (Region from base 2,470,741-2,472,039), Mar. 19, 2014, 2 pages.
GenBank® Database Accession No. NC_006361.1. "Nocardia farcinica IFM 10152 chromosome, complete genome", (Region from base 5,525,226-5,526,515), Jun. 10, 2013, 2 pages.
GenBank® Database Accession No. NC_008268.1, "Rhodococcus jostii RHA1 chromosome, complete genome", (Region from base 2,230,309-2,231,598), Jun. 10, 2013, 2 pages.
GenBank® Database Accession No. NC_008576.1, "Magnetococcus marinus MC-1 chromosome, complete genome", Jun. 10, 2013, 2 pages.
GenBank® Database Accession No. NC_009485.1, "*Bradyrhizobium* sp. BTAi1 chromosome, complete genome", (Region from base 393,292-394,488), Jun. 10, 2013, 2 pages.
GenBank® Database Accession No. NC_009485.1, "*Bradyrhizobium* sp. BTAi1 chromosome, complete genome", (Region from base 394,545-395,429), Jun. 10, 2013, 2 pages GenBank® Database Accession No. NC_010611.1, "Acinetobacter baumannii ACICU chromosome, complete genome", Jun. 10, 2013, 1 page.
GenBank® Database Accession No. NC_012560.1, "Azotobacter vinelandii DJ chromosome, complete genome", (Region from base 3,074,152-3,075,321), Jun. 10, 2013, 2 pages.
GenBank® Database Accession No. NC_012560.1, "Azotobacter vinelandii DJ chromosome, complete genome", (Region from base 3,073,268-3,074,155), Jun. 10, 2013, 2 pages.
GenBank® Database Accession No. NC_012785.1, "Kosmotoga olearia TBF 19.5.1, complete genome", Jun. 10, 2013, 2 pages.
GenBank® Database Accession No. NC_013799.1, "Hydrogenobacter thermophilus TK-6, complete genome", (Region from base 997,525-999,348), Jun. 10, 2013, 2 pages.
GenBank® Database Accession No. NC_013799.1, "Hydrogenobacter thermophilus TK-6, complete genome", (Region from base 996,624-997,511), Jun. 10, 2013, 2 pages.
GenBank® Database Accession No. NC_013799.1, "Hydrogenobacter thermophilus TK-6, complete genome", (Region from base 1,271,487-1,273,445), Jun. 10, 2013, 2 pages.
GenBank® Database Accession No. NC_013799.1, "Sydrogenobacter thermophilus TK-6, complete genome", (Region from base 1,273,469-1,274,887), Jun. 10, 2013, 2 pages.
GenBank® Database Accession No. NC_013854.1, "*Azospirillum* sp. B510 chromosome, complete genome", (Region from base 2,941,010-2,942,206), Jun. 10, 2013, 2 pages.
GenBank® Database Accession No. NC_013854.1, "*Azospirillum* sp. B510 chromosome, complete genome", (Region from base 2,942,208-2,943,083) Jun. 10, 2013, 2 pages.
GenBank® Database Accession No. NC_013960.1, "Nitrosococcus halophilus Nc4 chromosome, complete genome", (Region from base 2,610,547-2,611,815), Jun. 10, 2013, 2 pages.
GenBank® Database Accession No. NC_014355.1, "Candidatus Nitrospira defluvii, complete genome", (Region from base 1,174,721-1,176,652) Aug. 27, 2013, 2 pages.
GenBank® Database Accession No. NC_014355.1, "Candidatus Nitrospira defluvii, complete genome", (Region from base 1,176,781-1,178,199), Aug. 27, 2013, 2 pages.
GenBank® Database Accession No. Nhal_2539 isocitrate dehydrogenase, NADP-dependent [Nitrosococcus halophilus Nc 4], Updated Apr. 12, 2014, 4 pages.
GenBank® Database Accession No. NP_280033.1, 2-ketoglutarate ferredoxin oxidoreductase [*Halobacterium* sp. NRC-1], Jun. 27, 2013, 2 pages.
GenBank® Database Accession No. NP_280034.1, 2-ketogluterate ferredoxin oxidoreductase [*Halobacterium* sp. NRC-1], Jun. 27, 2013, 2 pages.
GenBank® Database Accession No. NP_415256.1, "succinyl-CoA synthetase, beta subunit [*Escherichia coli* str. K-12 substr. MG1655]", Mar. 19, 2014, 2 pages.
GenBank® Database Accession No. NP_415257.1, succinyl-coA synthetase, NAD(P)-binding, alpha subunit [*Escherichia coli* str. K-12 substr. MG1655], Mar. 19, 2014, 2 pages.
GenBank® Database Accession No. NP_601531.1 isocitrate lyase [Corynebacterium glutamicum ATCC 13032], 2 pages.
GenBank® Database Accession No. NZ_AAVV01000002.1, "Marine gamma proteobacterium HTCC2080 1100755000543, whole genome shotgun sequence", (Region from base 123,681-124,934), Dec. 15, 2006, 2 pages.
GenBank® Database Accession No. NZ_ACPC01000013.1, "*Bacillus* sp. M3-13 NZ_ACPC01000013, whole genome shotgun sequence", (Region from base 932-2,668 and 65-931), May 12, 2013, 25 pages.
GenBank® Database Accession No. NZ_ADZY02000226.1, "*Paenibacillus larvae* subsp *larvae* B-3650 contig_4241.0, whole genome shotgun sequence", (Region from base 7939-9687 and 7085-7951), Nov. 15, 2011, 28 pages.
GenBank® Database Accession No. NZ_AEMG01000009.1, "Haladaptatus paucihalophilus DX253 contig00009, whole genome shotgun sequence" (Region from base 157,678-159,432 and 156,818-157,681), May 9, 2013, 100 pages.
GenBank® Database Accession No. NZ_AGFC01000013.1, "Thiocystis violascens DSM 198 ctg263, whole genome shotgun sequence", (Region from base 61,879-63,297 and 83,889-65,718) Oct. 11, 2011, 23 pages.

(56) References Cited

OTHER PUBLICATIONS

GenBank® Database Accession No. NZ_AHBW01000053.1, "Rhodococcus pyridinivorans AK37 contig53, whole genome shotgun sequence", (Region from base 20,169-21,458), Dec. 8, 2011, 2 pages.

GenBank® Database Accession No. NZ_BACI01000050.1, "Gordonia alkanivorans NBRC, 16433 DNA, contig. GOALK050, whole genome shotgun sequence", (Region from base 37,665-38,960), May 8, 2013, 2 pages.

GenBank® Database Accession No. RHA1_ro02122 isocitrate lyase [Rhodococcus jostii RHA1], Updated Apr. 12, 2014, 3 pages.

GenBank® Database Accession No. YP_001236586.1, "succinyl-CoA synthetase subunit beta [*Bradyrhizobium* sp. BTAi1]", Jun. 10, 2013, 2 pages.

GenBank® Database Accession No. YP_001236587.1, "succinyl-CoA synthetase subunit alpha [*Bradyrhizobium* sp. BTAi1]", Jun. 10, 2013, 2 pages.

GenBank® Database Accession No. YP_001847346.1, "isocitrate dehydrogenase [Acinetobacter baumannii ACICU]", Jun. 10, 2013, 2 pages.

GenBank® Database Accession No. YP_002800114.1, succinyl-CoA ligase subunit alpha [Azotobacter vinelandii DJ], Jun. 10, 2013, 2 pages.

GenBank® Database Accession No. YP_002800115.1, succinyl-CoA synthetase subunit beta [Azotobacter vinelandii DJ], Jun. 10, 2013, 2 pages.

GenBank® Database Accession No. YP_002940928.1 "Isocitrate dehydrogenase (NADP [Kosmotoga olearia TBF 19.5.1]", Jun. 10, 2013, 2 pages.

GenBank® Database Accession No. YP_003432751.1, "2-oxoglutarate:ferredoxin oxidoreductase beta subunit [Hydrogenobacter thermophilus TK-6]", Jun. 10, 2013, 2 pages.

GenBank® Database Accession No. YP_003432752.1, "2-oxoglutarate:ferredoxin oxidoreductase alpha subunit [Hydrogenobacter thermophilus TK-6]", Jun. 10, 2013, 2 pages.

GenBank® Database Accession No. YP_003433044.1, 2-oxoglutarate carboxylase large subunit [Hydrogenobacter therrnephilus TK-6], Jun. 10, 2013, 2 pages.

GenBank® Database Accession No. YP_003433045.1, "2-oxoglutarate carboxylase small subunit [Hydrogenobacter thermophilus TK-6]", Jun. 10, 2013, 2 pages.

GenBank® Database Accession No. YP_003449758.1, "succinyl-CoA synthetase subunit beta [*Azospirillum* sp. B510]", Jun. 10. 2013, 2 pages.

GenBank® Database Accession No. YP_003449759.1, "succinyl-CoA synthetase subunit alpha [*Azospinilum* sp. B510]", Jun. 10, 2013, 2 pages.

GenBank® Database Accession No. YP_003528006.1, "isocitrate dehydrogenase, NADP-dependent [Nitrosococcus halophilus Nc 4]", Jun. 10, 2013, 2 pages.

GenBank® Database Accession No. YP_003796887.1, "pyruvate carboxylase subunit B [Candidatus Nitrospira defluvii]", Aug. 27, 2013, 2 pages.

GenBank® Database Accession No. YP_003796888.1, pyruvate carboxylase subunit A [Candidatus Nitrospira defluvii], Aug. 27, 2013, 2 pages.

GenBank® Database Accession No. YP_121446.1, isocitrate lyase [Nocardia farcinica IFM 10152], Jun. 10, 2013, 2 pages GenBank® Database Accession No. YP_702087.1, isocitrate lyase [Rhodococcus jostii RHA1], Jun. 10, 2013, 2 pages.

GenBank® Database Accession No. YP_865663.1, "pyruvate flavodoxin/ferredoxin oxidoreductase domain-containing protein [Magnetococcus marinus MC-1]", Jun. 10, 2013, 2 pages.

GenBank® Database Accession No. YP_865664.1, "pyruvate ferredoxin/flavodoxin oxidoreductase subunit beta [Magnetococcus marinus MC-1", Jun. 10, 2013, 2 pages.

GenBank® Database Accession No. ZP_01452577.1, acetyl-CoA carboxylase, biotin carboxylase [Mariprofundus ferrooxydans PV-1], Nov. 26, 2012, 1 page.

GenBank® Database Accession No. ZP_01452578.1, oxaloacetate decarboxylase [Mariprofundus ferrooxydans PV-1], Nov. 26, 2012, 1 page.

GenBank® Database Accession No. ZP_01625318.1, "Isocitrate dehydrogenase NADP-dependent [marine gamma proteobacterium HCC2080]", Nov. 9, 2010, 2 pages.

GenBank® Database Accession No. ZP_07708141.1, 2-oxoglutarate ferredoxin oxidoreductase subunit beta [*Bacillus* sp. M3-13], Dec. 9, 2010, 1 page.

GenBank® Database Accession No. ZP_07708142.1, "2-oxoglutarate ferredoxin oxidoreductase, alpha subunit [*Bacillus* sp. M3-13]", Dec. 9, 2010, 1 page.

GenBank® Database Accession No. ZP_08044529.1, 2-oxoglutarate ferredoxin oxidoreductase subunit beta [Haladaptatus paucihalophilus DX253], Feb. 7, 2011, 1 page.

GenBank® Database Accession No. ZP_08044530.1, pyruvate flavodoxin/ferredoxin oxidoreductase domain protein [Haladaptatus paucihalohilus DX253], Feb. 7, 2011, 1 page.

GenBank® Database Accession No. ZP_08765259.1, "isocitrate lyase [Gordonia alkanivorans NBRC 16433", Feb. 19, 2012, 1 page.

GenBank® Database Accession No. ZP_08925050.1, acetyl-CoA carboxylase, biotin carboxylase [Thiocystis violascens DSM 198], Oct. 11, 2011, 1 page.

GenBank® Database Accession No. ZP_08925052.1, oxaloacetate decarboxylase alpha subunit [Thiocystis violascens DSM 198]. Oct. 11, 2011, 1 page.

GenBank® Database Accession No. ZP_09070119.1, 2-oxoglutarate ferredoxin oxidoreductase subunit beta [*Paenibacillus larvae* subsp. *Larvae* B-3650], Nov. 15, 2011, 1 page.

GenBank® Database Accession No. ZP_09070120.1, hypothetical protein PlarlB_12680 [*Paenibacillus larvae* subsp. *larvae* B-3650], Nov. 15, 2011, 1 page.

GenBank® Database Accession No. ZP_09310682.1, "isocitrate lyase [Rhodococcus pyridinivorans AK37]", Dec. 15, 2011, 2 pages.

GenBank® Database Accession No. NZ_AATS01000007.1, "Mariprofundus ferrooxydans PV-1 109921033908, whole genome shotgun sequence", (Region from base 81,967-83,385 and 83,475-85;328) Sep. 15, 2006, 57 pages.

Gotto et al. (1961) The metabolism of $C_2$ compounds in microorganisms. 7. Preparation and properties of crystalline tartronic semialdehyde reductase. *Biochem J*. 81:273-281.

Greiner et al. "Cloning of a tobacco apoplasmic invertase inhibitor. Proof of function of the recombinant protein and expression analysis during plant development" *Plant Physiol*, 1998. 116(2). p. 733-42.

Greiner et al. "Ectopic expression of a tobacco invertase inhibitor homolog prevents cold-induced sweetening of potato tubers" *Nat Biotechnol*. 17(7):708-11 (1999).

Greiner et al, "Plant invertase inhibitors: expression in cell culture and during plant deveopment", *Australian Journal of Plant Physiology* 27(9): 807-814 (2000).

Hausler, et al. "Overexpression of C(4)-cycle enzymes in transgenic C(3) plants: a biotechnological approach to improve C(3)-photosynthesis" J Exp Bot, 2002. 53(369): p. 591-607.

Hothorn et al. "Structural insights into the pH-controlled targeting of plant cell-wall invertase by as specific inhibitor protein", *Proc Natl Acad Sci U S A*. 107(40):17427-32 (2010).

Hothorn et al. Structural Insights into the Target Specificity of Plant Invertase and Pectin Methylesterase Inhibitory Proteins, *Plant Cell* 16 (12): 3437-3447(2004).

Im et al. "Expression of Pyrococcus furiosus superoxide reductase in *Arabidopsis* enhances heat tolerance" Plant Physiol, 2009. 151(2): p. 893-9.

Im et al. "Production of a thermostable archaeal superoxide reductase in plant cells" FEBS Lett, 2005. 579(25): p. 5521-6

International Preliminary Report on Patentability Corresponding to International Application No. PCT/US2014/043407; dated Jan. 7, 2016.

International Preliminary Report on Patentability corresponding to International Application No. PCT/US2014/043393; dated Jan. 7, 2015.

(56) References Cited

OTHER PUBLICATIONS

International Search Report and Written Opinion Corresponding to international Application No. PCT/US2013/071515; dated Apr. 24, 2014; 8 pages.
Jin et al. "Posttranslational elevation of cell wall invertase activity by silencing its inhibitor in tomato delays leaf senescence and increases seed weight and fruit hexose level" *Plant Cell*. 21(7):2072-89 (2009).
Kebeish et al. "Choloroplastic photorespiratory bypass increases photosynthesis and biomass production in *Arabidopsis thaliana*", *Nat Biotechnol*, 2007. 25(5): p. 593-9.
Kerscher et al. "Purification and properties of two 2-oxoacid:ferredoxin oxidoreductases from Halobacterium halobium", *Eur J Biochem*, 1981. 116(3): 587-94.
Knutzon et al. (1999) Lysophosphatidic Acid Acyltransferase from Coconut Endosperm Mediates the Insertion of Laurate at the sn-2 Position of Triacylglycerols in Lauric Rapeseed Oil and Can Increase Total Laurate Levels. *Plant Phys*. 120: 739-746.
Knutzon et al. (1995) Cloning of a Coconut Endosperm cDNA Encoding a 1-Acyl-sn-Glycerol-3-Phosphate Acyltransferase That Accepts Medium-Chain-Length Substrates. *Plant Physiol*. 109:999-1006.
Krausgrill et al. "In transformed tobacco cells the apoplasmic invertase inhibitor operates as a regulatory switch of cell wall invertase", *Plant Journal* 13(2): 275-20 (1998).
Leonard et al. (1997) *Cuphea wrightii* Thipesterases Have Unexpected Broad Specificities on Saturated Fatty Acids. *Plant Molecular Biology* 34: 669-679.
Leonard et al. (1998) A *Cuphea* β-ketoacyl-ACP synthase shift the synthesis of fatty acids towards shorter chains in *Arabidopsis* seeds expressing *Cuphea* FatB thioesterases. *Plant J*. 13(5): 621-628.
Lian et al. "The Role of Aquaporin RWC3 in Drought Avoidance in Rice" *Plant Cell Physiol*, 45: 481-489 (2004).
Liu et al. "Camelina sativa transformation by floral dip and simple large-scale screening of markerless transformants" *In Vitro Cell Devel Biol-Animal*. 44:S40-S41 (2008).
Lord et al Glycolate oxidoreductase in *Escherichi coli*. (1972) *Biochimica et Biophysica Acta* 267:227-237.
Lu et al. "*Generation of transgenic plants of a potential oilseed crop Canekuba sativa by Agrobacterium-mediated transformation*" *Plant Cell Reports*, 2008. 27(2): p. 273-278.
Lucker et al. (2004) Increased and Altered Fragrance of Tobacco Plants after Metabolic Engineering Using Three Monoterpene Syntheses from Lemon. *Plant Physiol*, 134: 510-519.
Ohara et al. (2010) Monoterpene engineering in a woody plant *Eucalyptus camaldulensis* using a limonene synthase cDNA. *Plant Biotechnol*. January, 8: 28-37.
Peterhansel et al., 2010, The *Arabidopsis* Book 2010; 8:e0130, pp. 12.
Pidkowich et al. (2007) Modulating seed β-ketoacyl-acyl carrier protein synthase II level converts the composition of a temperate seed oil to that of a palm-like tropical oil, *PNAS* 104(11): 4742-4747.
Rausch et al. "Plant protein inhibitors of invertases", *Biochim Biophys Acta* 1696(2):253-61 (2004).
Reinscheid et al, "Characterization of the isocitrate lyase gene from Corynebacterium glutamicum and biochemical analysis of the enzyme" *J Bacteriol*, 1994. 178(12):3474-83.
Roth et al., 2004, Virus Research, 102: 97-108.
Ruan et al. "Sugar input, Metabolism, and Signaling Mediated by Invertase: Roles in Development, Yield Potential, and Response to Drought and Heat", *Molecular Plant*, 2010, 3(6): p. 942-955.
Sade et al. "Improving plant stress tolerance and yield production: is the tonoplast aquaporin SlTIP2;2 a key to isohydric to anisohydric conversion?", *New Phytol* 181: 651-661 (2009).
Sade et al. "The Role of Tobacco Aquaporin1 in Improving Water Use Efficiency, Hydraulic Conciuctivity, and Yield Production Under Salt Stress", *Plant Phys*. 152:245-254 (2010).
Schultes and Bartel, 2000, Science 289: 448-452.
Shonnard et al. "Camelina-derived jet fuel and diesel: Sustainable advanced biofuels" *Environmental Progress & Sustainable Energy*, 2010. 29(3): p. 382-392.
Small, 2007, Current Opinion in Biotechnology, 18: 148-153.
Sonnewald et al. "Transgenic tobacco plants expressing yeast-derived invertase in either the cytosol, vacuole or apoplast: a powerful tool for studying sucrose metabolism and sink/source interactions", *Plant J*. 1(1):95-106 (1991).
Tomlinson et al. Evidence that the hexose-to-sucrose ratio does not control the switch to storage product accumulation in oilseeds: analysis of tobacco seed development and effects of overexpressing apoplastic invertase. *J Exp. Bot*. 55(406): 2291-2303 (2004).
Uehlein et al. "Function of Nicotiana tabacum aqueporins as chloroplast gas pores challenges the concept of membrane $CO_2$ permeability", *Plant Cell*, 2008. 20(3): p. 648-57.
Uehlein et al. "The tobacco aquaporin NtAQP1 is a membrane $CO_2$ pore with physiologica functions", *Nature*, 2003. 425(6959): p. 734-7.
Voalker & AJ Kinney. (2001) Variations in the Biosynthesis of Seed-Storage Lipids. *Annu. Rev. Plant Physiol. Plant Mol. Biol*, 52: 335-361.
Voelker et al. (1992) Fatty Acid Biosynthesis Redirected to Medium Chains in Transgenic Oilseed Plants. *Science* 257: 72-74.
Voelker et al. (1996) Genetic Engineering of a Quantitative Trait: Metabolic and Genetic Parameters Influencing the Accumulation of Laurate in Rapeseed. Plant J. 9(2): 229-241.
Von Schaewen et al. "Expression of a yeast-derived invertase in the cell wail of tobacco and *Arabidopsis* plants leads to accumulation of carbohydrate and inhibition of photosynthesis and strongly influences growth and phenotype of transgenic tobacco plants" *Embo J*. 9(10):3033-44 (1990).
Wang et al. "Control of rice grain-filling and yield by a gene with a potential signature of domestication" *Nature Genetics*, 2008. 40(11): p. 1370-1374.
Ward et al. "Sucrose Transport in Higher Plants" *International Review of Cytology—a Survey of Cell Biology*, vol. 178:41-71 (1998).
Weil et al. A 17-kDa Nicotiana tabacum cell-wail peptide acts as an in-vitro inhibitor of the cell-wall isoform of acid invertase. *Planta* 193:438-445 (1994).
Yuan and Grotewold, 2015, Metabolic Engineering, 27: 83-91.
Zanor et al. "RNA Interference of LIN5 in Tomato Confirms Its Role in Controlling Brix Content, Uncovers the Influence of Sugars on the Levels of Fruit Hormones, and Demonstrates the Importance of Sucrose Cleavage for Normal Fruit Development and Fertility", *Plant Physiology* 150(3):1204-1218 (2009).
Glaser and Soll, 2004, In: Molecular Biology and Biotechnology of Plant Organelles, H. Danieil and C. Chase, eds., pp. 385-417.
Guo, H. et al., "Protein tolerance to random amino acid change", 2004, Proceedings of the National Academy of Sciences USA 101: 9205-9210.
Ji, Mikyoung Lee, Superoxide Reductase from the Hyperthermophilic Archaeon Pyrococcus furiosus; its Functions, Regulation, and Biotechnological Application, 2007, PhD Thesis, North Carolina State University, pp. 1-218.
Keskin, O. et al., A new, structurally nonredundant, diverse data set of protein-protein interfaces and its implications, 2004, Protein Science 13: 1043-1055.
Millar, A. et al., "Recent surprises in protein targeting to mitochondria and plastids", 2006, Current Opinion in Plant Biology 9: 610-615.
Pinto, Ana Fillpa et al., Reductive elimination of superoxide Structure and mechanism of superoxide reductases: 2010, Biochimica et Biophysica Acta 1804: 285-297.
Thornton, Janet et al., "From structure to function: Approaches and limitations", 2000, Nature Structural Biology, structural genomic supplement, Nov. 2000, 991-994.
Atkinson et al. "The interaction of plant biotic and abiotic stresses: from genes to the field" Experimental Botany, 63(10):3523-3544 (2012).

(56) References Cited

OTHER PUBLICATIONS

Vodes et al. "Targeting a heterologous protein to multiple plant organelles via rationally designed 5' mRNA tags" Journal of Biological Engineering, 7(20):1-10 (2013).

* cited by examiner pEG100: CTP-SOR pEG100: CTP-EGFP-SOR pEG100:CTP-SOR-EGFP

TRANSGENIC EXPRESSION OF ARCHAEA SUPEROXIDE REDUCTASE

STATEMENT OF PRIORITY

This application is a 35 U.S.C. § 371 national phase application of U.S. Application Ser. No. PCT/US2014/043393, filed Jun. 20, 2014, which claims the benefit, under 35 U.S.C. § 119 (a) of U.S. Application Ser. No. 61/838,817, filed Jun. 24, 2013, the entire contents of each of which are incorporated by reference herein.

STATEMENT OF GOVERNMENT SUPPORT

This invention was supported in part by funding provided under Grant No DE-AR0000207 from the United States Department of Energy (DOE). The United States government has certain rights in this invention.

STATEMENT REGARDING ELECTRONIC FILING OF A SEQUENCE LISTING

A Sequence Listing in ASCII text format, submitted under 37 C.F.R. § 1.821, entitled 5051-836WO_ST25.txt, 64,675 bytes in size, generated Jun. 17, 2014 and filed via EFS-Web, is provided in lieu of a paper copy. This Sequence Listing is hereby incorporated herein by reference into the specification for its disclosures.

FIELD OF THE INVENTION

The present invention relates to compositions and methods for expression of archaea superoxide reductase in a plant and other organisms by transforming the plant or other organism with a heterologous polynucleotide encoding a superoxide reductase from an archaeon species. The present invention further relates to methods and compositions for increasing disease resistance in a plant.

BACKGROUND

Reactive oxygen species (ROS) are chemically reactive molecules formed due to incomplete reduction of oxygen and include superoxide anions ($O^{2-}$), hydrogen peroxide ($H_2O_2$), and hydroxyl radicals (HO). ROS are highly reactive due to the presence of unpaired electrons. ROS are natural byproducts of normal metabolism of oxygen in many organisms and play an important role in cell signaling and homeostasis. However, elevated levels of ROS can have detrimental results. The levels of ROS can increase dramatically when an organism is exposed to various environmental stresses such as exposure to heat, excessive light, drought, anoxia, toxins, pathogens, and the like, resulting in oxidative damage and cell death. In plants, for example, oxidative damage from excess ROS can result in reduced photosynthetic efficiency. Plants and other organisms have endogenous ROS metabolizing enzymes such as superoxide dismutase, catalase and peroxidase for preventing the buildup of ROS. However, these endogenous protective mechanisms can be insufficient when the organism experiences environmental stress conditions.

SUMMARY OF THE INVENTION

In one aspect, the present invention provides a stably transformed plant, plant part or plant cell, comprising a heterologous polynucleotide encoding a superoxide reductase from an archaeon species, wherein said stably transformed plant, plant part or plant cell has increased disease resistance as compared to a control (e.g., a plant, plant part or plant cell that does not comprise said heterologous polynucleotide encoding a superoxide reductase from an archaeon species). In some aspects, the superoxide reductase is localized to the cytosolic membrane, the chloroplast, the peroxisome, the cell wall, mitochondria, and/or as a membrane associated protein of said transformed plant, plant part or plant cell.

In another aspect of the invention, the present invention provides a stably transformed plant, plant part, plant cell, yeast cell or bacterial cell comprising a first heterologous polynucleotide encoding a superoxide reductase from an archaeon species and a second heterologous polynucleotide encoding a $CO_2$ transporter (e.g., aquaporin). In some aspects, the superoxide reductase is localized to the chloroplast, cytosolic membrane, peroxisome, cell wall, mitochondria, periplasm and/or as a membrane associated protein of said stably transformed plant, plant cell, plant part, yeast cell or bacterial cell.

In a further aspect, the present invention provides a method of increasing disease resistance in a plant, plant cell, or plant part, comprising: introducing into said plant, plant cell, or plant part a heterologous polynucleotide encoding a superoxide reductase from an archaeon species to produce a stably transformed plant, plant cell, or plant part, thereby producing a plant, plant part, or plant cell having increased disease resistance as compared to a control. In some aspects, the stably transformed plant part or plant cell is regenerated into a stably transformed plant comprising in its genome the heterologous polynucleotide encoding a superoxide reductase from an archaeon species, thereby producing a plant having increased disease resistance as compared to a control.

In other aspects, the present invention provides progeny and crops produced from the stably transformed plants of the invention as well as products produced from the transformed plants, plant cells, plant parts, yeast cells and/or bacterial cells of this invention.

The foregoing and other objects and aspects of the present invention are explained in detail in the drawings and specification set forth below.

DETAILED DESCRIPTION

Figure 1:
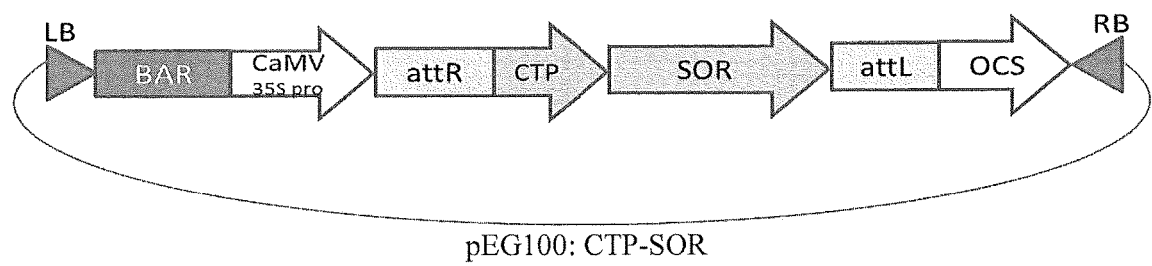
FIG. 1 shows vector maps of constructs for plant transformation: pEG100: CTP-SOR, pEG100:CTP-EGFP-SOR and pEG100:CTP-SOR-EGFP.
Figure 1:
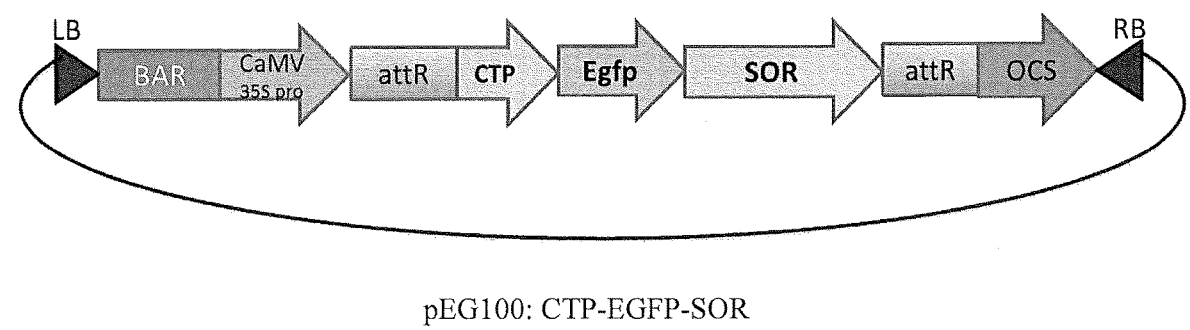
Figure 1:
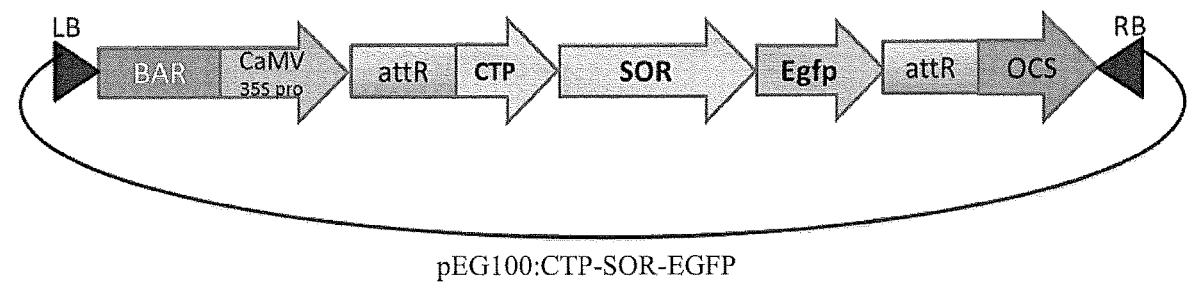

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or"). The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

*Archaea* are single celled microorganisms many of which have developed the ability to survive in extreme environments such as high heat and salt (i.e., extremophiles). *Pyrococcus furiosus* is an extremophilic (hyperthermophilic) species of archaea with optimum growth at 100° C. It is found in hydrothermal vents and is a strict anaerobe at growth permissible temperatures. *P. furiosus* uses an enzyme, superoxide reductase (SOR), to deal with ROS. *P. furiosus* SOR has a functional temperature range of about 4° C. to about 100° C. Unlike superoxide dismutase (SOD), which is an endogenous enzyme found in plants, including algae, and in yeast and aerobic bacteria, SOR is more efficient in removing ROS and does so without producing oxygen (thereby reducing the potential for further ROS generation). Notably, there is substantial similarity between SOR from *P. furiosus* and other archaea as well as from mesophilic bacteria. Non-limiting examples of additional archaea SOR useful with this invention include those listed in Table 1, below.

TABLE 1

Exemplary archaeal species useful with the invention

| Archaeal Species | SOR Accession # | % Identity to *P. furiosus* SOR |
| --- | --- | --- |
| *Thermococcus litoralis* DSM 5473 | CP006670.1 | 97% |
| *Thermococcus sibiricus* MM 739 | CP001463.1 | 88% |
| *Pyrococcus horikoshii* OT3 | BA000001.2 | 74% |
| *Pyrococcus* sp. ST04 | CP003534.1 | 73% |
| *Thermococcus nautili* strain 30-1 | CP007264.1 | 73% |
| *Thermococcus* sp. AM4 | CP002952.1 | 73% |
| *Pyrococcus yayanosii* CH1 | CP002779.1 | 71% |
| *Thermococcus gammatolerans* EJ3 | CP002670.1 | 70% |
| *Thermococcus onnurineus* NA1 | CP000855.1 | 69% |
| *Candidatus Korarchaeum cryptofilum* OPF8 | CP000968.1 | 69% |
| *Archaeoglobus fulgidus* DSM 4304 | AE000782.1 | 68% |
| *Ferroglobus placidus* DSM 10642 | CP001899.1 | 67% |
| *Thermococcus barophilus* MP | CP006965.1 | 66% |
| *Aciduliprofundum* sp. MAR08-339 | CP003168.1 | 65% |
| *Archaeoglobus sulfaticallidus* PM70-1 | CP005290.1 | 65% |

Accordingly, the present invention is directed to transgenic plants, plant parts, and/or plant cells comprising a heterologous polynucleotide encoding a superoxide reductase from an archaeon species and methods of increasing resistance to disease in said transgenic plants, plant cells, and/or plant parts. Other aspects of the invention are directed to a stably transformed plant, plant cell, plant part, yeast cell or bacterial cell comprising a heterologous polynucleotide encoding a superoxide reductase (SOR) from an archaeon species and a heterologous polynucleotide encoding a $CO_2$ transporter, wherein the stably transformed plant has increased disease resistance, increased stress tolerance and increased yield.

Thus, a first aspect of the present invention provides a stably transformed plant, plant part and/or plant cell comprising a heterologous polynucleotide encoding a superoxide reductase (SOR) from an archaeon species, wherein said stably transformed plant, plant cell, and/or plant part has increased disease resistance as compared to a control (e.g., a plant, plant part or plant cell that does not comprise said heterologous polynucleotide encoding a superoxide reductase from an archaeon species). A second aspect of the present invention provides a stably transformed plant, plant part and/or plant cell comprising a heterologous polynucleotide encoding a superoxide reductase (SOR) from an archaeon species, wherein when the stably transformed plant, plant cell, and/or plant part is exposed to abiotic stress conditions said stably transformed plant, plant cell, and/or plant part has increased disease resistance as compared to a control (e.g., a plant, plant part or plant cell exposed to abiotic stress that does not comprise said heterologous polynucleotide encoding a superoxide reductase from an archaeon species). In a third aspect of the present invention provides a stably transformed plant, plant part and/or plant cell comprising a heterologous polynucleotide encoding a superoxide reductase (SOR) from an archaeon species, wherein the stably transformed plant, plant cell, and/or plant part is first exposed to abiotic stress conditions, then removed from said abiotic stress conditions and has increased disease resistance as compared to a control (e.g., a plant, plant part or plant cell that does not comprise said heterologous polynucleotide encoding a superoxide reductase from an archaeon species). In some embodiments, the superoxide reductase is localized to the cytosolic membrane, the chloroplast, the peroxisome, the cell wall, mitochondria, and/or as a membrane associated protein of said stably transformed plant, plant cell, and/or plant part. In particular embodiments, the archaeon superoxide reductase is not localized in the cytosol or cytosolic membrane of a plant, plant part or plant cell. In further embodiments, the archaeon superoxide reductase is not localized in the cytosol and/or cytosolic membrane of a plant, plant part or plant cell when said plant, plant part or plant cell is from *Arabidopsis thaliana* and/or a higher plant.

In another aspect of the invention, a stably transformed plant, plant part, plant cell, yeast cell or bacterial cell comprising a first heterologous polynucleotide encoding a superoxide reductase from an archaeon species and a second heterologous polynucleotide encoding a $CO_2$ transporter (e.g., aquaporin) is provided. In some embodiments, the superoxide reductase can be localized to the cytosolic membrane, the chloroplast, the peroxisome, the cell wall, mitochondria, and/or as a membrane associated protein of said stably transformed plant, plant part, plant cell, yeast cell or bacterial cell. In particular embodiments, the archaeon superoxide reductase is not localized in the cytosol or cytosolic membrane of a plant, plant part or plant cell. In further embodiments, the archaeon superoxide reductase is not localized in the cytosol and/or cytosolic membrane of a plant, plant part or plant cell when said plant, plant part or plant cell is from *Arabidopsis thaliana* and/or a higher plant. In still further embodiments, a stably transformed plant, plant part or plant cell comprising a first heterologous polynucleotide encoding a superoxide reductase from an archaeon species and a second heterologous polynucleotide encoding a $CO_2$ transporter can have increased disease resistance as compared to a control plant, plant part or plant cell that does not comprise said first heterologous polynucleotide encoding a superoxide reductase from an archaeon species and said second heterologous polynucleotide encoding a $CO_2$ transporter. In other embodiments, a stably transformed plant, plant part or plant cell comprising a first heterologous polynucleotide encoding a superoxide reductase from an archaeon species and a second heterologous polynucleotide encoding a $CO_2$ transporter can have increased stress resistance or tolerance and/or increased yield as compared to a control plant, plant part or plant cell that does not comprise said first heterologous polynucleotide encoding a superoxide reductase from an archaeon species and said second heterologous polynucleotide encoding a $CO_2$ transporter.

In a further aspect, the present invention provides a method of increasing disease resistance (e.g., decreasing disease symptoms, decreasing pathogen growth and reproduction) in a plant, plant cell, or plant part, comprising: introducing into said plant, plant cell, or plant part a heterologous polynucleotide encoding a superoxide reductase from an archaeon species to produce a stably transformed plant, plant cell, or plant part, thereby producing a plant, plant part, or plant cell having increased disease resistance as compared to a control (e.g., a plant, plant part or plant cell that does not comprise said heterologous polynucleotide encoding a superoxide reductase from an archaeon species). In some aspects, the present invention provides a method of increasing disease resistance (e.g., decreasing disease symptoms, decreasing pathogen growth and reproduction) in a plant, plant cell, or plant part, comprising: introducing into said plant, plant cell, or plant part a heterologous polynucleotide encoding a superoxide reductase from an archaeon species to produce a stably transformed plant, plant cell, or plant part; and exposing said stably transformed plant, plant cell, and/or plant part to abiotic stress conditions, thereby producing a plant, plant part, or plant cell having increased disease resistance as compared to a control (e.g., a plant, plant part or plant cell that is exposed to abiotic stress conditions and does not comprise said heterologous polynucleotide encoding a superoxide reductase from an archaeon species). In a further aspect, the present invention provides a method of increasing disease resistance (e.g., decreasing disease symptoms, decreasing pathogen growth and reproduction) in a plant, plant cell, or plant part, comprising: introducing into said plant, plant cell, or plant part a heterologous polynucleotide encoding a superoxide reductase from an archaeon species to produce a stably transformed plant, plant cell, or plant part; exposing said stably transformed plant, plant cell, and/or plant part to abiotic stress conditions; and removing the stably transformed plant, plant cell, and/or plant part from said abiotic stress conditions, thereby producing a plant, plant part, or plant cell having increased disease resistance as compared to a control (e.g., a plant, plant part or plant cell that is exposed to abiotic stress conditions, removed from abiotic stress conditions and does not comprise said heterologous polynucleotide encoding a superoxide reductase from an archaeon species). In some embodiments, the archaeon superoxide reductase can be localized to the cytosolic membrane, the chloroplast, the peroxisome, the cell wall, mitochondria, and/or as a membrane associated protein of said stably transformed plant, plant cell, and/or plant part. In particular embodiments, the archaeon superoxide reductase is not localized in the cytosol or cytosolic membrane of a plant, plant part or plant cell. In further embodiments, the archaeon superoxide reductase is not localized in the cytosol and/or cytosolic membrane of a plant, plant part or plant cell when said plant, plant part or plant cell is from *Arabidopsis thaliana* and/or a higher plant. In still further embodiments, the method further comprises introducing into said stably transformed plant a heterologous polynucleotide encoding a $CO_2$ transporter.

In other aspects of the invention, a method of increasing stress resistance or tolerance and/or increasing yield in a plant in the presence of stress in a plant, plant cell, or plant part is provided, the method comprising: introducing into said plant, plant cell, or plant part a first heterologous polynucleotide encoding a superoxide reductase from an archaeon species and a second heterologous polynucleotide encoding a $CO_2$ transporter to produce a stably transformed plant, plant cell, or plant part, thereby producing a plant, plant part, or plant cell having increased stress resistance or tolerance and/or increased yield in a plant in the presence of stress as compared to a control (e.g., a plant, plant part or plant cell that does not comprise said heterologous polynucleotide encoding a superoxide reductase from an archaeon species or said heterologous polynucleotide encoding a $CO_2$ transporter). As disclosed herein, the superoxide reductase can be localized to the cytosolic membrane, the chloroplast, the peroxisome, the cell wall, mitochondria, and/or as a membrane associated protein of said stably transformed plant, plant cell, and/or plant part. In particular embodiments, the archaeon superoxide reductase is not localized in the cytosol or cytosolic membrane of a plant, plant part or plant cell. In further embodiments, the archaeon superoxide reductase is not localized in the cytosol and/or cytosolic membrane of a plant, plant part or plant cell when said plant, plant part or plant cell is from *Arabidopsis thaliana* and/or a higher plant.

The terms "increase," "increasing," "increased," "enhance," "enhanced," "enhancing," and "enhancement" (and grammatical variations thereof), as used herein, describe an elevation in, for example, the resistance of a plant, plant part or plant cell to disease. This increase can be observed by comparing the increase in the plant, plant part or plant cell transformed with the heterologous polynucleotide encoding said SOR to the appropriate control (e.g., a plant, plant part or plant cell lacking (i.e., not transformed with) the heterologous polynucleotide encoding said SOR from an archaeon species). Thus, as used herein, the terms "increase," "increasing," "increased," "enhance," "enhanced," "enhancing," and "enhancement" (and grammatical variations thereof), and similar terms indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control (e.g., a plant, plant part, plant cell that does not comprise said heterologous polynucleotide encoding SOR from an archaeon species or a plant, plant part, plant cell, yeast cell, bacterial cell that does not comprise said heterologous polynucleotide encoding SOR from an archaeon species or said heterologous polynucleotide encoding a $CO_2$ transporter).

As used herein, the terms "reduce," "reduced," "reducing," "reduction," "diminish," "suppress," and "decrease" (and grammatical variations thereof), describe, for example, a decrease in the disease observed in a plant, plant part, or plant cell comprising in its genome said heterologous polynucleotide encoding SOR from an archaeon species as compared to a control plant, plant part, or plant cell that does not comprise in its genome said heterologous polynucleotide encoding SOR from an archaeon species. Thus, as used herein, the terms "reduce," "reduces," "reduced," "reduction," "diminish," "suppress," and "decrease" and similar terms mean a decrease of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, and the like, or more, or any range therein, as compared to a control (e.g., a plant, plant part, or plant cell that does not comprise in its genome said heterologous polynucleotide encoding SOR from an archaeon species or a plant, plant part, plant cell, yeast cell and/or bacterial cell that does not comprise said heterologous polynucleotide encoding SOR from an archeaon species and said heterologous polynucleotide encoding a $CO_2$ transporter).

As used herein, "increasing disease resistance" or "increased disease resistance" refers to, for example, decreasing disease symptoms on a plant in response to exposure to a pathogen, and/or decreasing the ability of a pathogen to survive, grow and/or reproduce on a plant modified as described herein (e.g., a transgenic plant comprising a polynucleotide encoding SOR or a transgenic plant comprising a polynucleotide encoding SOR and a polynucleotide encoding a $CO_2$ transporter).

In some embodiments, an increase in disease resistance can mean a reduction in the size and in the number of disease lesions on the plant. Thus, in particular embodiments, a decrease in the number of lesions can be from about 10% to about 100%, from about 20% to about 90%, from about 30% to about 85%, from about 40% to about 80%, or from about 50% to about 75%. Thus, in some embodiments, a decrease in the number of lesions can be from about 10%, 15%, 20%, 25%, 30%, 35%, 40%, 45%, 50%, 55%, 60%, 65%, 70%, 75%, 80%, 85%, 90%, 95%, 100% or any range therein and the like. In other embodiments, the size of the lesion can be reduced by about 5%, 10%, 15%, 20%, 25%, 30%, 35%, 40%, 45%, 50%, 55%, 60%, 65%, 70%, 75%, 80%, 85%, 90%, 95%, 100% or any range therein and the like.

As used herein, "increased stress resistance or stress tolerance" or "increasing stress resistance or stress tolerance" refers to the ability of a plant to be in the presence of an abiotic stress as defined herein resulting in a reduced affect of said abiotic stress on the plant's growth, metabolism, yield and/or viability as compared to a control plant (e.g., a plant not comprising the heterologous polynucleotides encoding SOR and a $CO_2$ transporter as described herein).

"Yield" as used herein, refers to the amount (as measured by weight or number) of tissue produced per plant. Plant tissues can include any plant part (e.g., leaves, stems, stalks, seeds, fruits, and the like) or the whole plant itself.

As used herein, the terms "express," "expresses," "expressed" or "expression," and the like, with respect to a nucleotide sequence (e.g., RNA or DNA) indicates that the nucleotide sequence is transcribed and, optionally, translated. Thus, a nucleotide sequence may express a polypeptide of interest or a functional untranslated RNA. A "functional" RNA includes any untranslated RNA that has a biological function in a cell, e.g., regulation of gene expression. Such functional RNAs include but are not limited to RNAi (e.g., siRNA, shRNA, antisense RNA), miRNA, ribozymes, RNA aptamers, and the like.

In some embodiments, the archaeon species can be a species from the genus *Pyrococcus*, a species from the genus *Thermococcus*, or a species from the genus *Archaeoglobus*. In other embodiments, the archaeon species can be *Pyrococcus furiosus* and the heterologous polynucleotide encoding a SOR can be a nucleotide sequence of SEQ ID NO:1 or SEQ ID NO:2. In some embodiments, the heterologous polynucleotide encoding a SOR encodes an amino acid sequence of SEQ ID NO:3 or SEQ ID NO:4. Thus, in some embodiments, the invention provides a nucleotide sequence comprising, essentially consisting of, consisting of (a) a nucleotide sequence of SEQ ID NO:2; (b) a nucleotide sequence that encodes a polypeptide comprising an amino acid sequence of SEQ ID NO:4; and/or (c) a nucleotide sequence that differs from the nucleotide sequences of (a) or (b) above due to the degeneracy of the genetic code. In other embodiments, the invention provides an isolated polypeptide comprising, essentially consisting of or consisting of an amino acid sequence of SEQ ID NO:4.

In some embodiments, the heterologous polynucleotide encoding a SOR is operably associated with a targeting nucleotide sequence encoding a signal peptide that targets the heterologous SOR to the cytosol, cytosolic membrane (e.g., cytosolic surface of the plasmamembrane and other endogenous membranes including the nuclear envelope and endoplasmic reticulum), chloroplast, cell wall, peroxisome, mitochondria, periplasm and/or as a membrane associated protein. The signal sequence may be operably linked at the N- or C-terminus of the nucleic acid molecule. In some embodiments, the heterologous polynucleotide encoding a SOR is not operably associated with a targeting nucleotide sequence that encodes a signal peptide targeting said SOR to the cytosol and/or cytosolic membrane. In other embodiments, the heterologous polynucleotide encoding a SOR is not operably associated with a targeting nucleotide sequence that encodes a signal peptide targeting said SOR to the cytosolic membrane. In some particular embodiments, when the targeting nucleotide sequence encodes a signal peptide that targets the SOR to the cytosol and/or cytosolic membrane, the plant, plant part and/or plant cell is not from a higher plant. In other embodiments, when the targeting nucleotide sequence encodes a signal peptide that targets the SOR to the cytosol and/or cytosolic membrane, the plant, plant part and/or plant cell is not *Arabidopsis thaliana* or not from *Arabidopsis thaliana*.

Aquaporin is a high affinity $CO_2$ transporter with high similarity to the human $CO_2$ pore (AQP1) that has been identified in tobacco (NtAQP1, e.g., aquaporin) and shown to facilitate $CO_2$ membrane transport in plants (Uehlein et al. *Nature* 425(6959): 734-7 (2003); Uehlein et al. *Plant Cell* 20(3):648-57 (2008); Flexas et al. *Plant J.* 48(3):427-39 (2006)). In some embodiments, a heterologous polynucleotide encoding a polypeptide having the activity of a $CO_2$/bicarbonate transporter can be used. Thus, in some embodiments, a heterologous polynucleotide encoding a polypeptide having the activity of a $CO_2$ transporter is from a plant (including, but not limited to, a saltwater algae), an extremophile archea and/or extremophile bacteria (e.g. from the marine microalgae *Dunaliella* spp.; and/or *Hydrogenobacter thermophilis*).

In representative embodiments, a heterologous polynucleotide encoding a $CO_2$ transporter (e.g., aquaporin) can comprise, consist essentially of or consist of a nucleotide sequence of SEQ ID NO:58, SEQ ID NO:60 and/or SEQ ID NO:62, or a nucleotide sequence having substantial identity to said nucleotide sequences of SEQ ID NO:58, SEQ ID NO:60 and/or SEQ ID NO:62. In other embodiments, an amino acid sequence of a $CO_2$ transporter can optionally comprise, consist essentially of or consist of the amino acid sequence of SEQ ID NO:59, SEQ ID NO:61 and/or SEQ ID NO:63, or an amino acid sequence having substantial identity to said nucleotide sequences of the amino acid sequence of SEQ ID NO:59, SEQ ID NO:61 and/or SEQ ID NO:63.

In particular embodiments, in addition to a heterologous polynucleotide encoding a SOR or a heterologous polynucleotide encoding a SOR and a heterologous polynucleotide encoding a $CO_2$ transporter (e.g., aquaporin), a plant, plant part, plant cell, yeast or bacterial cell can further comprise an archaeal rubrerythrin reductase for conversion of hydrogen peroxide to water. Rubrerythrin reductase is an iron-dependent peroxidase that functions in vivo to remove the peroxide produced by superoxide reductase. Thus, a further embodiment of the invention includes a stably transformed plant comprising an expression cassette that comprises a SOR and a rubrerythrin reductase or an expression cassette that comprises SOR, $CO_2$ transporter and rubrerythrin reductase. In some embodiments, the SOR and rubrerythrin reductase are co-localized (i.e., they are expressed and targeted to the same or similar position in the transformed cell). In other embodiments, the SOR, $CO_2$ transporter, and rubrerythrin reductase are co-localized.

In some embodiments, an archaeal rubrerythrin reductase can be from *Pyrococcus furiosus*. In further embodiments, an archaeal rubrerythrin reductase can be encoded by the nucleotide sequence of SEQ ID NO:50. In still further embodiments, an archaeal rubrerythrin reductase can comprise, consist essentially of, or consist of the amino acid sequence of SEQ ID NO:51.

As discussed herein, the SOR, $CO_2$ transporter, and/or rubrerythrin reductase can be targeted to particular organelles. Thus, in some embodiments, the SOR, $CO_2$ transporter and/or rubrerythrin reductase polypeptides are in operable linkage or fused with a targeting or signal peptide (e.g., fusion protein) that directs the protein to the desired cellular location.

Signal peptides (and the targeting nucleotide sequences encoding them) are well known in the art and can be found in public databases such as the "Signal Peptide Website: An Information Platform for Signal Sequences and Signal Peptides." (www.signalpeptide.de); the "Signal Peptide Database" (proline.bic.nus.edu.sg/spdb/index.html) (Choo et al., *BMC Bioinformatics* 6:249 (2005)(available on www.biomedcentral.com/1471-2105/6/249/abstract); ChloroP (www.cbs.dtu.dk/services/ChloroP/; predicts the presence of chloroplast transit peptides (cTP) in protein sequences and the location of potential cTP cleavage sites); LipoP (www.cbs.dtu.dk/services/LipoP/; predicts lipoproteins and signal peptides in Gram negative bacteria); MITOPROT (ihg2.helmholtz-muenchen.de/ihg/mitoprot.html; predicts mitochondrial targeting sequences); PlasMit (gecco.org.chemie.uni-frankfurt.de/plasmit/index.html; predicts mitochondrial transit peptides in *Plasmodium falciparum*); Predotar (urgi.versailles.inra.fr/predotar/predotar.html; predicts mitochondrial and plastid targeting sequences); PTS1 (mendel.imp.ac.at/mendeljsp/sat/ptsl/PTSlpredictor.jsp; predicts peroxisomal targeting signal 1 containing proteins); SignalP (www.cbs.dtu.dk/services/SignalP/; predicts the presence and location of signal peptide cleavage sites in amino acid sequences from different organisms: Gram-positive prokaryotes, Gram-negative prokaryotes, and eukaryotes). The SignalP method incorporates a prediction of cleavage sites and a signal peptide/non-signal peptide prediction based on a combination of several artificial neural networks and hidden Markov models; and TargetP (www.cbs.dtu.dk/services/TargetP/); predicts the subcellular location of eukaryotic proteins—the location assignment is based on the predicted presence of any of the N-terminal presequences: chloroplast transit peptide (cTP), mitochondrial targeting peptide (mTP) or secretory pathway signal peptide (SP)). (See also, von Heijne, G., *Eur J Biochem* 133 (1) 17-21 (1983); Martoglio et al. *Trends Cell Biol* 8 (10):410-5 (1998); Hegde et al. *Trends Biochem Sci* 31(10):563-71 (2006); Dultz et al. *J Biol Chem* 283(15):9966-76 (2008); Emanuelsson et al. *Nature Protocols* 2(4) 953-971(2007); Zuegge et al. 280(1-2):19-26 (2001); Neuberger et al. *J Mol Biol.* 328(3):567-79 (2003); and Neuberger et al. *J Mol Biol.* 328(3):581-92 (2003)).

Exemplary signal peptides include, but are not limited to those provided in Table 2.

TABLE 2

Amino acid sequences of representative signal peptides.

| Source | Sequence | Target |
| --- | --- | --- |
| Rubisco small subunit (tobacco) | MASSVLSSAAVATRSNVAQANMVAPFTGLKSAASFPVSR KQNLDITSIASNGGRVQC (SEQ ID NO: 5) | chloroplast |
| Saccharomyces cerevisiae cox4 | MLSLRQSIRFFKPATRTLCSSRYLL (SEQ ID NO: 7) | mitochondria |
| Arabidopsis aconitase | MYLTASSSASSSIIRAASSRSSSLFSFRSVLSPSVSSTSPSSLL ARRSFGTISPAFRRWSHSFHSKPSPFRFTSQIRA (SEQ ID NO: 9) | mitochondria |
| Yeast aconitase | MLSARSAIKRPIVRGLATV (SEQ ID NO: 40) | mitochondria |
| Arabidopsis proline-rich protein 2 (AT2G21140) | MRILPKSGGGALCLLFVFALCSVAHS (SEQ ID NO: 11) | cell wall/secretory pathway |
| PTS-2 (conserved in eukaryotes) | RLX$_5$HL (SEQ ID NO: 13) MRLSIHAEHL (SEQ ID NO: 14) SKL | peroxisome |
| Arabidopsis presequence protease1 (AT3G19170) | MLRTVSCLASRSSSSLFFRFFRQFPRSYMSLTSSTAALRVPSRNLR RISSPSVAGRRLLLRRGLRIPSAAVRSVNGQFSRLSVRA (SEQ ID NO: 16) | mitochondria and chloroplast |
| Chlamydomonas reinhardtii-(Stroma-targeting cTPs: photosystem I (PSI) subunits P28, P30, P35 and P37, respectively) | MALVARPVLSARVAASRPRVAARKAVRVSAKYGEN (SEQ ID NO: 41) MQALSSRVNIAAKPQRAQRLVVRAEEVKA (SEQ ID NO: 42) MQTLASRPSLRASARVAPRRAPRVAVVTKAALDPQ (SEQ ID NO: 43) MQALATRPSAIRPTKAARRSSVVVRADGFIG (SEQ ID NO: 44) | chloroplast |
| C. reinhardtii-chlorophyll a/b protein (cabII-1) | MAFALASRKALQVTCKATGKKTAAKAAAPKSSGVEFYGPNRAK WLGPYSEN (SEQ ID NO: 45) | chloroplast |
| C. reinhardtii-Rubisco small subunit | MAAVIAKSSVSAAVARPARSSVRPMAALKPAVKAAPVAAPAQA NQMMVWT (SEQ ID NO: 46) | chloroplast |
| C. reinhardtii-ATPase-γ | MAAMLASKQGAFMGRSSFAPAPKGVASRGSLQVVAGLKEV (SEQ ID NO: 47) | chloroplast |
| Escherichia coli phoA alkaline phosphatase | MKQSTIAKAKKPLLFTPVTKA (SEQ ID NO: 48) | periplasm |
| Arabidopsis thaliana abscisic acid receptor PYL10 | CVVQ (SEQ ID NO: 34) | membrane |

$X_5$ means any five amino acids can be present in the sequence to target the protein to the peroxisome (e.g. RLAVAVAHL, SEQ ID NO: 49).

Thus, in representative embodiments of the invention, a heterologous polynucleotide encoding a SOR and/or a heterologous polynucleotide encoding an $CO_2$ transporter to be expressed in a plant, plant cell, plant part can be operably linked to a chloroplast targeting sequence encoding a chloroplast signal peptide, optionally wherein said chloroplast signal peptide is encoded by an amino acid sequence that includes, but is not limited to, the amino acid sequence of SEQ ID NO:5, SEQ ID NO:41, SEQ ID NO:42, SEQ ID NO:43, SEQ ID NO:44, SEQ ID NO:45, SEQ ID NO:46, or SEQ ID NO:47.

In other embodiments of the invention, a heterologous polynucleotide encoding a SOR and/or a heterologous polynucleotide encoding a $CO_2$ transporter to be expressed in a plant, plant part, plant cell or yeast cell can be operably linked to a mitochondrial targeting sequence encoding a mitochondrial signal peptide, optionally wherein said mitochondrial signal peptide is encoded by an amino acid sequence that includes, but is not limited to, the amino acid sequence of SEQ ID NO:7, SEQ ID NO:9, or SEQ ID NO:40.

In further embodiments, a heterologous polynucleotide encoding a SOR to be expressed in a plant, plant part, plant cell, yeast cell, or bacterial cell can be operably linked to a cell wall targeting sequence encoding a cell wall signal peptide, optionally wherein said cell wall signal peptide is encoded by an amino acid sequence that includes, but is not limited to, the amino acid sequence of SEQ ID NO:11.

In still further embodiments of the invention, a heterologous polynucleotide encoding a SOR to be expressed in a plant, plant part, plant cell, or a yeast cell can be operably linked to a peroxisomal targeting sequence encoding a peroxisomal signal peptide, optionally wherein said peroxisomal signal peptide is encoded by an amino acid sequence that includes, but is not limited to, the amino acid sequence of SEQ ID NO:13, SEQ ID NO:14, or SKL.

In additional embodiments, a heterologous polynucleotide encoding a SOR to be expressed in a bacterial cell can be operably linked to a periplasmic targeting sequence encoding a periplasmic signal peptide, optionally wherein said periplasmic signal peptide is encoded by an amino acid sequence that includes, but is not limited to, the amino acid sequence of SEQ ID NO:48.

In some embodiments, a heterologous polynucleotide encoding a SOR and/or a heterologous polynucleotide encoding a $CO_2$ transporter (e.g., aquaporin) to be expressed in a plant, plant part, plant cell, yeast cell or bacterial cell can be operably linked to a membrane targeting sequence encoding a membrane signal peptide, optionally wherein said membrane signal peptide is encoded by an amino acid sequence that includes, but is not limited to, the amino acid sequence of SEQ ID NO:34. In some embodiments, wherein when the heterologous polynucleotide encoding a SOR and/or a heterologous polynucleotide encoding a $CO_2$ transporter are targeted to a membrane, the SOR and/or the $CO_2$ transporter can be either linked directly to the membrane or to the membrane via a linkage to a membrane associated protein. In representative embodiments, a membrane associated protein includes but is not limited to the plasma membrane NADH oxidase (RbohA) (for respiratory burst oxidase homolog A) (Keller et al. *The Plant Cell Online* 10: 255-266 (1998)), annexin1 (ANN1) from *Arabidopsis thaliana* (Laohavisit et al. *Plant Cell Online* 24: 1522-1533 (2012)), and/or the nitrate transporter CHL1 (AtNRT1.1) (Tsay et al. "The Role of Plasma Membrane Nitrogen Transporters in Nitrogen Acquisition and Utilization," In, *The Plant Plasma Membrane* 19:223-236 Springer Berlin/Heidelberg (2011)).

Targeting to a membrane is similar to targeting to an organelle. Thus, specific sequences on a protein (targeting sequences or motifs) can be recognized by a transporter, which then imports the protein into an organelle or in the case of membrane association, the transporter can guide the protein to and associate it with a membrane. Thus, for example, a specific cysteine residue on a C-terminal motif of a protein can be modified posttranslation where an enzyme (prenyltransferases) then attaches a hydrophobic molecule (geranylgeranyl or farnesyl) (See, e.g., Running et al. *Proc Natl Acad Sci USA* 101: 7815-7820 (2004); Maurer-Stroh et al. *Genome Biology* 4:212 (2003)). This hydrophobic addition guides and associates the protein to a membrane (in case of the cytosol, the membrane would be the plasmamembrane or the cytosolic site of the nuclear membrane (Polychronidou et al. Molecular Biology of the Cell 21: 3409-3420 (2010)). More specifically, in representative embodiments, a protein prenyltransferase can catalyze the covalent attachment of a 15-carbon farnesyl or 20-carbon geranylgeranyl isoprenoid to C-terminal cysteines of selected proteins carrying a CaaX motif where C=cysteine; a=aliphatic amino acid; x=any amino acid. For plants, this motif most often is CVVQ. The addition of prenyl groups facilitates membrane association and protein-protein interactions of the prenylated proteins.

In still other embodiments of the invention, a signal peptide can direct a SOR, a $CO_2$ transporter or a rubrerythrin reductase to more than one organelle (e.g., dual targeting). Thus, in some embodiments, a signal peptide that can target the polypeptides to more than one organelle is encoded by an amino acid sequence that includes, but is not limited to, the amino acid sequence of SEQ ID NO:16.

In some embodiments, the heterologous polynucleotide encoding a SOR from an archaeon species, the heterologous polynucleotide encoding a $CO_2$ transporter (e.g., aquaporin) and/or the heterologous polynucleotide encoding an archaeon rubrerythrin reductase can be comprised within an expression cassette. As used herein, "expression cassette" means a recombinant nucleic acid molecule comprising at least one nucleotide sequence of interest (e.g., the heterologous polynucleotide encoding SOR, the heterologous polynucleotide encoding a $CO_2$ transporter and/or the heterologous polynucleotide encoding an archaeon rubrerythrin reductase), wherein said heterologous polynucleotide is operably associated with at least a control sequence (e.g., a promoter). Thus, some embodiments of the invention provide expression cassettes designed to express a polynucleotide encoding an archaeon SOR, a polynucleotide encoding a $CO_2$ transporter and/or a polynucleotide encoding rubrerythrin reductase. In this manner, for example, a promoter operably associated with a heterologous polynucleotide encoding a SOR from an archaeon species (e.g., SEQ ID NO:1 or SEQ ID NO:2), and/or functional fragment thereof) are provided in expression cassettes for expression in a plant, plant part, plant cell, bacterial cell and/or yeast cell. In other embodiments, a promoter operably associated with a heterologous polynucleotide encoding a $CO_2$ transporter (e.g., SEQ ID NO:58, SEQ ID NO:59 or SEQ ID NO:60), and/or functional fragment thereof) are provided in expression cassettes for expression in a plant, plant part, plant cell, bacterial cell and/or yeast cell. In this manner, for example, a promoter operably associated with a heterologous polynucleotide encoding a rubrerythrin reductase from an archaeon species (e.g., SEQ ID NO:50), and/or functional fragment thereof) are provided in expression cassettes for expression in a plant, plant part, plant cell, bacterial cell and/or yeast cell.

In some embodiments, the heterologous polynucleotide encoding a SOR can be operably linked to the same promoter that is operably linked to the heterologous polynucleotide encoding a $CO_2$ transporter and/or the heterologous polynucleotide encoding a rubrerythrin reductase. In other embodiments, the heterologous polynucleotide encoding a SOR is operably linked to a different promoter than that which is operably linked to the heterologous polynucleotide encoding a $CO_2$ transporter and/or the heterologous polynucleotide encoding a rubrerythrin reductase.

An expression cassette comprising a heterologous polynucleotide encoding a SOR and/or a $CO_2$ transporter may be chimeric, meaning that at least one of its components is heterologous with respect to at least one of its other components. An expression cassette may also be one that is naturally occurring but has been obtained in a recombinant form useful for heterologous expression.

Any promoter useful for initiation of transcription in a cell of a plant, yeast or bacteria can be used in the expression cassettes of the present invention. A "promoter," as used herein, is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." A promoter can be identified in and isolated from the organism to be transformed and then inserted into the nucleic acid construct to be used in transformation of the organism.

The choice of promoter will vary depending on the temporal and spatial requirements for expression, and also depending on the host cell to be transformed. Thus, for example, expression of the heterologous polynucleotide encoding an archaeon SOR can be in any plant, plant part, (e.g., in leaves, in stalks or stems, in ears, in inflorescences (e.g. spikes, panicles, cobs, etc.), in roots, seeds and/or seedlings, and the like), plant cells (including algae cells), yeast cells, or bacterial cells. For example, in the case of a multicellular organism such as a plant where expression in a specific tissue or organ is desired, a tissue-specific or tissue preferred promoter can be used (e.g., a root specific/preferred promoter). In contrast, where expression in response to a stimulus is desired a promoter inducible by stimuli or chemicals can be used. Where continuous expression at a relatively constant level is desired throughout the cells or tissues of an organism a constitutive promoter can be chosen.

Thus, promoters useful with the invention include, but are not limited to, those that drive expression of a nucleotide sequence constitutively, those that drive expression when induced, and those that drive expression in a tissue- or developmentally-specific manner These various types of promoters are known in the art. Promoters can be identified in and isolated from the plant, yeast, or bacteria to be transformed and then inserted into the expression cassette to be used in transformation of the plant, yeast, or bacteria.

Non-limiting examples of a promoter include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5459252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J* 5:451-458; and Rochester et al. (1986) *EMBO J* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J* 10:2605-2612).

Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the polypeptides of the invention to be synthesized only when, for example, a crop of plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters useful with plants are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid (e.g., the PR1a system), steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) Genetics 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In some particular embodiments, promoters useful with algae include, but are not limited to, the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)), the promoter of the $\sigma^{70}$-type plastid rRNA gene (Prrn), the promoter of the psbA gene (encoding the photosystem-II reaction center protein D1) (PpsbA), the promoter of the psbD gene (encoding the photosystem-II reaction center protein D2) (PpsbD), the promoter of the psaA gene (encoding an apoprotein of photosystem I) (PpsaA), the promoter of the ATPase alpha subunit gene (PatpA), and promoter of the RuBisCo large subunit gene (PrbcL), and any combination thereof (See, e.g., De Cosa et al. *Nat. Biotechnol.* 19:71-74 (2001); Daniell et al. *BMC Biotechnol.* 9:33 (2009); Muto et al. *BMC Biotechnol.* 9:26 (2009); Surzycki et al. *Biologicals* 37:133-138 (2009)).

In some embodiments, promoters useful with bacteria and yeast include, but are not limited to, a constitutive promoter (e.g., lpp (lipoprotein gene)) and/or an oxidative stress inducible promoter (e.g., a superoxide dismutase or a catalase promoter).

Thus, in some embodiments, a promoter useful with yeast can include, but is not limited to, a promoter from phosphoglycerate kinase (PGK), glyceraldehyde-3-phosphate dehydrogenase (GAP), triose phosphate isomerase (TPI), galactose-regulon (GAL1, GAL10), alcohol dehydrogenase (ADH1, ADH2), phosphatase (PHOS), copper-activated metallothionine (CUP1), MFα1, PGK/α2 operator, TPI/α2 operator, GAP/GAL, PGK/GAL, GAP/ADH2, GAP/PHOS, iso-1-cytochrome c/glucocorticoid response element (CYC/GRE), phosphoglycerate kinase/angrogen response element (PGK/ARE), transcription elongation factor EF-1α (TEF1), triose phosphate dehydrogenase (TDH3), phosphoglycerate kinase 1 (PGK1), pyruvate kinase 1 (PYK1), and/or hexose transporter (HXT7) (See, Romanos et al. *Yeast* 8:423-488 (1992); and Partow et al. *Yeast* 27:955-964 (2010)).

In additional embodiments, a promoter useful with bacteria can include, but is not limited to, L-arabinose inducible (araBAD, $P_{BAD}$) promoter, any lac promoter, L-rhamnose inducible (rhaP$_{BAD}$) promoter, T7 RNA polymerase promoter, trc promoter, tac promoter, lambda phage promoter ($P_L$-9G-50), anydrotetracycline-inducible (tetA) promoter, trp, lpp, phoA, recA, pro U, cst-1, cadA, nar, lpp-lac, cspA, T7-lac operator, T3-lac operator, T4 gene 32, T5-lac operator, nprM-lac operator, Vhb, Protein A, corynebacterial-*E. coli* like promoters, thr, horn, diphtheria toxin promoter, sig A, sig B, nusG, SoxS, katb, α-amylase (Pamy), Ptms, P43 (comprised of two overlapping RNA polymerase a factor recognition sites, σA, σB), Ptms, P43, rplK-rplA, ferredoxin promoter, and/or xylose promoter. (See, K. Terpe *Appl. Microbiol, Biotechnol.* 72:211-222 (2006); Hannig et al. Trends in Biotechnology 16:54-60 (1998); and Srivastava Protein Expr Purif 40:221-229 (2005)).

In addition to promoters operably linked to a heterologous polynucleotide encoding an archaeal SOR (e.g., a *P. furiosus* SOR, SEQ ID NO:1, SEQ ID NO:2)), and promoters operably linked to a heterologous polynucleotide encoding a $CO_2$ transporter (e.g., SEQ ID NO:58, SEQ ID NO:60, SEQ ID NO:62) an expression cassette also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, translation termination sequences, and polyadenylation signal sequences, as described herein.

Thus, in some embodiments of the present invention, the expression cassettes can include at least one intron. An intron useful with this invention can be an intron identified in and isolated from a plant, yeast, or bacteria to be transformed and then inserted into the expression cassette to be used in transformation of the plant, yeast, or bacteria. As would be understood by those of skill in the art, the introns as used herein comprise the sequences required for self excision and are incorporated into the nucleic acid constructs in frame. An intron can be used either as a spacer to separate multiple protein-coding sequences in one nucleic acid construct, or an intron can be used inside one protein-coding sequence to stabilize the mRNA. If they are used within a protein-coding sequence, they are inserted "in-frame" with the excision sites included.

Non-limiting examples of introns useful with the present invention can be introns from the RuBisCO small subunit (rbcS) gene, the RuBisCO large subunit (rbcL) gene, the actin gene, the nitrate reductase gene (nr), the duplicated carbonic anhydrase gene 1 (Tdca1), the psbA gene, the atpA gene, or any combination thereof.

In some embodiments of the invention, an expression cassette can comprise an enhancer sequence. Enhancer sequences can be derived from, for example, any intron from any highly expressed gene. In particular embodiments, an enhancer sequence usable with this invention includes, but is not limited to, the nucleotide sequence of ggagg (e.g., ribosome binding site).

An expression cassette also can optionally include a transcriptional and/or translational termination region (i.e., termination region) that is functional in plants, yeast or bacteria. A variety of transcriptional terminators are available for use in expression cassettes and are responsible for the termination of transcription beyond the heterologous polynucleotide of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, the nucleotide sequence of interest, the host cell, or any combination thereof). Non-limiting examples of transcriptional terminators useful for plants can be a CAMV 35S terminator, a tml terminator, a nopaline synthase terminator and/or a pea rbcs E9 terminator, a RubisCo small subunit gene 1 (TrbcS1) terminator, an actin gene (Tactin) terminator, a nitrate reductase gene (Tnr) terminator, and/or a duplicated carbonic anhydrase gene 1 (Tdca1) terminator.

Further non-limiting examples of terminators useful with this invention for expression of SOR or other heterologous polynucleotides in algae include a terminator of the psbA gene (TpsbA), a terminator of the psaA gene (encoding an apoprotein of photosystem I) (TpsaA), a terminator of the psbD gene (TpsbD), a RuBisCo large subunit terminator (TrbcL), a terminator of the $\sigma^{70}$-type plastid rRNA gene (Trrn), and/or a terminator of the ATPase alpha subunit gene (TatpA).

Non-limiting examples of terminators for use with bacteria can be from trp, hom-trpB, lysA, thrB, and/or sodA.

An expression cassette of the invention also can include a nucleotide sequence for a selectable marker, which can be used to select a transformed plant, plant part, plant cell, yeast cell or bacteria cell. As used herein, "selectable marker" means a nucleotide sequence that when expressed imparts a distinct phenotype to a plant, plant part, plant cell, yeast cell or bacterial cell expressing the marker and thus allows such a transformed plant, plant part, plant cell, yeast cell or bacterial cell to be distinguished from that which does not have the marker. Such a nucleotide sequence may encode either a selectable or screenable marker, depending on whether the marker confers a trait that can be selected for by chemical means, such as by using a selective agent (e.g., an antibiotic, herbicide, or the like), or whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding aadA (i.e., spectinomycin and streptomycin resistance), a nucleotide sequence encoding neo (i.e., kanamycin resistance), a nucleotide sequence encoding aphA6 (i.e., kanamycin resistance), a nucleotide sequence encoding nptll (i.e., kanamycin resistance), a nucleotide sequence encoding bar (i.e., phosphinothricin resistance), a nucleotide sequence encoding cat (i.e., chloramphenicol resistance), a nucleotide sequence encoding badh (i.e., betaine aldehyde resistance), a nucleotide sequence encoding egfp, (i.e., enhanced green fluorescence protein), a nucleotide sequence encoding gfp (i.e., green fluorescent protein), a nucleotide sequence encoding mCherry (mCherry or red fluorescent protein), a nucleotide sequence encoding luc (i.e., luciferase), a nucleotide sequence encoding ble (bleomycin resistance), a nucleotide sequence encoding ereA (erythromycin resistance), and any combination thereof.

Further examples of selectable markers useful with the invention include, but are not limited to, a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No.

154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding Bla that confers ampicillin resistance; or a nucleotide sequence encoding aequorin which may be employed in calcium-sensitive bioluminescence detection (Prasher et al. (1985) *Biochem. Biophys. Res. Comm.* 126:1259-1268), and/or any combination thereof. In some embodiments, an expression cassette can further encode green fluorescent protein (GFP). One of skill in the art is capable of choosing a suitable selectable marker for use in an expression cassette of this invention.

An expression cassette comprising a heterologous polynucleotide encoding a SOR and an expression cassette comprising a heterologous polynucleotide encoding a $CO_2$ transporter and a SOR also can include polynucleotides that encode other desired traits. Such desired traits can be polynucleotides which confer high light tolerance, increased drought tolerance, increased flooding tolerance, increased tolerance to soil contaminants, increased CO2 uptake, increased CO2 assimilation, modification of carbon flux, increased yield, modified fatty acid composition of the lipids, increased oil production in seed, increased and modified starch production in seeds, increased and modified protein production in seeds, modified tolerance to herbicides and pesticides, production of terpenes, increased seed number, increased biomass of the roots, increased and/or modified biomass of the stem (trees), increased and/or modified biomass of the leaves, reduced photorespiration, and/or other desirable traits for agriculture or biotechnology.

Such polynucleotides can be stacked with any combination of nucleotide sequences to create plants, plant parts, plant cells, yeast cells or bacterial cells having the desired phenotype. Stacked combinations can be created by any method including, but not limited to, any conventional methodology (e.g., cross breeding for plants), or by genetic transformation. If stacked by genetic transformation, nucleotide sequences encoding additional desired traits can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

By "operably linked" or "operably associated," it is meant that the indicated elements are functionally related to each other, and are also generally physically related. Thus, the term "operably linked" or "operably associated" as used herein, refers to nucleotide sequences on a single nucleic acid molecule that are functionally associated. Therefore, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

Methods for detecting and quantifying ROS or oxidized cell components are well known in the art and include, but are not limited to: the nitroblue tetrazolium assay (Fryer et al. *J Exp Bot* 53: 1249-1254 (2002); Fryer et al. *Plant J* 33: 691-705 (2003)) and acridan lumigen PS-3 assay (Uy et al. *Journal of Biomolecular Techniques* 22:95-107 (2011) for detection of superoxide; the ferrous ammonium sulfate/xylenol orange (FOX) method (Wolff, *Methods Enzymol* 233: 182-189 (1994); Im et al. *Plant Physiol* 151:893-904 (2009)) for detection of peroxide; the 3,3-Diaminobenzidine (DAB) assay (Thordal-Christensen et al. *Plant J* 11(6): 1187-1194 (1997); the thiobarbituric acid assay (TBA) (Draper and Hadley, *Methods Enzymol* 186:421-431 (1990); Hodges et al. *Planta* 207: 604-611 (1999)) and the mass spectrometric determination of peroxidated lipids (Deighton et al. *Free Radic Res* 27: 255-265 (1997)) for detection of lipid peroxidation; the assay for 8-hydroxy-2'-deoxyguanosine in DNA (Bialkowski and Olinski, *Acta Biochim Pol* 46: 43-49 (1999)) for the detection of nucleic acid oxidation; and the reaction of oxidized protein with 2,4-dinitrophenylhydrazine (DPNH) (Levine et al. Methods Enzymol 233:346-357 (1994)) for detection of protein oxidation.

Methods for measuring photorespiration are known in the art. Thus, photorespiration can be indirectly measured by changes in the $CO_2$-saturation curve using fluorescence and gas exchange measurements (e.g., LiCOR) or via $^{18}O_2$ incorporation. Alternatively, determining the ratio of serine to glycine in actively photosynthesizing leaves can be used to measure photorespiration. Other ways that changes in photorespiration can be shown include comparing biomass productivity or photosynthesis under different $CO_2:O_2$ environments. See, e.g., Hideg et al. *Plant and Cell Physiology* 49: 1879-1886 (2008); and Berry et al. *Plant Physiol* 62:954-967 (1978).

Photosynthetic efficiency is the fraction of light energy converted into chemical energy during photosynthesis. Saturating pulse fluorescence measurements can be used to measure photosynthetic efficiency. $CO_2$ and $O_2$ exchange methods can also be used. A number of plant and algae studies have been done, which demonstrate that photosynthetic efficiency decreases when plants are exposed to ROS (Ganesh et al. *Biotechnol Bioeng* 96(6):1191-8 (2007); Zhang and Xing. *Plant Cell Physiology* 49(7):1092-1111 (2008).

Reactive oxygen species (ROS) are generated in the cells of aerobic organisms during normal metabolic processes and have been identified to have an important role in cell signaling and homeostasis. However, high levels of ROS can be detrimental to an organism's cell structure and metabolism often resulting in cell death (i.e., oxidative stress). Most organisms have endogenous mechanisms for protecting them from potential damage by ROS, including enzymes such as superoxide dismutase, catalase and peroxide, and small antioxidant molecules. However, under conditions of abiotic stress, the levels of ROS can rise significantly making the endogenous protective mechanisms insufficient. By stably introducing a heterologous polynucleotide encoding SOR from an archaeon species into the cells of plants, bacteria and yeast as described herein, said plants, yeasts and bacteria stably expressing the SOR have increased tolerance to the environmental stresses that induce ROS production.

"Abiotic stress" or "environmental stress" as used herein means any outside, nonliving, physical or chemical factors or conditions that induce ROS production. Thus, in some embodiments of the invention, an abiotic or environmental stress can include, but is not limited to, high heat, high light, ultraviolet radiation, high salt, drought, ozone, heavy metals, pesticides, herbicides, toxins, and/or anoxia (i.e., root flooding).

Parameters for the abiotic stress factors are species specific and even variety specific and therefore vary widely according to the species/variety exposed to the abiotic stress. Thus, for example, while one species may be severely impacted by a high temperature of 23° C., another species may not be impacted until at least 30° C., and the like. Temperatures above 30° C. result in, for example, dramatic reductions in the yields of many plant crops including algae. This is due to reductions in photosynthesis that begin at approximately 20-25° C., and the increased carbohydrate demands of crops growing at higher temperatures. The critical temperatures are not absolute, but vary depending upon such factors as the acclimatization of the organism to prevailing environmental conditions. In addition, because organisms are often exposed to multiple abiotic stresses at one time, the interaction between the stresses affects the response. For example, damage to a plant from excess light occurs at lower light intensities as temperatures increase beyond the photosynthetic optimum. Water stressed plants are less able to cool overheated tissues due to reduced transpiration, further exacerbating the impact of excess (high) heat and/or excess (high) light intensity. Thus, the particular parameters for high/low temperature, light intensity, drought and the like, which can negatively impact an organism will vary with species, variety, degree of acclimatization and the exposure to a combination of environmental conditions.

Any plant (or groupings of plants, for example, into a genus or higher order classification) can be employed in practicing the present invention including an angiosperm, a gymnosperm, a monocot, a dicot, a C3, C4, CAM plant, a microalgae, and/or a macroalgae.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, trichomes, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell.

In some embodiments of this invention, a plant, plant part or plant cell can be from a genus including, but not limited to, the genus of *amelina, Glycine, Sorghum, Brassica, Allium, Armoracia, Poa, Agrostis, Lolium, Festuca, Calamogrostis, Deschampsia, Spinacia, Beta, Pisum, Chenopodium, Helianthus, Pastinaca, Daucus, Petroselium, Populus, Prunus, Castanea, Eucalyptus, Acer, Quercus, Salix, Juglans, Picea, Pinus, Abies, Lemna, Wolffia, Spirodela, Oryza, Zea* or *Gossypium*.

In other embodiments, a plant, plant part or plant cell can be from a species including, but not limited to, the species of *Camelina alyssum* (Mill.) Thell., *Camelina microcarpa* Andrz. ex DC., *Camelina rumelica* Velen., *Camelina sativa* (L.) Crantz, *Sorghum* bicolor (e.g., *Sorghum* bicolor L. Moench), *Gossypium hirsutum, Glycine max, Zea mays Brassica oleracea, Brassica rapa, Brassica napus, Raphanus sativus, Armoracia rusticana, Allium sative, Allium cepa, Populus grandidentata, Populus tremula, Populus tremuloides, Prunus serotina, Prunus pensylvanica, Castanea dentate, Populus balsamifer, Populus deltoids, Acer Saccharum, Acer nigrum, Acer negundo, Acer rubrum, Acer saccharinum, Acer pseudoplatanus* or *Oryza sativa*. In additional embodiments, the plant, plant part or plant cell can be, but is not limited to, a plant of, or a plant part, or plant cell from wheat, barley, oats, turfgrass (bluegrass, bentgrass, ryegrass, fescue), feather reed grass, tufted hair grass, spinach, beets, chard, quinoa, sugar beets, lettuce, sunflower (*Helianthus annuus*), peas (*Pisum sativum*), parsnips (*Pastinaca sativa*), carrots (*Daucus carota*), parsley (*Petroselinum crispum*), duckweed, pine, spruce, fir, eucalyptus, oak, walnut, or willow. In particular embodiments, the plant, plant part and/or plant cell can be from *Camelina sativa*. In other particular embodiments, the plant, plant part and/or plant cell is not from *Arabidopsis thaliana*. In some representative embodiments, the plant, plant part, and/or plant cell is *camelina*, wheat, rice, corn, rape, canola, soybean, sorghum, or cotton.

In further embodiments, a plant and/or plant cell can be an algae or algae cell from a class including, but not limited to, the class of Bacillariophyceae (diatoms), Haptophyceae, Phaeophyceae (brown algae), Rhodophyceae (red algae) or Glaucophyceae (red algae). In still other embodiments, a plant and/or plant cell can be an algae or algae cell from a genus including, but not limited to, the genus of *Achnanthidium, Actinella, Nitzschia, Nupela, Geissleria, Gomphonema, Planothidium, Halamphora, Psammothidium, Navicula, Eunotia, Stauroneis, Chlamydomonas, Dunaliella, Nannochloris, Nannochloropsis, Scenedesmus, Chlorella, Cyclotella, Amphora, Thalassiosira, Phaeodactylum, Chrysochromulina, Prymnesium, Thalassiosira, Phaeodactylum, Glaucocystis, Cyanophora, Galdieria*, or *Porphyridium*. Additional nonlimiting examples of genera and species of diatoms useful with this invention are provided by the US Geological Survey/Institute of Arctic and Alpine Research at westerndiatoms.colorado.edu/species.

Any bacterium can be employed in practicing the present invention. In particular embodiments, a bacterial cell can be from a phylum that includes, but not limited to, the phylum of Cyanobacteria or can be from a genus including, but not limited to, the genus of *Bacillus, Lactobacillus, Lactococcus, Streptococcus, Pseudomonas, Corynebacterium, Escherichia* or *Clostridium*. In some embodiments, a bacterial cell can be *Escherichia coli*.

Further, any yeast in which heterologous expression of a SOR is useful can be used with the methods of this invention. In some representative embodiments, a yeast cell can be from a genus including, but not limited to, the genus of *Saccharomyces, Saccharomycodes, Kluyveromyces, Pichia, Candida, Zygosaccharomyces* or *Hanseniaspora*. In other embodiments, a yeast cell can be from a species including, but not limited to, the species of *Saccharomyces cerevisiae, S. uvarum* (carlsbergensis), *S. diastaticus, Saccharomycodes ludwigii, Kluyveromyces marxianus, Pichia pastoris, Candida stellata, C. pulcherrima, Zygosaccharomyces fermentati*, or *Hanseniaspora uvarum*.

As described herein, the present invention provides methods for increasing disease resistance (e.g., decrease disease symptoms and/or decreased pathogen growth and reproduction) in a plant, plant cell, or plant part, comprising: introducing into a plant, plant cell, or plant part a heterologous polynucleotide encoding a superoxide reductase from an archaeon species to produce a stably transformed plant, plant cell, or plant part, thereby producing a plant, plant part, or plant cell having increased disease resistance as compared to a control (e.g., a plant, plant part or plant cell that does not comprise said heterologous polynucleotide encoding a superoxide reductase from an archaeon species).

In some embodiments, the diseases for which an increase in resistance (or a decrease in disease symptoms/decreased pathogen growth and/or reproduction) can be observed include, but are not limited to, fungal diseases, bacterial diseases, and/or viral disease. Non-limiting examples of diseases include powdery mildew (*Erysiphe* spp.), damping off (*Rhizoctonia solani*), leaf blotch (*Mycosphaerella* spp), rust (*Puccinia* spp), leaf mold (*Cladosporium* spp.), soft rot (*Rhizopus* spp.), wilt (*Fusarium* spp.), coffee rust (*Haemelia vastatrix*) and/or *Pseudomonas* spp.

In some embodiments, the plant (and plant part or plant cell therefrom) and the disease for which increased resistance can be observed can include, but is not limited to, *Camelina sativa* and *Erysiphe* spp.; coffee rust and coffee; tomato and potato and potato blight; wheat and leaf rust; tomato and leaf mold; sweet potato and soft rot; corn, sorghum and soybean and charcoal rot; onion and white rot; cucurbit and downy mildew; wheat and black stem rust; and the like.

In representative embodiments, the plant (and plant part or plant cell therefrom) and the disease for which increased resistance can be observed can include, but is not limited to, those provided in Table 3.

TABLE 3

Exemplary diseases

| Disease | Pathogen | Host |
| --- | --- | --- |
| Powdery mildew | *Blumeria graminis* | Kentucky blue grass, fine fescue, perennial rye grass |
| Brown patch | *Rhizoctonia solani* | Tall fescue |
| Gray leaf spot | *Magnaporthe grisea* | Tall fescue |
| Leaf Spot | *Bipolaris* spp. or *Drechslera* spp | Bluegrasses, bermudagrass, fescues or perennial ryegrass |
| Gray Leaf Spot | (*Pyricularia grisea*) | Centipedegrass, Perennial ryegrass, St. Augustinegrass or tall fescue |
| Rust | *Puccinia* spp | Bermudagrass, bluegrasses, fescues, ryegrasses or zoysiagrass |
| Southern leaf blight | *Cochliobolus heterostrophus* | Maize |
| Blight | *Cercospora* spp | Tobacco, sugarbeet, Maize, |
| Blast | *Magnaporthe oryzae* | Rice |
| Wilt | *Fusarium oxysporum* | Tomato and other crops |

Any nucleotide sequence to be transformed into a plant, plant part, plant cell, yeast cell or bacterial cell can be modified for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications for the nucleotide sequences for selection are determined by comparing the species specific codon usage table with the codons present in the native nucleotide sequences. In those embodiments in which each of codons in native nucleotide sequence for selection are sufficiently used, then no modifications are needed (e.g., a frequency of more than 30% for a codon used for a specific amino acid in that species would indicate no need for modification). In other embodiments, wherein up to 3 nucleotides have to be modified in the nucleotide sequence, site-directed mutagenesis can be used according to methods known in the art (Zheng et al. *Nucleic Acids Res.* 32:e115 (2004); Dammai, *Meth. Mol. Biol* 634: 111-126 (2010); Davis and Vierstra. *Plant Mol. Biol.* 36(4): 521-528 (1998)). In still other embodiments, wherein more than three nucleotide changes are necessary, a synthetic nucleotide sequence can be generated using the same codon usage as the highly expressed genes that were used to develop the codon usage table.

The term "transformation" as used herein refers to the introduction of a heterologous polynucleotide into a cell.

Transformation of a plant, plant part, plant cell, yeast cell and/or bacterial cell may be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols that are well known in the art.

A heterologous polynucleotide encoding a SOR from an archaeon species as described herein and/or fragments thereof, and/or any combination thereof, can be introduced into the cell of a plant, yeast or bacteria by any method known to those of skill in the art. In some embodiments of the invention, transformation of a cell comprises nuclear transformation. In other embodiments, transformation of a cell comprises plastid transformation (e.g., chloroplast transformation).

Procedures for transforming plants, yeast and bacteria are well known and routine in the art and are described throughout the literature. Non-limiting examples of transformation methods include transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Mild et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)). General guides to the transformation of yeast include Guthrie and Fink (1991) (Guide to yeast genetics and molecular biology. In *Methods in Enzymology*, (Academic Press, San Diego) 194:1-932) and guides to methods related to the transformation of bacteria include Aune and Aachmann (*Appl. Microbiol Biotechnol* 85:1301-1313 (2010)).

A polynucleotide therefore can be introduced into a plant, plant part, plant cell, yeast cell and/or bacterial cell in any number of ways that are well known in the art. The methods of the invention do not depend on a particular method for introducing one or more nucleotide sequences into a plant, only that they gain access to the interior of the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant, bacteria or yeast, as part of a breeding protocol.

In some embodiments, when a plant part or plant cell is stably transformed, it can then be used to regenerate a stably transformed plant comprising the heterologous polynucleotide encoding a SOR from an archaeon species in its genome. Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

The regenerated plants are transferred to standard soil conditions and cultivated in a conventional manner. The plants are grown and harvested using conventional procedures.

The particular conditions for transformation, selection and regeneration of a plant can be optimized by those of skill in the art. Factors that affect the efficiency of transformation include the species of plant, the target tissue or cell, composition of the culture media, selectable marker genes, kinds of vectors, and light/dark conditions. Therefore, these and other factors may be varied to determine an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Further, the genetic properties engineered into the transgenic seeds and plants, plant parts, and/or plant cells of the present invention described herein can be passed on by sexual reproduction or vegetative growth and therefore can be maintained and propagated in progeny plants. Generally, maintenance and propagation make use of known agricultural methods developed to fit specific purposes such as harvesting, sowing or tilling.

In addition to the stably transformed plants, plant parts, plant cells, yeast and bacterial cells provided herein, the invention further provides products produced from said stably transformed plant, plant cell, plant part, yeast cell or bacterial cell of the invention. In some embodiments, the product produced can include but is not limited to biofuel, food, drink, animal feed, fiber, commodity chemicals, cosmetics and/or pharmaceuticals.

Additionally provided herein are seeds produced from the stably transformed plants of the invention, wherein said seeds comprise in their genome a heterologous polynucleotide encoding a SOR from an archaeon species. In other embodiments, the invention provides seeds produced from the stably transformed plants and comprising in their genome a heterologous polynucleotide encoding a SOR and a heterologous polynucleotide encoding a rubrerythrin reductase from an archaeon species. In further embodiments, seeds produced from the stably transformed plants and comprising in their genome a heterologous polynucleotide encoding a SOR from an archaeon species and a heterologous polynucleotide encoding a $CO_2$ transporter are provided. In still further embodiments, seeds produced from the stably transformed plants and comprising in their genome a heterologous polynucleotide encoding a SOR from an archaeon species, a heterologous polynucleotide encoding a $CO_2$ transporter and a heterologous polynucleotide encoding a rubrerythrin reductase from an archaeon species are provided.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "gene" refers to a nucleic acid molecule capable of being used to produce mRNA, anti-sense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

As used herein, the terms "fragment" when used in reference to a polynucleotide will be understood to mean a nucleic acid molecule or polynucleotide of reduced length relative to a reference nucleic acid molecule or polynucleotide and comprising, consisting essentially of and/or consisting of a nucleotide sequence of contiguous nucleotides identical or almost identical (e.g., 80%, 81%, 82%, 83%, 84%, 85%, R6%, 87%, 88%, 89%, 90%, 91%, 92%, 93%, 94%, 95%, 96%, 97%, 98%, 99% identical) to the reference nucleic acid or nucleotide sequence. Such a nucleic acid fragment according to the invention may be, where appropriate, included in a larger polynucleotide of which it is a constituent.

As used herein, a "functional" polypeptide or "functional fragment" is one that substantially retains at least one biological activity normally associated with that polypeptide. In particular embodiments, the "functional" polypeptide or "functional fragment" substantially retains all of the activities possessed by the unmodified peptide. By "substantially retains" biological activity, it is meant that the polypeptide retains at least about 50%, 55%, 60%, 65%, 70%, 75%, 80%, 85%, 90%, 95%, 96%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Thus, for example, a functional fragment of an archaeon SOR polypeptide is a polypeptide that retains at least 50% or more SOR activity or a functional fragment of a $CO_2$ transporter polypeptide is a polypeptide that retains at least 50% or more $CO_2$ transporter activity.

An "isolated" nucleic acid molecule or nucleotide sequence or nucleic acid construct or double stranded RNA molecule of the present invention is generally free of nucleotide sequences that flank the nucleic acid of interest in the genomic DNA of the organism from which the nucleic acid was derived (such as coding sequences present at the 5' or 3' ends). However, the nucleic acid molecule of this invention can include some additional bases or moieties that do not deleteriously or materially affect the basic structural and/or functional characteristics of the nucleic acid molecule.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose. In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

As used herein, "complementary" polynucleotides are those that are capable of hybridizing via base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely or fully complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules either along the full length of the molecules or along a portion or region of the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least at about 50%, 60%, 70%, 80% or 90% of their nucleotides. In some embodiments, the two nucleic acid sequences can be complementary at least at about 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

As used herein, "heterologous" refers to a nucleic acid molecule or nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous polynucleotide includes a nucleotide sequence derived from and inserted into the same natural, original cell type, but which is present in a non-natural state, e.g. present in a different copy number, and/or under the control of different regulatory sequences than that found in the native state of the nucleic acid molecule.

As used herein, the terms "transformed" and "transgenic" refer to any plant, plant part, plant cell, yeast cell or bacterial cell that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "transgene" as used herein, refers to any nucleotide sequence used in the transformation of an organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic yeast, or transgenic bacterium, is an organism into which a transgene has been delivered or introduced and the transgene can be expressed in the transgenic organism to produce a product, the presence of which can impart an effect and/or a phenotype in the organism.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 65%, 70%, 75%, 80%, 85%, 90% or 95% sequence identity. In some embodiments, the two nucleotide sequences can have at least 80%, 85%, 90%, 91%, 92%, 93%, 94%, 95%, 96%, 97%, 98%, 99% or 100% sequence identity. Thus, for example, a homolog of a SOR from an archaeon species of this invention or a homolog of a $CO_2$ transporter of this invention can have at least about 65%, 70%, 75%, 80%, 85%, 90%, 91%, 92%, 93%, 94%, 95%, 96%, 97%, 98%, 99% or 100% sequence identity to said SOR (see, e.g., Table 1) or said aquaporin of this invention, respectively. In representative embodiments, an SOR useful with this invention can have about 80%, 85%, 90%, 91%, 92%, 93%, 94%, 95%, 96%, 97%, 98%, 99% or 100% sequence identity to a nucleotide sequence encoding a *P. furiosus* SOR polynucleotide (e.g., SEQ ID NO:1 or SEQ ID NO:2). In other embodiments, an SOR useful with this invention can have about 80%, 85%, 90%, 91%, 92%, 93%, 94%, 95%, 96%, 97%, 98%, 99% or 100% sequence identity to a *P. furiosus* SOR polypeptide encoded by the amino acid sequence of SEQ ID NO:3 or SEQ ID NO:4.

Two nucleotide sequences can also be considered to be substantially complementary when the two sequences hybridize to each other under stringent conditions. A non-limiting example of "stringent" hybridization conditions include conditions represented by a wash stringency of 50% formamide with 5×Denhardt's solution, 0.5% SDS and 1×SSPE at 42° C. "Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). In some representative embodiments, two nucleotide sequences considered to be substantially complementary hybridize to each other under highly stringent conditions. Generally, highly stringent hybridization and wash conditions are selected to be about 5° C. lower than the thermal melting point ($T_m$) for the specific sequence at a defined ionic strength and pH.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in Guide to Huge Computers (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST®) programs which are publicly available from National Center Biotechnology Information (NCBI) at the National Library of Medicine, National Institute of Health. Bethesda, Md. 20894; see BLAST® Manual, Altschul, et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX® can be used to determine sequence identity; and for polynucleotide sequence BLASTN® can be used to determine sequence identity.

Accordingly, the present invention further provides nucleotide sequences having substantial sequence identity to the nucleotide sequences of the present invention (e.g., the polynucleotides encoding a SOR from an archaeon species or polynucleotides encoding a $CO_2$ transporter). Substantial sequence similarity or identity means at least 70%, 75%, 80%, 81%, 82%, 83%, 84%, 85%, 86%, 87%, 88%, 89%, 90%, 91%, 92%, 93%, 94%, 95%, 96%, 97%, 98%, 99% and/or 100% similarity or identity with another nucleotide sequence.

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1

Plants

Plants are continually challenged by environmental stresses that result in increased production of reactive oxygen species (ROS, e.g., superoxide and hydrogen peroxide). ROS can induce a switch from primary to secondary metabolism and can ultimately lead to plant tissue death. Like other aerobic organisms, plants have ROS scavenging enzymes, such as superoxide dismutase (SOD), peroxidase and catalases that help prevent the production and buildup of toxic free radicals.

*Pyrococcus furiosus* is an extremophilic (hyperthermophile) species of archaea with optimum growth at 100° C. It is found in hydrothermal vents and is a strict anaerobe. *P. furiosus* uses superoxide reductase (SOR—functional range of 4-100° C.) rather than SOD to deal with ROS. Unlike SOD, the endogenous plant enzyme, SOR is more efficient in removing ROS and does so without producing oxygen (i.e. reducing the potential for further ROS generation). Thus, for example, transformation of a plant to express an archaeon SOR in the chloroplast can assist in the reduction of ROS, thereby protecting the transgenic plant's photosynthetic reaction centers, lowering $O_2$ content, which in turn helps to reduce photorespiration, and reduce expression of defense mechanisms that diminish photosynthetic electron flux.

*Camelina sativa* plants stably transformed with a heterologous polynucleotide encoding a *P. furiosus* SOR and expressing the SOR in the chloroplasts are assessed for protection of the photosynthetic apparatus and its surrounding membrane lipids from oxidative damage, reduced photosynthetic electron flux, and increased tolerance to abiotic stresses (e.g., drought, heat, high light). Transgenic plants in which SOR is targeted to the chloroplast, mitochondria, peroxisome, and/or cytosolic membrane are assessed for delayed senescence and increased abiotic stress tolerance and biomass production. Transgenic plants expressing *P. furiosus* SOR in cell walls are assessed for reduction in lignin polymerization and for an increased accessibility of cell wall cellulose to at least one cell wall degrading enzyme such as cellulase and hemicellulase. Exemplary vectors for transformation of plants are provided in FIG. 1.

Example 2

Yeast

Figure 2:
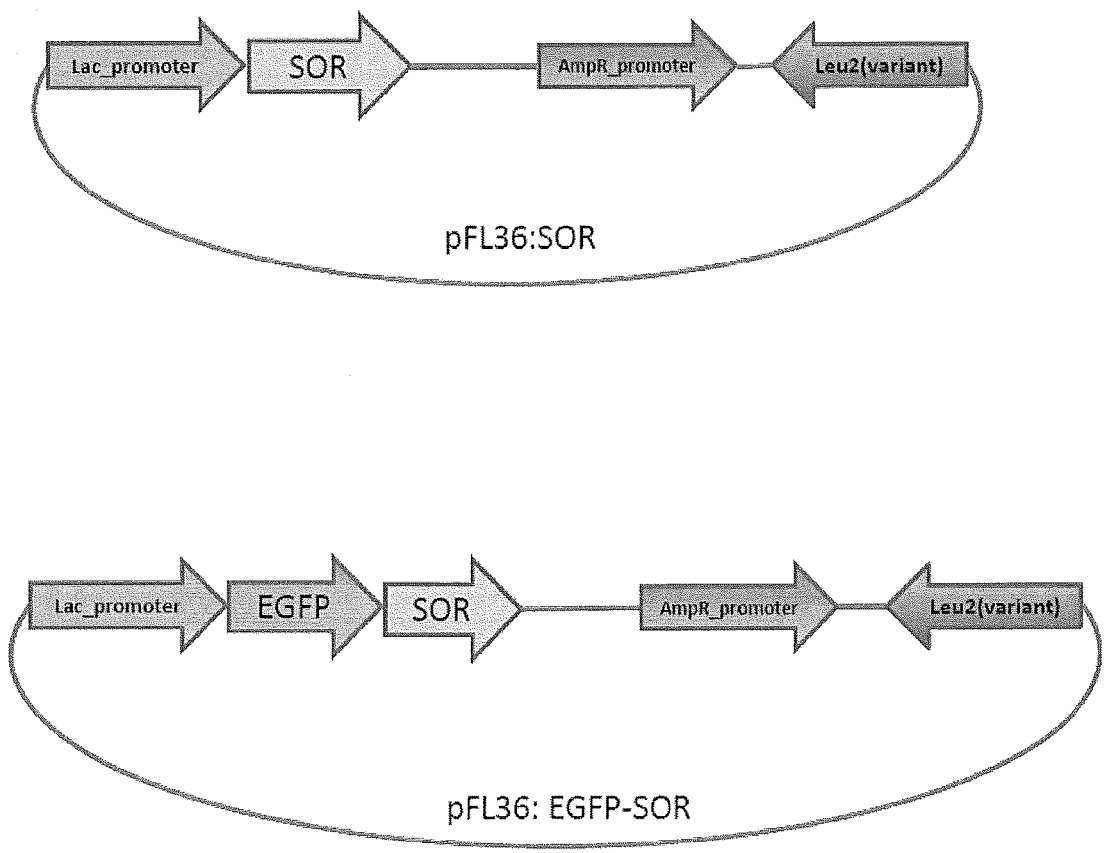
FIG. 2 shows vector maps of constructs for yeast transformation: pFL36:SOR and pFL36: EGFP-SOR

Industrial yeast strains generate reactive oxygen species (ROS, e.g., superoxide and hydrogen peroxide) in response to fermentation product accumulation and metabolic flux. ROS can oxidatively damage cellular components and can ultimately lead to cell death. Like other facultative aerobic organisms, yeast have ROS scavenging enzymes, such as superoxide dismutase (SOD), peroxidase and catalases that help prevent the production and buildup of toxic free radicals. However, transformation of yeast with archaeal SOR (targeted to the mitochondria, cytosol or as a membrane associated protein) would help further protect yeast from the ROS generated by metabolic flux and fermentation product buildup (ex. ethanol). Exemplary vectors for transformation of yeast are provided in FIG. 2.

Example 3

Bacteria

Industrial bacterial strains, such as those used for biofuel production (cyanobacteria, *E. coli, Clostridium*), generate ROS in response to metabolic flux and biofuel molecule accumulation. ROS can irreversibly damage bacterial macromolecules and cell structures and can ultimately lead to bacterial cell death. Transformation of bacteria with archaeal SOR (targeted either to the cytosol, to the periplasm, or as a membrane-associated protein) would aid in protecting the bacterial cells from ROS generated by metabolic flux and biofuel molecule accumulation. In some embodiments, when the SOR to be expressed in a bacterial cell is targeted to the periplasm, the periplasmic targeting protein can be encoded by the nucleotide sequence of atgaaacagagcaccattgcgaaagcgaaaaaaccgctgctgtttaccccggtgaccaaagcg (SEQ ID NO:52) or the amino acid sequence of MKQSTIAKAKKPLLFTPVTKA (SEQ ID NO:48).

Example 4

Preparation of *P. furiosus* Superoxide Reductase Polynucleotide for Plant Transformation The gene encoding *P. furiosus* superoxide reductase (SOR) was amplified using polymerase chain reaction (PCR), pfu DNA polymerase and the indicated primers (forward primers; 5'-CAC CAT GAT TAG TGA AAC CAT AAG-3' (SEQ ID NO:53) for cloning into pENTR/D/TOPO and 5'-ATG ATT AGT GAA ACC ATA AG-3' (SEQ ID NO:54) for cloning into pCR8/GW/TOPO) and reverse primer; 5'-TCA CTC TAA AGT GAC TTC GTT TTC-3', SEQ ID NO:55) to amplify the coding region of SOR. The resulting amplification product was subcloned into pENTR/D/TOPO and pCR8/GW/TOPO entry vectors (Invitrogen, Carlsbad, Calif.) and then into pEG100, pEG103 and pEG104 destination vectors (Functional Genomics Division of the Department of Plant Systems Biology, Gent, Belgium) using LR recombination reactions according to the manufacturer's instructions (Invitrogen).

The Resulting Constructs were as Follows:
pEG103:SOR—C terminal GFP
pEG104:SOR—N terminal YFP
pEG100:SOR—no tags
pEG100:EGFP-SOR—N terminal fusion with EGFP These above constructs enabled production of green fluorescence protein (GFP)-fusion-SOR proteins under the control of a CaMV 35S promoter in plants. Recombinant plasmids were transformed into *Agrobacterium tumefaciens* GV3101 using electroporation and then transformed into *Camelina* by vacuum infiltration of the inflorescences (Lu et al. *Plant Cell Reports* 27:273-278 (2008)). Four independent transformed lines were further selected. Stable expression of the transgene was monitored by RT-PCR and immunoblotting as described below.

SOR Nucleotide and Amino Acid Sequences:
(1) Nucleotide sequence of *P. furiosus* SOR: SEQ ID NO:1.
(2) Amino acid sequence of *P. furiosus* SOR:

```
                                          (SEQ ID NO: 3)
Met I S E T I R S G D W K G E K H V P V I E Y E R

E G E L V K V K Q V G K E I P H P N T T E H H I

R Y I E L Y F L P E G E N F V Y Q V G R V E F T A

H G E S V N G P N T S D V Y T E P I A Y F V L K T

K K K G K L Y A L S Y C N I H G L W E N E V T L E

Stop
```

(3) Nucleotide sequence of *P. furiosus* SOR variant: SEQ ID NO:2.

(4) Amino acid sequence of *P. furiosus* SOR variant:

```
                                          (SEQ ID NO: 4)
Met I S E T I R S G D W K G E K H V P V I E Y E R

E G E L V K V K V Q V G K E I P H P N T T E H H I

R Y I E L Y F L P E G E N F V Y Q V G R V E F T A

H G E S V N G P N T S D V Y T E P I A Y F V L K T

K K K G K L Y A L S D C N I H G L W E N E V T L E

Stop
```

Targeting Sequences:
(1) Chloroplast signal sequence: amino acid sequence of SEQ ID NO:5; nucleotide sequence of SEQ ID NO:6.
(2) Mitochondrial signal sequence: amino acid sequence of SEQ ID NO:7 or 9; nucleotide sequence of SEQ ID NO:8 or 10.
(3) Cell wall signal sequence: amino acid sequence of SEQ ID NO:11; nucleotide sequence of SEQ ID NO:12.
(4) Peroxisome signal sequence: amino acid sequence of SEQ ID NO:13; amino acid sequence of SEQ ID NO:14; nucleotide sequence of SEQ ID NO:15; amino acid sequence of SKL or nucleotide sequence of agcaaactg.
(5) Dual signal sequence for mitochondria and chloroplast: amino acid sequence of SEQ ID NO:16; nucleotide sequence of SEQ ID NO:17.

Vectors for Plant Transformation
(1) Exemplary constructs for chloroplast targeting
(A) Chloroplast targeted SOR (pEG100:CTP-SOR): amino acid sequence of SEQ ID NO:18; nucleotide sequence of SEQ ID NO:19.
(B) Chloroplast targeted SOR with EGFP as N terminal fusion pEG100:CTP-EGFP-SOR nucleotide sequence (chloroplast targeting peptide-enhanced green fluorescent protein-superoxide reductase (CTP-EGFP-SOR)): amino acid sequence of SEQ ID NO:20; nucleotide sequence of SEQ ID NO:21.
(C) pEG100:CTP-SOR-EGFP Sequence: amino acid sequence of SEQ ID NO:22; nucleotide sequence of SEQ ID NO:23.
(D) Chloroplast targeted SOR with yellow fluorescent protein (YFP) as N terminal fusion (CTP-YFP-SOR amino acid sequence): amino acid sequence of SEQ ID NO:24; nucleotide sequence of SEQ ID NO:25.

Maps of exemplary vectors for chloroplast transformation are provided in FIGS. 1A-C (pEG100:CTP-SOR, pEG100:CTP-EGFP-SOR, and pEG100:CTP-SOR-EGFP, respectively). In each case, the vector includes Bar as a selection marker, 35S as the promoter, attR sites, the 3' sequences of the octapine synthase gene (OCS).

Example 5

*Camelina sativa* Transformation with Chloroplast Targeted SOR Sequences

*Agrobacterium*-mediated transformation was used to introduce the *P. furiosus* SOR into the chloroplasts, mitochondria, peroxisomes, and/or cell walls of *C. sativa* plants. Constructs are provided in Table 4.

TABLE 4

Constructs used in transformation of Camelina.

| Construct | NOTES | Entry vector | Destination vector |
|---|---|---|---|
| 35S: SOR-GFP | GFP on C terminus | pCR8/GW/TOPO | pEG103→35S-GW-GFP-OCS-3' |
| 35S:YFP-SOR | YFP on N terminus | pCR8/GW/TOPO | pEG104→35S-YFP-GW-OCS-3' |
| 35S:eGFP-SOR | eGFP on N terminus | pENTR/D/TOPO | pEG100→35S-GW-OCS-3' |
| 35S: CTP-SOR | No tags | pCR8/GW/TOPO | pEG100→35S-GW-OCS-3' |
| 35S: SOR | No tags | pENTR:SOR | pEG100→35S-GW-OCS-3' |
| 35S: CTP-egfp-SOR | CTP is in the N terminal side for targeting to chloroplasts | pCR8/GW/TOPO | pEG100→35S-GW-OCS-3' |

Protocol for Transforming *Camelina*
Luria Broth (LB) medium for growing *Agrobacterium*
Infiltration medium:
 1/2× MS salts
 5% (w/v)Sucrose
 0.044 uM BAP
 0.05% Silwet L-77

Procedure:
(1) Two days prior to transformation, a pre-culture of *Agrobacterium* carrying the appropriate binary vector is prepared by inoculating the *Agrobacterium* onto 3 ml LB medium including suitable antibiotics and incubating the culture at 28° C.
(2) One day prior to transformation a larger volume of (150 ml-300 ml) LB medium is inoculated with at least 1 ml of the preculture and incubated at 28° C. for about 16-24 hrs.
(3) Water plants prior to transformation.
(4) On the day of transformation of the plant, *Agrobacterium* cells are pelleted by centrifugation at 6000 rpm for 10 min at room temperature (e.g., about 19° C. to about 24° C.).
(5) The pellet is resuspended in 300-600 ml of infiltration medium (note: the infiltration medium is about double the volume used in the agro culture (about 150-300 ml)).
(6) The suspension solution is transferred to an open container that can hold the volume of infiltration medium prepared (300-600 ml) in which plants can be dipped and which fits into a desiccator.
(7) Place the container from (6) into a desiccator, invert a plant and dip the inflorescence shoots into the infiltration medium.
(8) Connect the desiccator to a vacuum pump and evacuate for 5 min at 16-85 kPa.
(9) Release the vacuum slowly.
(10) After releasing vacuum, remove the plants and orient them into an upright position or on their sides in a plastic nursery flat, and place a cover over them for the next 24 hours.
(11) The next day, the cover is removed, the plants rinsed with water and returned to their normal growing conditions (e.g., of about 22° C./18° C. (day/night) with daily watering under about 250-400 µE white light).
(12) A week later the plants were transformed again, repeating steps 1-11.
(13) The plants were watered on alternate days beginning after transformation for about 2-3 weeks and then twice a week for about another 2 weeks after which they were watered about once a week for about another 2-3 weeks for drying.

Example 6

Camelina sativa Transformation with Sequences Targeted to Mitochondria, Cell Wall, Cytosolic Membrane, and/or Peroxisome (1) Exemplary targeting sequences for mitochondrial targeting: amino acid sequence of SEQ ID NO:26; nucleotide sequence of SEQ ID NO:27.
(2) Exemplary targeting sequences for cell wall targeting: amino acid sequence of SEQ ID NO:28; nucleotide sequence of SEQ ID NO:29.
(3) Exemplary targeting sequences for peroxisomal targeting.
(A) At the N terminus: amino acid sequence of SEQ ID NO:30; nucleotide sequence of SEQ ID NO:31.
(B) At the C terminus: amino acid sequence of SEQ ID NO:32; nucleotide sequence of SEQ ID NO:33.
(4) Exemplary targeting sequences for targeting to the cytosolic membrane: CVVQ (SEQ ID NO:34); tgtgtcgtgcag (SEQ ID NO:35) SOR plus the targeting target peptide sequence: amino acid sequence of SEQ ID NO:36; nucleotide sequence of SEQ ID NO:37.

The general motif for prenylation or farnesylation is C-terminal CaaX box motif on target proteins. C=cysteine; a=aliphatic amino acid; x=any amino acid. For plants, this motif most often is CVVQ (SEQ ID NO:34). This motif is required for specific posttranslational modifications (i.e. prenylation, farnesylation) that target the protein for association with the cytosolic side of the plasma membrane (the "inner" cytosolic side of the cell) or the cytosolic side of the nuclear membrane.

(5) Exemplary construct for targeting to the mitochondria and chloroplast: amino acid sequence of SEQ ID NO:38; nucleotide sequence of SEQ ID NO:39.

Example 7

Analysis of Transformed C. sativa Plants (1) Verification of expression in the various plant organelles RT-PCR and pRT-PCR Methods.

RNA is isolated using the RNeasy kit (Qiagen), with an additional DNase I treatment to remove contaminating genomic DNA. Reverse transcription (RT) was carried out to generate cDNA using Omniscript reverse transcriptase enzyme (Qiagen). GFP-fused-SOR transcripts can be detected by PCR as described by Im et al., (2005) using internal GFP forward and gene specific primers (SOR reverse and actin specific primers), APX specific primers described in (Panchuk et al. *Plant Physiol* 129: 838-853 (2002) and Zat12 specific primers (forward; 5' AACACAAACCACAAGAGGATCA 3', SEQ ID NO:56, and reverse; 5' CGTCAACGTTTTCTTGTCCA 3', SEQ ID NO:57). Quantitative RT-PCR was carried out using Full Velocity SYBR-Green® QPCR Master Mix (Stratagene) on a MX3000P thermocycler (Stratagene). Gene specific primers for select genes were designed with the help of AtRTPrimer, a database for generating specific RT-PCR primer pairs (Han and Kim, *BMC Bioinformatics* 7:179 (2006)). Relative gene expression data were generated using the $2^{-\Delta\Delta Ct}$ method (Livak and Schmittgen, *Methods* 25:402-408 (2001)) using the wild-type zero time point as the reference. PCR conditions were 1 cycle of 95° C. for 10 min, 95° C. for 15 s, and 60° C. for 30 s to see the dissociation curve, 40 cycles of 95° C. for 1 minute for DNA denaturation, and 55° C. for 30 s for DNA annealing and extension.

Immunoblotting (Western analysis for SOR detection)

Total protein extract is obtained from liquid $N_2$ frozen plants or seedlings grown as described by Weigel and Glazebrook, *Arabidopsis: A Laboratory Manual*. Cold Spring Harbor Laboratory Press, Cold Spring Harbor, N.Y. (2002)). Protein concentration is quantified as described by Bradford (*Anal Biochem* 72: 248-254, (1976)). Protein is separated by 10% (w/v) SDS-PAGE and detected with rabbit antibodies raised against *P. furiosus* SOR (at 1:2,000 dilution) or antibodies raised against HSP70, BiP, and CRT (at 1:1,000 dilution). Immunoreactivity is visualized with either horseradish peroxidase-conjugated anti-rabbit or anti-mouse antibodies (Pierce, Rockford, Ill.).

SOR Activity Assay

Samples are ground with liquid nitrogen and lysed as described previously (Im et al., *FEBS Lett* 579: 5521-5526 (2005)). Samples are centrifuged at 27,000 g at 4° C. for 30 min and resulting supernatants are passed through a 0.45 micron filter unit to remove cellular debris. Extracts are dialyzed overnight in 50 mM phosphate buffer. To reduce plant SOD background activity of dialyzed samples, samples are heat-treated (heat-treated at 80° C. for 15 min) and centrifuged at 21,000 g for 15 min. The heat treatments used are sufficient to inactivate some endogenous plant SOD activity, allowing for greater discrimination between SOD and SOR activity in the transgenic plants. To avoid leaf pigments and reduce loss of activity resulting from dialysis, roots are harvested from seedlings grown for 28 days or 42 days on agar plates in a growth chamber (8 h light/16 h dark).

The standard SOD/SOR assay is performed as described in Im et al. (*FEBS Lett* 579: 5521-5526 (2005)). One unit of SOD/SOR activity is defined as the amount of enzyme that inhibits the rate of reduction of cytochrome c by 50% (McCord and Fridovich, *J Biol Chem* 244: 6049-6055 (1969)).

(2) Reduction in ROS $H_2O_2$ Measurements (FOX Assay)

A ferrous ammonium sulfate/xylenol orange (FOX) method is used to quantify $H_2O_2$ in plant extracts (Wolff, *Methods Enzymol* 233: 182-189, 1994)). The original FOX method is modified by addition of an acidification step where 1 ml of 25 mM $H_2SO_4$ was added to each sample to allow for precipitation of interfering substances (sugars, starches, polysaccharides) for 15 min on ice, and centrifuged at 9,700 g, for 15 min, at 4° C. The cell free extract is collected and passed through a 0.45 µm-filter unit. 100 µl is added to 1 ml of the FOX reagent, mixed, and incubated at room temperature for 20 min The concentration of $H_2O_2$ in the reagent is calibrated using absorbance at 240 nm and an extinction coefficient of 43.6 $M^{-1}$ $cm^{-1}$. The concentration of $H_2O_2$ is measured in nmoles $H_2O_2$ per gram of fresh wt cells.

Ascorbate Peroxidase (APX) Activity Assay

APX activity is determined as described previously (Nakano and Asada, *Plant Cell Physiol* 22:867-880, 1981). Fifty µg of the extract is used in a 3 ml APX assay and the reaction proceeds for 2 minutes. APX activity is expressed as µmol of ascorbate oxidized $(mg\ protein)^{-1}\ min^{-1}$. Additional confirmation of APX activity can be done by an in-gel assay as described by Panchuk et al. (*Plant Physiol* 129: 838-853 (2002)).

(3) Protection of the Photosynthetic Apparatus and its Surrounding Membrane Lipids To quantify the protection of the photosystems, leaf fluorescence and CO2 fixation rates of fully expanded leaves is measured using a LiCOR system. The maximal photochemical efficiency of the PSII is calculated using the ratio $F_v/F_m$, where $F_v=F_m-F_o$ (Genty et al., *Biochimica et Biophysica Acta* (BBA)–*General Subjects* 990: 87-92 (1989)). This is calculated from initial ($F_o$) and maximum fluorescence ($F_m$) as measured in vivo on the last fully expanded leaf pre-acclimatized to the dark for approximately 40 min. $F_m$ can be estimated by applying a light saturating flash with an intensity of ca. 8,000 µmol photons $m^{-2}$ $s^{-1}$.

(4) Reduction in Photorespiration

Reduction in photorespiration is determined by $CO_2$ fixation rates as described above using a LICOR system. Plants are exposed to atmospheric $CO_2$:$O_2$ mixtures (400 ppm $CO_2$/21% $O_2$) or at saturating $CO_2$ concentrations (4000 ppm/21% $O_2$) and their biomass, photosynthetic $CO_2$ fixation rates, chlorophyll fluorescence and chlorophyll content are quantified. Higher $CO_2$ fixation rates in the transgenic plants under limiting $CO_2$ compared to wild type and control plants indicate reduced photorespiratory activity.

(5) Increased Disease Resistance

Transgenic *Camelina sativa* plants comprising a heterologous polynucleotide encoding SOR from *P. furiosus* (e.g., SEQ ID NO:1, SEQ ID NO:2) were challenged with powdery mildew (*Eryisyphe cichoracearum*). 3,3-Diamino benzidine (DAB) staining method was used for in situ detection of hydrogen peroxide in the powdery mildew infected leaves (Thordal-Christensen et al. *Plant J* 11(6): 1187-1194 (1997)). DAB is prepared in water and protected from light. The two youngest leaves per plant and two plants per line (of the drought treated plants) were selected for the assay (WT, CS 9-5, CS 10-4). Once the leaves were harvested from the plant, they are placed in the DAB solution upright such that the petiole is in the solution and vacuum infiltrated for 5 min. The multiwell plate with leaves in DAB solution is placed in a low light area. After 6 hrs of DAB treatment, the leaves were bleached in 95% ethanol for 2 hrs and then boiled in ethanol for 10 min. and then imaged.

Figure 3:
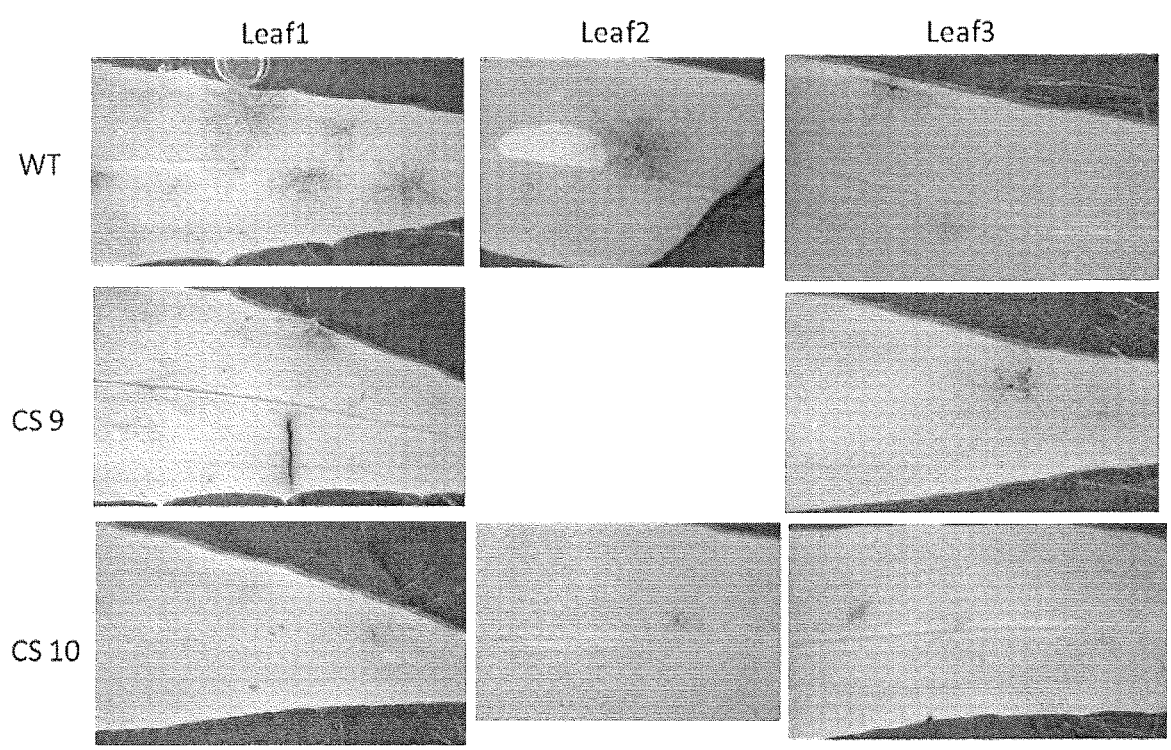
FIG. 3 shows images of leaves of wild type (WT) and transgenic plants challenged with powdery mildew spores.

Results are shown in FIG. 3. For the purpose of imaging the leaves were infiltrated with DAB. Leaves of WT and two of the transgenic CTP-SOR plants were excised and treated with a solution of DAB for 6 hrs and assayed. Brown staining on the leaves is due to the formation of a brown polymerization product when $H_2O_2$ reacts with DAB. Powdery mildew lesions can be seen as brown haustoria on the leaves. FIG. 3 shows that the transgenic plants inoculated with the powdery mildew had increased resistance (showed reduced growth of the pathogen on the plant and reduced symptoms).

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

That which is claimed:

1. A method of increasing fungal disease resistance in a plant, plant cell, or plant part, the method comprising introducing into said plant, plant cell, or plant part a heterologous polynucleotide encoding a superoxide reductase from *Pyrococcus furiosus* to produce a stably transformed plant, plant cell, or plant part, thereby producing a plant, plant part, or plant cell having increased fungal disease resistance as compared to a control,
wherein the heterologous polynucleotide encoding the superoxide reductase from *Pyrococcus furiosus* is the nucleotide sequence of SEQ ID NO:1 and/or SEQ ID NO: 2, and/or encodes the amino acid sequence of SEQ ID NO:3 and/or SEQ ID NO:4.

2. The method of claim 1, wherein said superoxide reductase is expressed and localized to the chloroplast, the cell wall, mitochondria and/or as a membrane associated protein of said stably transformed plant, plant cell, or plant part.

* * * * *

UNITED STATES PATENT AND TRADEMARK OFFICE
CERTIFICATE OF CORRECTION

PATENT NO. : 10,526,615 B2
APPLICATION NO. : 15/836465
DATED : January 7, 2020
INVENTOR(S) : Grunden et al.

Page 1 of 1

It is certified that error appears in the above-identified patent and that said Letters Patent is hereby corrected as shown below:

On the Title Page

Item (56) References Cited, OTHER PUBLICATIONS, Page 4, Column 2, Line 19: Please correct "Voalker" to read -- Voelker --

In the Specification

Column 18, Line 67: Please correct "($P_L$-9G-50)" to read -- ($p_L$, $p_L$-9G-50) --

Column 30, Line 18: Please correct "R6%" to read -- 86% --

Signed and Sealed this
Twenty-second Day of September, 2020

Andrei Iancu
*Director of the United States Patent and Trademark Office*

SEQUENCE LISTING

```
<160> NUMBER OF SEQ ID NOS: 63

<210> SEQ ID NO 1
<211> LENGTH: 375
<212> TYPE: DNA
<213> ORGANISM: Pyrococcus furiosus

<400> SEQUENCE: 1
atgattagtg aaaccataag aagtggggac tggaaaggag aaaagcacgt ccccgttata    60
gagtatgaaa gagaagggga gcttgttaaa gttaaggtgc aggttggtaa agaaatcccg   120
catccaaaca ccactgagca ccacatcaga tacatagagc tttatttctt accagaaggt   180
gagaactttg tttaccaggt tggaagagtt gagtttacag ctcacggaga gtctgtaaac   240
ggcccaaaca cgagtgatgt gtacacagaa cccatagctt actttgtgct caagactaag   300
aagaagggca agctctatgc tcttagctac tgtaacatcc acggcctttg ggaaaacgaa   360
gtcactttag agtga                                                    375

<210> SEQ ID NO 2
<211> LENGTH: 375
<212> TYPE: DNA
<213> ORGANISM: Pyrococcus furiosus

<400> SEQUENCE: 2
atgattagtg aaaccataag aagtggggac tggaaaggag aaaagcacgt ccccgttata    60
gagtatgaaa gagaagggga gcttgttaaa gttaaggtgc aggttggtaa agaaatcccg   120
catccaaaca ccactgagca ccacatcaga tacatagagc tttatttctt accagaaggt   180
gagaactttg tttaccaggt tggaagagtt gagtttacag ctcacggaga gtctgtaaac   240
ggcccaaaca cgagtgatgt gtacacagaa cccatagctt actttgtgct caagactaag   300
aagaagggca agctctatgc tcttagcgac tgtaacatcc acggcctttg ggaaaacgaa   360
```
gtcactttag agtga                                         375

<210> SEQ ID NO 3
<211> LENGTH: 124
<212> TYPE: PRT
<213> ORGANISM: Pyrococcus furiosus

<400> SEQUENCE: 3

Met Ile Ser Glu Thr Ile Arg Ser Gly Asp Trp Lys Gly Glu Lys His
1               5                   10                  15

Val Pro Val Ile Glu Tyr Glu Arg Glu Gly Leu Val Lys Val Lys
            20                  25                  30

Val Gln Val Gly Lys Glu Ile Pro His Pro Asn Thr Thr Glu His His
        35                  40                  45

Ile Arg Tyr Ile Glu Leu Tyr Phe Leu Pro Glu Gly Glu Asn Phe Val
    50                  55                  60

Tyr Gln Val Gly Arg Val Glu Phe Thr Ala His Gly Glu Ser Val Asn
65                  70                  75                  80

Gly Pro Asn Thr Ser Asp Val Tyr Thr Glu Pro Ile Ala Tyr Phe Val
                85                  90                  95

Leu Lys Thr Lys Lys Lys Gly Leu Tyr Ala Leu Ser Tyr Cys Asn
            100                 105                 110

Ile His Gly Leu Trp Glu Asn Glu Val Thr Leu Glu
        115                 120

<210> SEQ ID NO 4
<211> LENGTH: 124
<212> TYPE: PRT
<213> ORGANISM: Pyrococcus furiosus

<400> SEQUENCE: 4

Met Ile Ser Glu Thr Ile Arg Ser Gly Asp Trp Lys Gly Glu Lys His
1               5                   10                  15

Val Pro Val Ile Glu Tyr Glu Arg Glu Gly Leu Val Lys Val Lys
            20                  25                  30

Val Gln Val Gly Lys Glu Ile Pro His Pro Asn Thr Thr Glu His His
        35                  40                  45

Ile Arg Tyr Ile Glu Leu Tyr Phe Leu Pro Glu Gly Glu Asn Phe Val
    50                  55                  60

Tyr Gln Val Gly Arg Val Glu Phe Thr Ala His Gly Glu Ser Val Asn
65                  70                  75                  80

Gly Pro Asn Thr Ser Asp Val Tyr Thr Glu Pro Ile Ala Tyr Phe Val
                85                  90                  95

Leu Lys Thr Lys Lys Lys Gly Lys Leu Tyr Ala Leu Ser Asp Cys Asn
            100                 105                 110

Ile His Gly Leu Trp Glu Asn Glu Val Thr Leu Glu
        115                 120

<210> SEQ ID NO 5
<211> LENGTH: 57
<212> TYPE: PRT
<213> ORGANISM: Nicotiana tabacum

<400> SEQUENCE: 5

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

```
Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 6
<211> LENGTH: 171
<212> TYPE: DNA
<213> ORGANISM: Nicotiana tabacum

<400> SEQUENCE: 6
atggcgagca gcgtgctgag cagcgcggcg gtggcgaccc gcagcaacgt ggcgcaggcg    60
aacatggtgg cgccgtttac cggcctgaaa agcgcggcga gctttccggt gagccgcaaa   120
cagaacctgg atattaccag cattgcgagc aacggcggcc gcgtgcagtg c            171

<210> SEQ ID NO 7
<211> LENGTH: 25
<212> TYPE: PRT
<213> ORGANISM: Saccharomyces cerevisiae

<400> SEQUENCE: 7

Met Leu Ser Leu Arg Gln Ser Ile Arg Phe Phe Lys Pro Ala Thr Arg
1               5                  10                  15

Thr Leu Cys Ser Ser Arg Tyr Leu Leu
            20                  25

<210> SEQ ID NO 8
<211> LENGTH: 75
<212> TYPE: DNA
<213> ORGANISM: Saccharomyces cerevisiae

<400> SEQUENCE: 8
atgctgagcc tgcgccagag cattcgcttt tttaaaccgg cgacccgcac cctgtgcagc    60
agccgctatc tgctg                                                     75

<210> SEQ ID NO 9
<211> LENGTH: 78
<212> TYPE: PRT
<213> ORGANISM: Arabidopsis thaliana

<400> SEQUENCE: 9

Met Tyr Leu Thr Ala Ser Ser Ala Ser Ser Ser Ile Ile Arg Ala
1               5                  10                  15

Ala Ser Ser Arg Ser Ser Ser Leu Phe Ser Phe Arg Ser Val Leu Ser
            20                  25                  30

Pro Ser Val Ser Ser Thr Ser Pro Ser Ser Leu Leu Ala Arg Arg Ser
        35                  40                  45

Phe Gly Thr Ile Ser Pro Ala Phe Arg Arg Trp Ser His Ser Phe His
    50                  55                  60

Ser Lys Pro Ser Pro Phe Arg Phe Thr Ser Gln Ile Arg Ala
65                  70                  75

<210> SEQ ID NO 10
<211> LENGTH: 234
<212> TYPE: DNA
<213> ORGANISM: Arabidopsis thaliana

<400> SEQUENCE: 10
atgtatctga ccgcgagcag cagcgcgagc agcagcatta ttcgcgcggc gagcagccgc    60
```

```
agcagcagcc tgtttagctt tcgcagcgtg ctgagcccga gcgtgagcag caccagcccg    120
agcagcctgc tggcgcgccg cagctttggc accattagcc cggcgtttcg ccgctggagc    180
catagctttc atagcaaacc gagcccgttt cgctttacca gccagattcg cgcg          234
```

<210> SEQ ID NO 11
<211> LENGTH: 26
<212> TYPE: PRT
<213> ORGANISM: Saccharomyces cerevisiae

<400> SEQUENCE: 11

Met Arg Ile Leu Pro Lys Ser Gly Gly Gly Ala Leu Cys Leu Leu Phe
1               5                   10                  15

Val Phe Ala Leu Cys Ser Val Ala His Ser
            20                  25

<210> SEQ ID NO 12
<211> LENGTH: 78
<212> TYPE: DNA
<213> ORGANISM: Saccharomyces cerevisiae

<400> SEQUENCE: 12

```
atgcgcattc tgccgaaaag cggcggcggc gcgctgtgcc tgctgtttgt gtttgcgctg    60
tgcagcgtgg cgcatagc                                                  78
```

<210> SEQ ID NO 13
<211> LENGTH: 9
<212> TYPE: PRT
<213> ORGANISM: Artificial
<220> FEATURE:
<223> OTHER INFORMATION: Consensus PTS-2 sequence
<220> FEATURE:
<221> NAME/KEY: misc_feature
<222> LOCATION: (3)..(7)
<223> OTHER INFORMATION: Xaa can be any naturally occurring amino acid

<400> SEQUENCE: 13

Arg Leu Xaa Xaa Xaa Xaa Xaa His Leu
1               5

<210> SEQ ID NO 14
<211> LENGTH: 10
<212> TYPE: PRT
<213> ORGANISM: Artificial
<220> FEATURE:
<223> OTHER INFORMATION: Peroxisome signal sequence

<400> SEQUENCE: 14

Met Arg Leu Ser Ile His Ala Glu His Leu
1               5                   10

<210> SEQ ID NO 15
<211> LENGTH: 30
<212> TYPE: DNA
<213> ORGANISM: Artificial
<220> FEATURE:
<223> OTHER INFORMATION: Peroxisome signal coding sequence

<400> SEQUENCE: 15

```
atgcgcctga gcattcatgc ggaacatctg                                     30
```

<210> SEQ ID NO 16
<211> LENGTH: 85
<212> TYPE: PRT

<213> ORGANISM: Arabidopsis thaliana

<400> SEQUENCE: 16

Met Leu Arg Thr Val Ser Cys Leu Ala Ser Arg Ser Ser Ser Leu
1               5                   10                  15

Phe Phe Arg Phe Phe Arg Gln Phe Pro Arg Ser Tyr Met Ser Leu Thr
            20                  25                  30

Ser Ser Thr Ala Ala Leu Arg Val Pro Ser Arg Asn Leu Arg Arg Ile
        35                  40                  45

Ser Ser Pro Ser Val Ala Gly Arg Arg Leu Leu Arg Arg Gly Leu
    50                  55                  60

Arg Ile Pro Ser Ala Ala Val Arg Ser Val Asn Gly Gln Phe Ser Arg
65                  70                  75                  80

Leu Ser Val Arg Ala
                85

<210> SEQ ID NO 17
<211> LENGTH: 255
<212> TYPE: DNA
<213> ORGANISM: Arabidopsis thaliana

<400> SEQUENCE: 17
atgctgcgca ccgtgagctg cctggcgagc cgcagcagca gcagcctgtt ttttcgcttt        60
tttcgccagt ttccgcgcag ctatatgagc ctgaccagca gcaccgcggc gctgcgcgtg       120
ccgagccgca acctgcgccg cattagcagc ccgagcgtgg cgggccgccg cctgctgctg       180
cgccgcggcc tgcgcattcc gagcgcggcg gtgcgcagcg tgaacggcca gtttagccgc       240
ctgagcgtgc gcgcg                                                        255

<210> SEQ ID NO 18
<211> LENGTH: 181
<212> TYPE: PRT
<213> ORGANISM: Artificial
<220> FEATURE:
<223> OTHER INFORMATION: Chloroplast targeted SOR sequence

<400> SEQUENCE: 18

Met Ala Ser Ser Val Leu Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys Met Ile Ser Glu Thr Ile Arg
    50                  55                  60

Ser Gly Asp Trp Lys Gly Glu Lys His Val Pro Val Ile Glu Tyr Glu
65                  70                  75                  80

Arg Glu Gly Glu Leu Val Lys Val Lys Val Gln Val Gly Lys Glu Ile
                85                  90                  95

Pro His Pro Asn Thr Thr Glu His His Ile Arg Tyr Ile Glu Leu Tyr
            100                 105                 110

Phe Leu Pro Glu Gly Glu Asn Phe Val Tyr Gln Val Gly Arg Val Glu
        115                 120                 125

Phe Thr Ala His Gly Glu Ser Val Asn Gly Pro Asn Thr Ser Asp Val
    130                 135                 140

Tyr Thr Glu Pro Ile Ala Tyr Phe Val Leu Lys Thr Lys Lys Lys Gly
145                 150                 155                 160

Lys Leu Tyr Ala Leu Ser Tyr Cys Asn Ile His Gly Leu Trp Glu Asn
                165                 170                 175

Glu Val Thr Leu Glu
            180

<210> SEQ ID NO 19
<211> LENGTH: 543
<212> TYPE: DNA
<213> ORGANISM: Artificial
<220> FEATURE:
<223> OTHER INFORMATION: Chloroplast targeted SOR coding sequence

<400> SEQUENCE: 19

```
atggcgagca gcgtgctgag cagcgcggcg gtggcgaccc gcagcaacgt ggcgcaggcg      60
aacatggtgg cgccgtttac cggcctgaaa agcgcggcga gctttccggt gagccgcaaa     120
cagaacctgg atattaccag cattgcgagc aacgcggcc gcgtgcagtg catgattagc     180
gaaaccattc gcagcggcga ttggaaaggc gaaaaacatg tgccggtgat tgaatatgaa     240
cgcgaaggcg aactggtgaa agtgaaagtg caggtgggca agaaattcc gcatccgaac     300 accaccgaac atcatattcg ctatattgaa ctgtattttc tgccggaagg cgaaaacttt     360
gtgtatcagg tgggccgcgt ggaatttacc gcgcatggcg aaagcgtgaa cggcccgaac     420
accagcgatg tgtataccga accgattgcg tattttgtgc tgaaaaccaa aaaaaaggc      480 aaactgtatg cgctgagcta ttgcaacatt catggcctgt gggaaaacga agtgaccctg     540
gaa                                                                   543
```

<210> SEQ ID NO 20
<211> LENGTH: 425
<212> TYPE: PRT
<213> ORGANISM: Artificial
<220> FEATURE:
<223> OTHER INFORMATION: Chloroplast targeted EGFP-SOR fusion protein
      sequence

<400> SEQUENCE: 20

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys Met Gln Met Val Ser Lys Gly
    50                  55                  60

Glu Glu Leu Phe Thr Gly Val Val Pro Ile Leu Val Glu Leu Asp Gly
65                  70                  75                  80

Asp Val Asn Gly His Lys Phe Ser Val Ser Gly Glu Gly Glu Gly Asp
                85                  90                  95

Ala Thr Tyr Gly Lys Leu Thr Leu Lys Phe Ile Cys Thr Thr Gly Lys
            100                 105                 110

Leu Pro Val Pro Trp Pro Thr Leu Val Thr Thr Leu Thr Tyr Gly Val
        115                 120                 125

Gln Cys Phe Ser Arg Tyr Pro Asp His Met Lys Gln His Asp Phe Phe
    130                 135                 140

Lys Ser Ala Met Pro Glu Gly Tyr Val Gln Glu Arg Thr Ile Phe Phe
145                 150                 155                 160

Lys Asp Asp Gly Asn Tyr Lys Thr Arg Ala Glu Val Lys Phe Glu Gly

```
                    165                 170                 175
Asp Thr Leu Val Asn Arg Ile Glu Leu Lys Gly Ile Asp Phe Lys Glu
                180                 185                 190

Asp Gly Asn Ile Leu Gly His Lys Leu Glu Tyr Asn Tyr Asn Ser His
            195                 200                 205

Asn Val Tyr Ile Met Ala Asp Lys Gln Lys Asn Gly Ile Lys Val Asn
        210                 215                 220

Phe Lys Ile Arg His Asn Ile Glu Asp Gly Ser Val Gln Leu Ala Asp
225                 230                 235                 240

His Tyr Gln Gln Asn Thr Pro Ile Gly Asp Gly Pro Val Leu Leu Pro
                245                 250                 255

Asp Asn His Tyr Leu Ser Thr Gln Ser Ala Leu Ser Lys Asp Pro Asn
            260                 265                 270

Glu Lys Arg Asp His Met Val Leu Leu Glu Phe Val Thr Ala Ala Gly
        275                 280                 285

Ile Thr Leu Gly Met Asp Glu Leu Tyr Lys Leu Ser Ser Met Ile Ser
    290                 295                 300

Glu Thr Ile Arg Ser Gly Asp Trp Lys Gly Glu Lys His Val Pro Val
305                 310                 315                 320

Ile Glu Tyr Glu Arg Glu Gly Leu Val Lys Val Lys Val Gln Val
                325                 330                 335

Gly Lys Glu Ile Pro His Pro Asn Thr Thr Glu His His Ile Arg Tyr
            340                 345                 350

Ile Glu Leu Tyr Phe Leu Pro Glu Gly Glu Asn Phe Val Tyr Gln Val
        355                 360                 365

Gly Arg Val Glu Phe Thr Ala His Gly Glu Ser Val Asn Gly Pro Asn
    370                 375                 380

Thr Ser Asp Val Tyr Thr Glu Pro Ile Ala Tyr Phe Val Leu Lys Thr
385                 390                 395                 400

Lys Lys Lys Gly Lys Leu Tyr Ala Leu Ser Tyr Cys Asn Ile His Gly
                405                 410                 415

Leu Trp Glu Asn Glu Val Thr Leu Glu
            420                 425

<210> SEQ ID NO 21
<211> LENGTH: 1269
<212> TYPE: DNA
<213> ORGANISM: Artificial
<220> FEATURE:
<223> OTHER INFORMATION: Chloroplast targeted EGFP-SOR fusion protein
      coding sequence

<400> SEQUENCE: 21
atggcttcct cagttctttc ctctgcagca gttgccaccc gcagcaatgt tgctcaagct    60
aacatggttg caccttttcac tggccttaag tcagctgcct cattccctgt ttcaaggaag   120
caaaaccttg acatcacttc cattgccagc aacggcggaa gagtgcaatg catgcagatg   180
gtgagcaagg gcgaggagct gttcaccggg gtggtgccca tcctggtcga gctggacggc   240
gacgtaaacg gccacaagtt cagcgtgtcc ggcgagggcg agggcgatgc cacctacggc   300
aagctgaccc tgaagttcat ctgcaccacc ggcaagctgc ccgtgccctg gcccaccctc   360
gtgaccaccc tgacctacgg cgtgcagtgc ttcagccgct accccgacca catgaagcag   420
cacgacttct tcaagtccgc catgcccgaa ggctacgtcc aggagcgcac catcttcttc   480
aaggacgacg gcaactacaa gacccgcgcc gaggtgaagt tcgagggcga caccctggtg   540
```

```
aaccgcatcg agctgaaggg catcgacttc aaggaggacg gcaacatcct ggggcacaag    600
ctggagtaca actacaacag ccacaacgtc tatatcatgg ccgacaagca gaagaacggc    660
atcaaggtga acttcaagat ccgccacaac atcgaggacg gcagcgtgca gctcgccgac    720
cactaccagc agaacacccc catcggcgac ggccccgtgc tgctgcccga caaccactac    780
ctgagcaccc agtccgccct gagcaaagac cccaacgaga gcgcgatca catggtcctg    840 ctggagttcg tgaccgccgc cgggatcact ctcggcatgg acgagctgta caagatgatt    900
agtgaaacca taagaagtgg ggactggaaa ggagaaaagc acgtccccgt tatagagtat    960
gaaagagaag gggagcttgt taaagttaag gtgcaggttg gtaaagaaat cccgcatcca   1020
aacaccactg agcaccacat cagatacata gagctttatt tcttaccaga aggtgagaac   1080 tttgttacc aggttggaag agttgagttt acagctcacg gagagtctgt aaacggccca   1140
aacacgagtg atgtgtacac agaacccata gcttactttg tgctcaagac taagaagaag   1200
ggcaagctct atgctcttag ctactgtaac atccacggcc tttgggaaaa cgaagtcact   1260
ttagagtga                                                           1269
```

<210> SEQ ID NO 22
<211> LENGTH: 422
<212> TYPE: PRT
<213> ORGANISM: Artificial
<220> FEATURE:
<223> OTHER INFORMATION: Chloroplast targeted SOR-EGFP fusion protein
      sequence

<400> SEQUENCE: 22

```
Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys Met Gln Met Ile Ser Glu Thr
    50                  55                  60

Ile Arg Ser Gly Asp Trp Lys Gly Glu Lys His Val Pro Val Ile Glu
65                  70                  75                  80

Tyr Glu Arg Glu Gly Glu Leu Val Lys Val Lys Val Gln Val Gly Lys
                85                  90                  95

Glu Ile Pro His Pro Asn Thr Thr Glu His His Ile Arg Tyr Ile Glu
            100                 105                 110

Leu Tyr Phe Leu Pro Glu Gly Glu Asn Phe Val Tyr Gln Val Gly Arg
        115                 120                 125

Val Glu Phe Thr Ala His Gly Glu Ser Val Asn Gly Pro Asn Thr Ser
    130                 135                 140

Asp Val Tyr Thr Glu Pro Ile Ala Tyr Phe Val Leu Lys Thr Lys Lys
145                 150                 155                 160

Lys Gly Lys Leu Tyr Ala Leu Ser Tyr Cys Asn Ile His Gly Leu Trp
                165                 170                 175

Glu Asn Glu Val Thr Leu Glu Met Val Ser Lys Gly Glu Glu Leu Phe
            180                 185                 190

Thr Gly Val Val Pro Ile Leu Val Glu Leu Asp Gly Asp Val Asn Gly
        195                 200                 205

His Lys Phe Ser Val Ser Gly Glu Gly Glu Gly Asp Ala Thr Tyr Gly
    210                 215                 220
```

```
Lys Leu Thr Leu Lys Phe Ile Cys Thr Thr Gly Lys Leu Pro Val Pro
225                 230                 235                 240

Trp Pro Thr Leu Val Thr Thr Leu Thr Tyr Gly Val Gln Cys Phe Ser
            245                 250                 255

Arg Tyr Pro Asp His Met Lys Gln His Asp Phe Phe Lys Ser Ala Met
        260                 265                 270

Pro Glu Gly Tyr Val Gln Glu Arg Thr Ile Phe Phe Lys Asp Asp Gly
    275                 280                 285

Asn Tyr Lys Thr Arg Ala Glu Val Lys Phe Glu Gly Asp Thr Leu Val
    290                 295                 300

Asn Arg Ile Glu Leu Lys Gly Ile Asp Phe Lys Glu Asp Gly Asn Ile
305                 310                 315                 320

Leu Gly His Lys Leu Glu Tyr Asn Tyr Asn Ser His Asn Val Tyr Ile
            325                 330                 335

Met Ala Asp Lys Gln Lys Asn Gly Ile Lys Val Asn Phe Lys Ile Arg
        340                 345                 350

His Asn Ile Glu Asp Gly Ser Val Gln Leu Ala Asp His Tyr Gln Gln
    355                 360                 365

Asn Thr Pro Ile Gly Asp Gly Pro Val Leu Leu Pro Asp Asn His Tyr
370                 375                 380

Leu Ser Thr Gln Ser Ala Leu Ser Lys Asp Pro Asn Glu Lys Arg Asp
385                 390                 395                 400

His Met Val Leu Leu Glu Phe Val Thr Ala Ala Gly Ile Thr Leu Gly
            405                 410                 415

Met Asp Glu Leu Tyr Lys
            420

<210> SEQ ID NO 23
<211> LENGTH: 1269
<212> TYPE: DNA
<213> ORGANISM: Artificial
<220> FEATURE:
<223> OTHER INFORMATION: Chloroplast targeted SOR-EGFP fusion protein
      sequence

<400> SEQUENCE: 23
atggcttcct cagttctttc ctctgcagca gttgccaccc gcagcaatgt tgctcaagct    60
aacatggttg cacctttcac tggccttaag tcagctgcct cattccctgt ttcaaggaag   120
caaaaccttg acatcacttc cattgccagc aacggcggaa gagtgcaatg catgcagatg   180
attagtgaaa ccataagaag tggggactgg aaaggagaaa agcacgtccc cgttatagag   240
tatgaaagag aaggggagct tgttaaagtt aaggtgcagg ttggtaaaga aatcccgcat   300
ccaaacacca ctgagcacca catcagatac atagagcttt atttcttacc agaaggtgag   360
aactttgttt accaggttgg aagagttgag tttacagctc acggagagtc tgtaaacggc   420
ccaaacacga gtgatgtgta cacagaaccc atagcttact ttgtgctcaa gactaagaag   480
aagggcaagc tctatgctct tagctactgt aacatccacg cctttgggaa aaacgaagtc   540
actttagagt gaatggtgag caagggcgag gagctgttca ccggggtggt gcccatcctg   600
gtcgagctgg acggcgacgt aaacggccac aagttcagcg tgtccggcga gggcgagggc   660
gatgccacct acggcaagct gaccctgaag ttcatctgca ccaccggcaa gctgcccgtg   720
ccctggccca cgctcgtgac caccctgacc tacggcgtgc agtgcttcag ccgctacccc   780
gaccacatga agcagcacga cttcttcaag tccgccatgc ccgaaggcta cgtccaggag   840
cgcaccatct tcttcaagga cgacggcaac tacaagaccc gcgccgaggt gaagttcgag   900
```

```
ggcgacaccc tggtgaaccg catcgagctg aagggcatcg acttcaagga ggacggcaac    960
atcctggggc acaagctgga gtacaactac aacagccaca cgtctatat catggccgac    1020 aagcagaaga acggcatcaa ggtgaacttc aagatccgcc acaacatcga ggacggcagc    1080
gtgcagctcg ccgaccacta ccagcagaac ccccccatcg gcgacggccc cgtgctgctg    1140
cccgacaacc actacctgag cacccagtcc gccctgagca agaccccaa cgagaagcgc    1200 gatcacatgg tcctgctgga gttcgtgacc gccgccggga tcactctcgg catggacgag    1260
ctgtacaag                                                              1269
```

<210> SEQ ID NO 24
<211> LENGTH: 419
<212> TYPE: PRT
<213> ORGANISM: Artificial
<220> FEATURE:
<223> OTHER INFORMATION: CHloroplast targeting YFP-SOR fusion protein sequence

<400> SEQUENCE: 24

```
Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys Met Gly Lys Gly Glu Glu Leu
    50                  55                  60

Phe Thr Gly Val Val Pro Ile Leu Val Glu Leu Asp Gly Asp Val Asn
65                  70                  75                  80

Gly His Lys Phe Ser Val Ser Gly Glu Gly Glu Gly Asp Ala Thr Tyr
                85                  90                  95

Gly Lys Leu Thr Leu Lys Phe Ile Cys Thr Thr Gly Lys Leu Pro Val
            100                 105                 110

Pro Trp Pro Thr Leu Val Thr Thr Phe Gly Tyr Gly Leu Gln Cys Phe
        115                 120                 125

Ala Arg Tyr Pro Asp His Met Lys Gln His Asp Phe Phe Lys Ser Ala
    130                 135                 140

Met Pro Glu Gly Tyr Val Gln Glu Arg Thr Ile Phe Phe Lys Asp Asp
145                 150                 155                 160

Gly Asn Tyr Lys Thr Arg Ala Glu Val Lys Phe Glu Gly Asp Thr Leu
                165                 170                 175

Val Asn Arg Ile Glu Leu Lys Gly Ile Asp Phe Lys Glu Asp Gly Asn
            180                 185                 190

Ile Leu Gly His Lys Leu Glu Tyr Asn Tyr Asn Ser His Asn Val Tyr
        195                 200                 205

Ile Met Ala Asp Lys Gln Lys Asn Gly Ile Lys Val Asn Phe Lys Ile
    210                 215                 220

Arg His Asn Ile Glu Asp Gly Ser Val Gln Leu Ala Asp His Tyr Gln
225                 230                 235                 240

Gln Asn Thr Pro Ile Gly Asp Gly Pro Val Leu Leu Pro Asp Asn His
                245                 250                 255

Tyr Leu Ser Tyr Gln Ser Ala Leu Ser Lys Asp Pro Asn Glu Lys Arg
            260                 265                 270

Asp His Met Val Leu Leu Glu Phe Val Thr Ala Ala Gly Ile Thr Leu
        275                 280                 285
```

Gly Met Asp Glu Leu Tyr Lys Met Ile Ser Glu Thr Ile Arg Ser Gly
    290                 295                 300

Asp Trp Lys Gly Glu Lys His Val Pro Val Ile Glu Tyr Glu Arg Glu
305                 310                 315                 320

Gly Glu Leu Val Lys Val Lys Val Gln Val Gly Lys Glu Ile Pro His
                325                 330                 335

Pro Asn Thr Thr Glu His His Ile Arg Tyr Ile Glu Leu Tyr Phe Leu
            340                 345                 350

Pro Glu Gly Glu Asn Phe Val Tyr Gln Val Gly Arg Val Glu Phe Thr
        355                 360                 365

Ala His Gly Glu Ser Val Asn Gly Pro Asn Thr Ser Asp Val Tyr Thr
    370                 375                 380

Glu Pro Ile Ala Tyr Phe Val Leu Lys Thr Lys Lys Gly Lys Leu
385                 390                 395                 400

Tyr Ala Leu Ser Tyr Cys Asn Ile His Gly Leu Trp Glu Asn Glu Val
                405                 410                 415

Thr Leu Glu

<210> SEQ ID NO 25
<211> LENGTH: 1257
<212> TYPE: DNA
<213> ORGANISM: Artificial
<220> FEATURE:
<223> OTHER INFORMATION: Chloroplast targeting YFP-SOR coding sequence

<400> SEQUENCE: 25
atggcgagca gcgtgctgag cagcgcggcg gtggcgaccc gcagcaacgt ggcgcaggcg     60
aacatggtgg cgccgtttac cggcctgaaa agcgcggcga gctttccggt gagccgcaaa    120
cagaacctgg atattaccag cattgcgagc aacggcggcc gcgtgcagtg catgggcaaa    180
ggcgaagaac tgtttaccgg cgtggtgccg attctggtgg aactggatgg cgatgtgaac    240
ggccataaat ttagcgtgag cggcgaaggc gaaggcgatg cgacctatgg caaactgacc    300
ctgaaattta tttgcaccac cggcaaactg ccggtgccgt ggccgaccct ggtgaccacc    360
tttggctatg gcctgcagtg ctttgcgcgc tatccggatc atatgaaaca gcatgatttt    420
tttaaaagcg cgatgccgga aggctatgtg caggaacgca ccatttttttt taaagatgat    480 ggcaactata aacccgcgc ggaagtgaaa tttgaaggcg ataccctggt gaaccgcatt    540
gaactgaaag gcattgattt taaagaagat ggcaacattc tgggccataa actggaatat    600
aactataaca gccataacgt gtatattatg gcggataaac agaaaaacgg cattaaagtg    660
aactttaaaa ttcgccataa cattgaagat ggcagcgtgc agctggcgga tcattatcag    720
cagaacaccc cgattggcga tggcccggtg ctgctgccgg ataaccatta tctgagctat    780
cagagcgcgc tgagcaaaga tccgaacgaa aaacgcgatc atatggtgct gctggaattt    840
gtgaccgcgg cgggcattac cctgggcatg atgaactgt ataaaatgat agcgaaacc    900 attcgcagcg gcgattggaa aggcgaaaaa catgtgccgg tgattgaata tgaacgcgaa    960
ggcgaactgg tgaaagtgaa agtgcaggtg ggcaaagaaa ttccgcatcc gaacaccacc   1020
gaacatcata ttcgctatat tgaactgtat tttctgccgg aaggcgaaaa ctttgtgtat   1080
caggtgggcc gcgtggaatt taccgcgcat ggcgaaagcg tgaacggccc gaacaccagc   1140
gatgtgtata ccgaaccgat tgcgtatttt gtgctgaaaa ccaaaaaaaa aggcaaactg   1200
tatgcgctga gctattgcaa cattcatggc ctgtgggaaa acgaagtgac cctggaa      1257

<210> SEQ ID NO 26
<211> LENGTH: 149
<212> TYPE: PRT
<213> ORGANISM: Artificial
<220> FEATURE:
<223> OTHER INFORMATION: Mitochondrial targeting SOR protein sequence

<400> SEQUENCE: 26

Met Leu Ser Leu Arg Gln Ser Ile Arg Phe Phe Lys Pro Ala Thr Arg
1               5                   10                  15

Thr Leu Cys Ser Ser Arg Tyr Leu Leu Met Ile Ser Glu Thr Ile Arg
            20                  25                  30

Ser Gly Asp Trp Lys Gly Glu Lys His Val Pro Val Ile Glu Tyr Glu
        35                  40                  45

Arg Glu Gly Glu Leu Val Lys Val Lys Val Gln Val Gly Lys Glu Ile
    50                  55                  60

Pro His Pro Asn Thr Thr Glu His His Ile Arg Tyr Ile Glu Leu Tyr
65                  70                  75                  80

Phe Leu Pro Glu Gly Glu Asn Phe Val Tyr Gln Val Gly Arg Val Glu
                85                  90                  95

Phe Thr Ala His Gly Glu Ser Val Asn Gly Pro Asn Thr Ser Asp Val
            100                 105                 110

Tyr Thr Glu Pro Ile Ala Tyr Phe Val Leu Lys Thr Lys Lys Gly
        115                 120                 125

Lys Leu Tyr Ala Leu Ser Tyr Cys Asn Ile His Gly Leu Trp Glu Asn
    130                 135                 140

Glu Val Thr Leu Glu
145

<210> SEQ ID NO 27
<211> LENGTH: 447
<212> TYPE: DNA
<213> ORGANISM: Artificial
<220> FEATURE:
<223> OTHER INFORMATION: Mitochondrial targeting SOR coding sequence

<400> SEQUENCE: 27
atgctgagcc tgcgccagag cattcgcttt tttaaaccgg cgacccgcac cctgtgcagc      60
agccgctatc tgctgatgat tagcgaaacc attcgcagcg gcgattggaa aggcgaaaaa     120
catgtgccgg tgattgaata tgaacgcgaa ggcgaactgg tgaaagtgaa agtgcaggtg     180
ggcaaagaaa ttccgcatcc gaacaccacc gaacatcata ttcgctatat tgaactgtat     240
tttctgccgg aaggcgaaaa ctttgtgtat caggtgggcc gcgtggaatt taccgcgcat     300
ggcgaaagcg tgaacggccc gaacaccagc gatgtgtata ccgaaccgat tgcgtatttt     360
gtgctgaaaa ccaaaaaaaa aggcaaactg tatgcgctga gctattgcaa cattcatggc     420
ctgtgggaaa acgaagtgac cctggaa                                         447

<210> SEQ ID NO 28
<211> LENGTH: 150
<212> TYPE: PRT
<213> ORGANISM: Artificial
<220> FEATURE:
<223> OTHER INFORMATION: Cell wall targeting SOR protein sequence

<400> SEQUENCE: 28

Met Arg Ile Leu Pro Lys Ser Gly Gly Gly Ala Leu Cys Leu Leu Phe
1               5                   10                  15

Val Phe Ala Leu Cys Ser Val Ala His Ser Met Ile Ser Glu Thr Ile
            20                  25                  30

Arg Ser Gly Asp Trp Lys Gly Glu Lys His Val Pro Val Ile Glu Tyr
        35                  40                  45

Glu Arg Glu Gly Glu Leu Val Lys Val Lys Val Gln Val Gly Lys Glu
    50                  55                  60

Ile Pro His Pro Asn Thr Thr Glu His His Ile Arg Tyr Ile Glu Leu
65                  70                  75                  80

Tyr Phe Leu Pro Glu Gly Glu Asn Phe Val Tyr Gln Val Gly Arg Val
                85                  90                  95

Glu Phe Thr Ala His Gly Glu Ser Val Asn Gly Pro Asn Thr Ser Asp
            100                 105                 110

Val Tyr Thr Glu Pro Ile Ala Tyr Phe Val Leu Lys Thr Lys Lys Lys
        115                 120                 125

Gly Lys Leu Tyr Ala Leu Ser Tyr Cys Asn Ile His Gly Leu Trp Glu
    130                 135                 140

Asn Glu Val Thr Leu Glu
145                 150

<210> SEQ ID NO 29
<211> LENGTH: 450
<212> TYPE: DNA
<213> ORGANISM: Artificial
<220> FEATURE:
<223> OTHER INFORMATION: Cell wall targeting SOR coding sequence

<400> SEQUENCE: 29
atgcgcattc tgccgaaaag cggcggcggc gcgctgtgcc tgctgtttgt gtttgcgctg     60
tgcagcgtgg cgcatagcat gattagcgaa accattcgca gcggcgattg gaaaggcgaa    120
aaacatgtgc cggtgattga atatgaacgc gaaggcgaac tggtgaaagt gaaagtgcag    180
gtgggcaaag aaattccgca tccgaacacc accgaacatc atattcgcta tattgaactg    240
tattttctgc cggaaggcga aaactttgtg tatcaggtgg gccgcgtgga atttaccgcg    300
catggcgaaa gcgtgaacgg cccgaacacc agcgatgtgt ataccgaacc gattgcgtat    360
tttgtgctga aaccaaaaaa aaaaggcaaa ctgtatgcgc tgagctattg caacattcat    420
ggcctgtggg aaaacgaagt gaccctggaa                                    450

<210> SEQ ID NO 30
<211> LENGTH: 134
<212> TYPE: PRT
<213> ORGANISM: Artificial
<220> FEATURE:
<223> OTHER INFORMATION: Peroxisomal targeting SOR protein sequence

<400> SEQUENCE: 30

Met Arg Leu Ser Ile His Ala Glu His Leu Met Ile Ser Glu Thr Ile
1               5                   10                  15

Arg Ser Gly Asp Trp Lys Gly Glu Lys His Val Pro Val Ile Glu Tyr
            20                  25                  30

Glu Arg Glu Gly Glu Leu Val Lys Val Lys Val Gln Val Gly Lys Glu
        35                  40                  45

Ile Pro His Pro Asn Thr Thr Glu His His Ile Arg Tyr Ile Glu Leu
    50                  55                  60

Tyr Phe Leu Pro Glu Gly Glu Asn Phe Val Tyr Gln Val Gly Arg Val
65                  70                  75                  80

Glu Phe Thr Ala His Gly Glu Ser Val Asn Gly Pro Asn Thr Ser Asp

```
                    85                  90                  95

Val Tyr Thr Glu Pro Ile Ala Tyr Phe Val Leu Lys Thr Lys Lys
                100                 105                 110

Gly Lys Leu Tyr Ala Leu Ser Tyr Cys Asn Ile His Gly Leu Trp Glu
        115                 120                 125

Asn Glu Val Thr Leu Glu
    130

<210> SEQ ID NO 31
<211> LENGTH: 402
<212> TYPE: DNA
<213> ORGANISM: Artificial
<220> FEATURE:
<223> OTHER INFORMATION: Peroxisomal targeting SOR coding sequence

<400> SEQUENCE: 31
atgcgcctga gcattcatgc ggaacatctg atgattagcg aaaccattcg cagcggcgat      60
tggaaaggcg aaaaacatgt gccggtgatt gaatatgaac gcgaaggcga actggtgaaa     120
gtgaaagtgc aggtgggcaa agaaattccg catccgaaca ccaccgaaca tcatattcgc     180
tatattgaac tgtattttct gccggaaggc gaaaactttg tgtatcaggt gggccgcgtg     240
gaatttaccg cgcatggcga aagcgtgaac ggcccgaaca ccagcgatgt gtataccgaa     300
ccgattgcgt attttgtgct gaaaaccaaa aaaaaaggca aactgtatgc gctgagctat     360
tgcaacattc atggcctgtg gaaaaacgaa gtgaccctgg aa                         402

<210> SEQ ID NO 32
<211> LENGTH: 127
<212> TYPE: PRT
<213> ORGANISM: Artificial
<220> FEATURE:
<223> OTHER INFORMATION: Peroxisomal targeting SOR protein sequence

<400> SEQUENCE: 32

Met Ile Ser Glu Thr Ile Arg Ser Gly Asp Trp Lys Gly Glu Lys His
1               5                   10                  15

Val Pro Val Ile Glu Tyr Glu Arg Glu Gly Glu Leu Val Lys Val Lys
                20                  25                  30

Val Gln Val Gly Lys Glu Ile Pro His Pro Asn Thr Thr Glu His His
        35                  40                  45

Ile Arg Tyr Ile Glu Leu Tyr Phe Leu Pro Glu Gly Glu Asn Phe Val
    50                  55                  60

Tyr Gln Val Gly Arg Val Glu Phe Thr Ala His Gly Glu Ser Val Asn
65                  70                  75                  80

Gly Pro Asn Thr Ser Asp Val Tyr Thr Glu Pro Ile Ala Tyr Phe Val
                85                  90                  95

Leu Lys Thr Lys Lys Lys Gly Lys Leu Tyr Ala Leu Ser Tyr Cys Asn
                100                 105                 110

Ile His Gly Leu Trp Glu Asn Glu Val Thr Leu Glu Ser Lys Leu
        115                 120                 125

<210> SEQ ID NO 33
<211> LENGTH: 381
<212> TYPE: DNA
<213> ORGANISM: Artificial
<220> FEATURE:
<223> OTHER INFORMATION: Peroxisomal targeting SOR coding sequence

<400> SEQUENCE: 33
```

```
atgattagcg aaaccattcg cagcggcgat tggaaaggcg aaaaacatgt gccggtgatt    60
gaatatgaac gcgaaggcga actggtgaaa gtgaaagtgc aggtgggcaa agaaattccg   120
catccgaaca ccaccgaaca tcatattcgc tatattgaac tgtattttct gccggaaggc   180
gaaaactttg tgtatcaggt gggccgcgtg aatttaccg cgcatggcga aagcgtgaac    240
ggcccgaaca ccagcgatgt gtataccgaa ccgattgcgt attttgtgct gaaaaccaaa   300
aaaaaaggca aactgtatgc gctgagctat tgcaacattc atggcctgtg gaaaacgaa    360 gtgaccctgg aaagcaaact g                                             381
```

<210> SEQ ID NO 34
<211> LENGTH: 4
<212> TYPE: PRT
<213> ORGANISM: Artificial
<220> FEATURE:
<223> OTHER INFORMATION: Cytosolic membrane targeting sequence

<400> SEQUENCE: 34

Cys Val Val Gln
1

<210> SEQ ID NO 35
<211> LENGTH: 12
<212> TYPE: DNA
<213> ORGANISM: Artificial
<220> FEATURE:
<223> OTHER INFORMATION: Cytosolic membrane targeting coding sequence

<400> SEQUENCE: 35
tgtgtcgtgc ag                                                        12

<210> SEQ ID NO 36
<211> LENGTH: 128
<212> TYPE: PRT
<213> ORGANISM: Artificial
<220> FEATURE:
<223> OTHER INFORMATION: Cytosolic membrane targeting SOR protein
      sequence

<400> SEQUENCE: 36

Met Ile Ser Glu Thr Ile Arg Ser Gly Asp Trp Lys Gly Glu Lys His
1               5                   10                  15

Val Pro Val Ile Glu Tyr Glu Arg Glu Gly Glu Leu Val Lys Val Lys
            20                  25                  30

Val Gln Val Gly Lys Glu Ile Pro His Pro Asn Thr Thr Glu His His
        35                  40                  45

Ile Arg Tyr Ile Glu Leu Tyr Phe Leu Pro Glu Gly Glu Asn Phe Val
    50                  55                  60

Tyr Gln Val Gly Arg Val Glu Phe Thr Ala His Gly Glu Ser Val Asn
65                  70                  75                  80

Gly Pro Asn Thr Ser Asp Val Tyr Thr Glu Pro Ile Ala Tyr Phe Val
                85                  90                  95

Leu Lys Thr Lys Lys Lys Gly Lys Leu Tyr Ala Leu Ser Asp Cys Asn
            100                 105                 110

Ile His Gly Leu Trp Glu Asn Glu Val Thr Leu Glu Cys Val Val Gln
        115                 120                 125

<210> SEQ ID NO 37
<211> LENGTH: 384
<212> TYPE: DNA
<213> ORGANISM: Artificial

<220> FEATURE:
<223> OTHER INFORMATION: Cytosolic membrane SOR coding sequence

<400> SEQUENCE: 37

```
atgattagtg aaaccataag aagtggggac tggaaaggag aaaagcacgt ccccgttata    60
gagtatgaaa gagaagggga gcttgttaaa gttaaggtgc aggttggtaa agaaatcccg   120
catccaaaca ccactgagca ccacatcaga tacatagagc tttatttctt accagaaggt   180
gagaactttg tttaccaggt tggaagagtt gagtttacag ctcacggaga gtctgtaaac   240
ggcccaaaca cgagtgatgt gtacacagaa cccatagctt actttgtgct caagactaag   300
aagaagggca agctctatgc tcttagcgac tgtaacatcc acggcctttg ggaaaacgaa   360
gtcactttag agtgtgtcgt gcag                                          384
```

<210> SEQ ID NO 38
<211> LENGTH: 209
<212> TYPE: PRT
<213> ORGANISM: Artificial
<220> FEATURE:
<223> OTHER INFORMATION: Mitochondrial and chloroplast targeting SOR
      protein sequence

<400> SEQUENCE: 38

```
Met Leu Arg Thr Val Ser Cys Leu Ala Ser Arg Ser Ser Ser Ser Leu
1               5                   10                  15

Phe Phe Arg Phe Phe Arg Gln Phe Pro Arg Ser Tyr Met Ser Leu Thr
            20                  25                  30

Ser Ser Thr Ala Ala Leu Arg Val Pro Ser Arg Asn Leu Arg Arg Ile
        35                  40                  45

Ser Ser Pro Ser Val Ala Gly Arg Arg Leu Leu Leu Arg Arg Gly Leu
    50                  55                  60

Arg Ile Pro Ser Ala Ala Val Arg Ser Val Asn Gly Gln Phe Ser Arg
65                  70                  75                  80

Leu Ser Val Arg Ala Met Ile Ser Glu Thr Ile Arg Ser Gly Asp Trp
                85                  90                  95

Lys Gly Glu Lys His Val Pro Val Ile Glu Tyr Glu Arg Glu Gly Glu
            100                 105                 110

Leu Val Lys Val Lys Val Gln Val Gly Lys Glu Ile Pro His Pro Asn
        115                 120                 125

Thr Thr Glu His His Ile Arg Tyr Ile Glu Leu Tyr Phe Leu Pro Glu
    130                 135                 140

Gly Glu Asn Phe Val Tyr Gln Val Gly Arg Val Glu Phe Thr Ala His
145                 150                 155                 160

Gly Glu Ser Val Asn Gly Pro Asn Thr Ser Asp Val Tyr Thr Glu Pro
                165                 170                 175

Ile Ala Tyr Phe Val Leu Lys Thr Lys Lys Lys Gly Lys Leu Tyr Ala
            180                 185                 190

Leu Ser Tyr Cys Asn Ile His Gly Leu Trp Glu Asn Glu Val Thr Leu
        195                 200                 205

Glu
```

<210> SEQ ID NO 39
<211> LENGTH: 627
<212> TYPE: DNA
<213> ORGANISM: Artificial
<220> FEATURE:
<223> OTHER INFORMATION: Mitochondrial and chloroplast targeting SOR
      coding sequence

<400> SEQUENCE: 39

```
atgctgcgca ccgtgagctg cctggcgagc cgcagcagca gcagcctgtt ttttcgcttt      60
tttcgccagt ttccgcgcag ctatatgagc ctgaccagca gcaccgcggc gctgcgcgtg    120
ccgagccgca acctgcgccg cattagcagc ccgagcgtgg cgggccgccg cctgctgctg    180
cgccgcggcc tgcgcattcc gagcgcggcg gtgcgcagcg tgaacggcca gtttagccgc    240
ctgagcgtgc gcgcgatgat tagcgaaacc attcgcagcg gcgattggaa aggcgaaaaa    300
catgtgccgg tgattgaata tgaacgcgaa ggcgaactgg tgaaagtgaa agtgcaggtg    360
ggcaaagaaa ttccgcatcc gaacaccacc gaacatcata ttcgctatat tgaactgtat    420
tttctgccgg aaggcgaaaa ctttgtgtat caggtgggcc gcgtggaatt taccgcgcat    480
ggcgaaagcg tgaacggccc gaacaccagc gatgtgtata ccgaaccgat tgcgtatttt    540
gtgctgaaaa ccaaaaaaaa aggcaaactg tatgcgctga gctattgcaa cattcatggc    600
ctgtgggaaa acgaagtgac cctggaa                                        627
```

<210> SEQ ID NO 40
<211> LENGTH: 19
<212> TYPE: PRT
<213> ORGANISM: Saccharomyces cerevisiae

<400> SEQUENCE: 40

```
Met Leu Ser Ala Arg Ser Ala Ile Lys Arg Pro Ile Val Arg Gly Leu
1               5                   10                  15
Ala Thr Val
```

<210> SEQ ID NO 41
<211> LENGTH: 35
<212> TYPE: PRT
<213> ORGANISM: Chlamydomonas reinhardtii

<400> SEQUENCE: 41

```
Met Ala Leu Val Ala Arg Pro Val Leu Ser Ala Arg Val Ala Ala Ser
1               5                   10                  15
Arg Pro Arg Val Ala Ala Arg Lys Ala Val Arg Val Ser Ala Lys Tyr
            20                  25                  30
Gly Glu Asn
        35
```

<210> SEQ ID NO 42
<211> LENGTH: 29
<212> TYPE: PRT
<213> ORGANISM: Chlamydomonas reinhardtii

<400> SEQUENCE: 42

```
Met Gln Ala Leu Ser Ser Arg Val Asn Ile Ala Ala Lys Pro Gln Arg
1               5                   10                  15
Ala Gln Arg Leu Val Val Arg Ala Glu Glu Val Lys Ala
            20                  25
```

<210> SEQ ID NO 43
<211> LENGTH: 35
<212> TYPE: PRT
<213> ORGANISM: Chlamydomonas reinhardtii

<400> SEQUENCE: 43

```
Met Gln Thr Leu Ala Ser Arg Pro Ser Leu Arg Ala Ser Ala Arg Val
1               5                   10                  15
```

Ala Pro Arg Arg Ala Pro Arg Val Ala Val Val Thr Lys Ala Ala Leu
                20                  25                  30

Asp Pro Gln
        35

<210> SEQ ID NO 44
<211> LENGTH: 31
<212> TYPE: PRT
<213> ORGANISM: Chlamydomonas reinhardtii

<400> SEQUENCE: 44

Met Gln Ala Leu Ala Thr Arg Pro Ser Ala Ile Arg Pro Thr Lys Ala
1               5                   10                  15

Ala Arg Arg Ser Ser Val Val Val Arg Ala Asp Gly Phe Ile Gly
                20                  25                  30

<210> SEQ ID NO 45
<211> LENGTH: 51
<212> TYPE: PRT
<213> ORGANISM: Chlamydomonas reinhardtii

<400> SEQUENCE: 45

Met Ala Phe Ala Leu Ala Ser Arg Lys Ala Leu Gln Val Thr Cys Lys
1               5                   10                  15

Ala Thr Gly Lys Lys Thr Ala Lys Ala Ala Ala Pro Lys Ser Ser
                20                  25                  30

Gly Val Glu Phe Tyr Gly Pro Asn Arg Ala Lys Trp Leu Gly Pro Tyr
            35                  40                  45

Ser Glu Asn
    50

<210> SEQ ID NO 46
<211> LENGTH: 50
<212> TYPE: PRT
<213> ORGANISM: Chlamydomonas reinhardtii

<400> SEQUENCE: 46

Met Ala Ala Val Ile Ala Lys Ser Ser Val Ser Ala Val Ala Arg
1               5                   10                  15

Pro Ala Arg Ser Ser Val Arg Pro Met Ala Ala Leu Lys Pro Ala Val
                20                  25                  30

Lys Ala Ala Pro Val Ala Ala Pro Ala Gln Ala Asn Gln Met Met Val
            35                  40                  45

Trp Thr
    50

<210> SEQ ID NO 47
<211> LENGTH: 40
<212> TYPE: PRT
<213> ORGANISM: Chlamydomonas reinhardtii

<400> SEQUENCE: 47

Met Ala Ala Met Leu Ala Ser Lys Gln Gly Ala Phe Met Gly Arg Ser
1               5                   10                  15

Ser Phe Ala Pro Ala Pro Lys Gly Val Ala Ser Arg Gly Ser Leu Gln
                20                  25                  30

Val Val Ala Gly Leu Lys Glu Val
            35                  40

-continued

```
<210> SEQ ID NO 48
<211> LENGTH: 21
<212> TYPE: PRT
<213> ORGANISM: Escherichia coli

<400> SEQUENCE: 48

Met Lys Gln Ser Thr Ile Ala Lys Ala Lys Lys Pro Leu Leu Phe Thr
1               5                   10                  15

Pro Val Thr Lys Ala
            20

<210> SEQ ID NO 49
<211> LENGTH: 9
<212> TYPE: PRT
<213> ORGANISM: Artificial
<220> FEATURE:
<223> OTHER INFORMATION: Exemplary peroxisomal targeting sequence

<400> SEQUENCE: 49

Arg Leu Ala Val Ala Val Ala His Leu
1               5

<210> SEQ ID NO 50
<211> LENGTH: 516
<212> TYPE: DNA
<213> ORGANISM: Pyrococcus furiosus

<400> SEQUENCE: 50
atggtcgtga aagaacaat gactaaaaag ttcttggaag aagcctttgc aggcgaaagc      60
atggcccata tgaggtattt gatctttgcc gagaaagctg aacaagaagg atttccaaac    120
atagccaagc tgttcagggc aatagcttac gcagagtttg ttcacgctaa aaaccacttc    180
atagctctag gaaaattagg caaaactcca gaaaacttac agatgggaat agagggagaa    240
acgttcgaag ttgaggaaat gtacccagta tacaacaaag ccgcagaatt ccaaggagaa    300
aaggaagcag ttagaacaac ccactatgct ttagaggcgg agaagatcca cgctgaactc    360
tatagaaagg caaagagaaa agctgagaaa ggggaagaca ttgaaataaa gaaagtttac    420
atatgcccaa tctgtggata caccgctgtt gatgaggctc cagaatactg tccagtttgt    480
ggagctccaa aagaaaagtt cgttgtcttt gaatga                              516

<210> SEQ ID NO 51
<211> LENGTH: 171
<212> TYPE: PRT
<213> ORGANISM: Pyrococcus furiosus

<400> SEQUENCE: 51

Met Val Val Lys Arg Thr Met Thr Lys Lys Phe Leu Glu Glu Ala Phe
1               5                   10                  15

Ala Gly Glu Ser Met Ala His Met Arg Tyr Leu Ile Phe Ala Glu Lys
                20                  25                  30

Ala Glu Gln Glu Gly Phe Pro Asn Ile Ala Lys Leu Phe Arg Ala Ile
            35                  40                  45

Ala Tyr Ala Glu Phe Val His Ala Lys Asn His Phe Ile Ala Leu Gly
        50                  55                  60

Lys Leu Gly Lys Thr Pro Glu Asn Leu Gln Met Gly Ile Glu Gly Glu
65                  70                  75                  80

Thr Phe Glu Val Glu Glu Met Tyr Pro Val Tyr Asn Lys Ala Ala Glu
                85                  90                  95

Phe Gln Gly Glu Lys Glu Ala Val Arg Thr Thr His Tyr Ala Leu Glu
```

```
                100             105             110
Ala Glu Lys Ile His Ala Glu Leu Tyr Arg Lys Ala Lys Glu Lys Ala
            115                 120                 125

Glu Lys Gly Glu Asp Ile Glu Ile Lys Lys Val Tyr Ile Cys Pro Ile
        130                 135                 140

Cys Gly Tyr Thr Ala Val Asp Glu Ala Pro Glu Tyr Cys Pro Val Cys
145                 150                 155                 160

Gly Ala Pro Lys Glu Lys Phe Val Val Phe Glu
                165                 170

<210> SEQ ID NO 52
<211> LENGTH: 58
<212> TYPE: DNA
<213> ORGANISM: Escherichia coli

<400> SEQUENCE: 52
atgaaacaga gcaccattgc gaaagcgaaa aaccgctgc tgtttacccc ggtgacca          58

<210> SEQ ID NO 53
<211> LENGTH: 24
<212> TYPE: DNA
<213> ORGANISM: Artificial
<220> FEATURE:
<223> OTHER INFORMATION: PCR primer

<400> SEQUENCE: 53
caccatgatt agtgaaacca taag                                              24

<210> SEQ ID NO 54
<211> LENGTH: 20
<212> TYPE: DNA
<213> ORGANISM: Artificial
<220> FEATURE:
<223> OTHER INFORMATION: PCR primer

<400> SEQUENCE: 54
atgattagtg aaaccataag                                                   20

<210> SEQ ID NO 55
<211> LENGTH: 24
<212> TYPE: DNA
<213> ORGANISM: Artificial
<220> FEATURE:
<223> OTHER INFORMATION: PCR primer

<400> SEQUENCE: 55
tcactctaaa gtgacttcgt tttc                                              24

<210> SEQ ID NO 56
<211> LENGTH: 22
<212> TYPE: DNA
<213> ORGANISM: Artificial
<220> FEATURE:
<223> OTHER INFORMATION: PCR primer

<400> SEQUENCE: 56
aacacaaacc acaagaggat ca                                                22

<210> SEQ ID NO 57
<211> LENGTH: 20
<212> TYPE: DNA
<213> ORGANISM: Artificial
<220> FEATURE:
<223> OTHER INFORMATION: PCR primer
```

<400> SEQUENCE: 57
cgtcaacgtt ttcttgtcca                                             20

<210> SEQ ID NO 58
<211> LENGTH: 861
<212> TYPE: DNA
<213> ORGANISM: Camelina sativa

<400> SEQUENCE: 58
atggcagaaa acaaagaaga agatgttaag cttggagcta acaaattcag agaaacacag    60
ccattaggaa cagctgctca aacagacaaa gattacaaag aaccaccacc agctcctttg   120
tttgaaccag gggaattatc atcatggtca ttttacagag ctggaattgc agaatttatg   180
gctactttct tgttttttgta catcactatc ttgactgtta tgggtcttaa agatctgat   240
agtctgtgta gttcagttgg tattcaaggt gttgcttggg cttttggtgg tatgatcttt   300
gctttggttt actgtactgc tggtatctca ggaggacaca tcaacccagc tgtgaccttt   360
ggattgttct tggcaaggaa actgtcctta accagggcta ttttctacat agtgatgcaa   420
tgccttggtg caatttgtgg tgctggtgtt gtgaagggat tcatggttgg tccataccag   480
agacttggtg gtggtgctaa tgttgttaac catggttaca ccaaaggtga tggccttggt   540
gctgaaatta ttggcacttt tgtccttgtt tacactgttt tctctgctac tgatgctaag   600
agaaatgcca gagactcaca tgttcctatt ttggcaccac ttcccatcgg attcgcggtt   660
ttcttggttc atttggccac cattccatc accggaactg catcaaccc cgctaggagt   720
cttggagctg cgatcatcta aacacagac caggcatggg acgaccactg gatcttttgg   780
gttggaccat tcattggagc tgcacttgct gcagtttacc atcaaataat catcagagcc   840
attccattcc acaagtcgtc t                                           861

<210> SEQ ID NO 59
<211> LENGTH: 287
<212> TYPE: PRT
<213> ORGANISM: Camelina sativa

<400> SEQUENCE: 59

Met Ala Glu Asn Lys Glu Glu Asp Val Lys Leu Gly Ala Asn Lys Phe
1               5                   10                  15

Arg Glu Thr Gln Pro Leu Gly Thr Ala Ala Gln Thr Asp Lys Asp Tyr
            20                  25                  30

Lys Glu Pro Pro Pro Ala Pro Leu Phe Glu Pro Gly Glu Leu Ser Ser
        35                  40                  45

Trp Ser Phe Tyr Arg Ala Gly Ile Ala Glu Phe Met Ala Thr Phe Leu
    50                  55                  60

Phe Leu Tyr Ile Thr Ile Leu Thr Val Met Gly Leu Lys Arg Ser Asp
65                  70                  75                  80

Ser Leu Cys Ser Ser Val Gly Ile Gln Gly Val Ala Trp Ala Phe Gly
                85                  90                  95

Gly Met Ile Phe Ala Leu Val Tyr Cys Thr Ala Gly Ile Ser Gly Gly
            100                 105                 110

His Ile Asn Pro Ala Val Thr Phe Gly Leu Phe Leu Ala Arg Lys Leu
        115                 120                 125

Ser Leu Thr Arg Ala Ile Phe Tyr Ile Val Met Gln Cys Leu Gly Ala
    130                 135                 140

Ile Cys Gly Ala Gly Val Val Lys Gly Phe Met Val Gly Pro Tyr Gln

```
                145                 150                 155                 160
Arg Leu Gly Gly Gly Ala Asn Val Val Asn His Gly Tyr Thr Lys Gly
                    165                 170                 175

Asp Gly Leu Gly Ala Glu Ile Ile Gly Thr Phe Val Leu Val Tyr Thr
                180                 185                 190

Val Phe Ser Ala Thr Asp Ala Lys Arg Asn Ala Arg Asp Ser His Val
            195                 200                 205

Pro Ile Leu Ala Pro Leu Pro Ile Gly Phe Ala Val Phe Leu Val His
        210                 215                 220

Leu Ala Thr Ile Pro Ile Thr Gly Thr Gly Ile Asn Pro Ala Arg Ser
225                 230                 235                 240

Leu Gly Ala Ala Ile Ile Tyr Asn Thr Asp Gln Ala Trp Asp Asp His
                245                 250                 255

Trp Ile Phe Trp Val Gly Pro Phe Ile Gly Ala Ala Leu Ala Ala Val
                260                 265                 270

Tyr His Gln Ile Ile Ile Arg Ala Ile Pro Phe His Lys Ser Ser
                275                 280                 285
```

<210> SEQ ID NO 60
<211> LENGTH: 2496
<212> TYPE: DNA
<213> ORGANISM: Synechococcus sp. PCC 7002

<400> SEQUENCE: 60

```
ccgtaagcat caacgattct ttacatcatc atccatcggc gcgacttgct cacatcgcag     60
cattaagatt gcagttgcca tagccacaat cccagaaaaa attcacgatc cagtacccga    120
aagcctttt ttaaaccaat tttagataag tttagttat tttttatcc aaaaagactt       180
aagtccagct tatttacatg tcatggcctt aggactatat aaatctcac atccatagtc     240
gaaagactat caacaggcca agtttaaggg caatgtcctt gaggattctg ccctttctct    300
cagttttca tcattgattc ttcgatcaat tgagtacagc acctagttaa agcaaacaca     360
aatatatgaa tcaatacagt catcgtaaat ttttgatcac cactggcgtg gcagcgggca    420
gcttatccat attttctttg tagtaattag agttttagca cagaaacaat tggaactttc    480
ttgggcattt taaacaattt tatatttatc gaggaggaat ctactgttat gagacaacag    540
caactttttt ggctgactac tttgatcgtt ggggggcaata ttttttcaggc tgctacgcca   600
ctacaggccc aggaaattaa tttgacaaca tcgctgagtt caccaacact acaggattct    660
cgctatctag cctcggcctc catgggacaa atggcctcag tatctagatt acggacgtg     720
aagccgacgg attgggctta tgaagcacta caaagtctgg tggaacggta tggttgcatt    780
gttggttatc cagatcaaac attccgcggc gatcgccccc tgagccgtta tgaatttgcc    840
gccggactaa atgcttgcct caatgcccta gaacggcaga tccaaggcaa taatgccgat    900
gtatcctcca gcgatcttgc aaccctccgg cgattgacca acgagtttca ggcggaatta    960
gccacccctcg gcacaagggt tgatgatctc gaagcccgca ccagtgaact cgaaaaccaa   1020
caatttttcaa cgaccacaaa actgaatgga gaagctattt tctctatcag tggggcaacg  1080
ggtggtgaac cagagggcaa cgatgctcag attaccttca ataatcgtct gcggctgaat   1140
ttgaccacca gttttaccgg aaaagatgcc ctgattactg gcttacaagc ctacaatttt   1200
tcggcgggta atctattac aggtacaggt aacgttgccg aaactctctt tcccaatgat   1260
gcctctatcc ttggggatag catgactaac ctcgcctggg aaccaacaatt tgctggtttg  1320
aatccacaaa atctacaacc tagttgcggt aacaatagcc tttgtctgta caagttgctc   1380
```

-continued

```
tatgttagac cgatcacaga taaattaacg gcatttattg gcccgaaggc ggaagttacc    1440
gatgcctttc cggcgattct tcccttttgct agtgaaggcc agggagcact ttctcgcttt    1500
gcaactttga atccagtatt gcggatgtct gggggaacca gtggtacagg actcgcttcc    1560
gcagctggct ttatctataa acccaatgat gtcatcgatt gcgggcact ctatgggtca      1620 gtgaatgcgg caatccctgg taatgaaggt tttccgggga cgccgttggg ggctggcttg     1680
ttcaatggca gttttatcgc cgcaacacaa ttgacgcttc atcctaatga caagcttgat     1740
ctaggtctga actatgccta cagctaccac cagatcaata ttgcgggtac gggtttaaca    1800
ggagctgaga cgcgtattct tggcgatcta ccactgacca ccccagtacg atttaactcc    1860
tttggggcaa cagtaaactg gcgcgtcagt ccaaaagtta acctgacagg ttatggggca    1920
tacatcatga cagatcaagc gaatagtggc tctgcctata caaatctaag cagttggatg    1980
gcgggtctgt attttccaga tgcattcgcg aagggcaatg cggcagggat tttgtttggt    2040
caaccacttt atcgggtaga tgcgggtaat ggggcgagtt taagtccagc aaacattggc    2100
gatcgccaaa ccccctacca actggaagcc ttttatcgcc atcaaatcaa tgatcacatc     2160
agcattacgc cggggggcatt tgtgattttc aatccagaag gagatgccca aaatgaaaca    2220
accagcgttt ttgcgttgcg tacgacttat accttctaga actaactgat caccattta     2280 cttagtagaa acttatgagt gttttttgttg cggctgatag tattgataaa gtatttccgt   2340 tgtcggggt ggtgaatata ttacccttta atattttta ccttcataaa tcatgttcaa      2400
aactttaatc aaaaatagtg cggcgatcgc gtttgtactt ttaggttcca tagccgttat   2460
tcctggggca agttcccaaa ttagtgctac tccctt                              2496
```

<210> SEQ ID NO 61
<211> LENGTH: 576
<212> TYPE: PRT
<213> ORGANISM: Synechococcus sp. PCC 7002

<400> SEQUENCE: 61

```
Met Arg Gln Gln Gln Leu Phe Trp Leu Thr Thr Leu Ile Val Gly Gly
1               5                   10                  15

Asn Ile Phe Gln Ala Ala Thr Pro Leu Gln Ala Gln Glu Ile Asn Leu
            20                  25                  30

Thr Thr Ser Leu Ser Ser Pro Thr Leu Gln Asp Ser Arg Tyr Leu Ala
        35                  40                  45

Ser Ala Ser Met Gly Gln Met Ala Ser Val Ser Arg Leu Arg Asp Val
    50                  55                  60

Lys Pro Thr Asp Trp Ala Tyr Glu Ala Leu Gln Ser Leu Val Glu Arg
65                  70                  75                  80

Tyr Gly Cys Ile Val Gly Tyr Pro Asp Gln Thr Phe Arg Gly Asp Arg
                85                  90                  95

Pro Leu Ser Arg Tyr Glu Phe Ala Ala Gly Leu Asn Ala Cys Leu Asn
            100                 105                 110

Ala Leu Glu Arg Gln Ile Gln Gly Asn Asn Ala Asp Val Ser Ser Ser
        115                 120                 125

Asp Leu Ala Thr Leu Arg Arg Leu Thr Asn Glu Phe Gln Ala Glu Leu
    130                 135                 140

Ala Thr Leu Gly Thr Arg Val Asp Asp Leu Glu Ala Arg Thr Ser Glu
145                 150                 155                 160

Leu Glu Asn Gln Gln Phe Ser Thr Thr Lys Leu Asn Gly Glu Ala
                165                 170                 175
```

```
Ile Phe Ser Ile Ser Gly Ala Thr Gly Gly Glu Pro Glu Gly Asn Asp
                180                 185                 190

Ala Gln Ile Thr Phe Asn Asn Arg Leu Arg Leu Asn Leu Thr Thr Ser
            195                 200                 205

Phe Thr Gly Lys Asp Ala Leu Ile Thr Gly Leu Gln Ala Tyr Asn Phe
        210                 215                 220

Ser Ala Gly Lys Ser Ile Thr Gly Thr Gly Asn Val Ala Glu Thr Leu
225                 230                 235                 240

Phe Pro Asn Asp Ala Ser Ile Leu Gly Asp Ser Met Thr Asn Leu Ala
                245                 250                 255

Trp Glu Pro Gln Phe Ala Gly Leu Asn Pro Gln Asn Leu Gln Pro Ser
            260                 265                 270

Cys Gly Asn Asn Ser Leu Cys Leu Tyr Lys Leu Leu Tyr Val Arg Pro
        275                 280                 285

Ile Thr Asp Lys Leu Thr Ala Phe Ile Gly Pro Lys Ala Glu Val Thr
        290                 295                 300

Asp Ala Phe Pro Ala Ile Leu Pro Phe Ala Ser Glu Gly Gln Gly Ala
305                 310                 315                 320

Leu Ser Arg Phe Ala Thr Leu Asn Pro Val Leu Arg Met Ser Gly Gly
                325                 330                 335

Thr Ser Gly Thr Gly Leu Ala Ser Ala Ala Gly Phe Ile Tyr Lys Pro
            340                 345                 350

Asn Asp Val Ile Asp Trp Arg Ala Leu Tyr Gly Ser Val Asn Ala Ala
        355                 360                 365

Ile Pro Gly Asn Glu Gly Phe Pro Gly Thr Pro Leu Gly Ala Gly Leu
        370                 375                 380

Phe Asn Gly Ser Phe Ile Ala Ala Thr Gln Leu Thr Leu His Pro Asn
385                 390                 395                 400

Asp Lys Leu Asp Leu Gly Leu Asn Tyr Ala Tyr Ser Tyr His Gln Ile
                405                 410                 415

Asn Ile Ala Gly Thr Gly Leu Thr Gly Ala Glu Thr Arg Ile Leu Gly
            420                 425                 430

Asp Leu Pro Leu Thr Thr Pro Val Arg Phe Asn Ser Phe Gly Ala Thr
        435                 440                 445

Val Asn Trp Arg Val Ser Pro Lys Val Asn Leu Thr Gly Tyr Gly Ala
        450                 455                 460

Tyr Ile Met Thr Asp Gln Ala Asn Ser Gly Ser Ala Tyr Thr Asn Leu
465                 470                 475                 480

Ser Ser Trp Met Ala Gly Leu Tyr Phe Pro Asp Ala Phe Ala Lys Gly
                485                 490                 495

Asn Ala Ala Gly Ile Leu Phe Gly Gln Pro Leu Tyr Arg Val Asp Ala
            500                 505                 510

Gly Asn Gly Ala Ser Leu Ser Pro Ala Asn Ile Gly Asp Arg Gln Thr
        515                 520                 525

Pro Tyr Gln Leu Glu Ala Phe Tyr Arg His Gln Ile Asn Asp His Ile
        530                 535                 540

Ser Ile Thr Pro Gly Ala Phe Val Ile Phe Asn Pro Glu Gly Asp Ala
545                 550                 555                 560

Gln Asn Glu Thr Thr Ser Val Phe Ala Leu Arg Thr Tyr Thr Phe
                565                 570                 575

<210> SEQ ID NO 62
<211> LENGTH: 948
```

```
<212> TYPE: DNA
<213> ORGANISM: Thioalkalivibrio sp. K90mix

<400> SEQUENCE: 62
atggcttttg atccggtagt tctgttcttc ctgctcgggg cgattgccgg gctggccaag      60
tcggacctca agatcccgat ggcgatctac gaggcactgt cgatttacct cctgctggcc     120
atcggcttgc atggtggcgt gaagctggcg aaagcgagc tggtgccgct catcctgcct      180
ggccttgcgg tgctgatggt cggggccctg atcccgctgc tggcgttccc ggtgctgcgc     240
tggctggggc atatgccgcg cgcggattcg gcctccatcg ccgcgcacta cgggtcggtc     300
agtgtggtga cgttctcggt ggcggtggcc tttctcgcgg cccgagggat cgactacgag     360
ggccacatgg tggtcttcct ggtgctgctg agatgccgg cactggtgat cggcatcctg      420
ctggcgcgca tggcacgaa gggaccggtg caatggggca agaccatgca cgaggtcttt      480
ttcggcaaga gcatcttcct gctcgccggt gggctggtga tcggattcgt ggccggtccc     540
gaactgatgg acccactgga gccgatgttc ttcgatctgt tcaagggcgt gctggccctg     600
ttcctgctgg agatggggct ggtcgcctcg agccggatcg ccgaggtgcg ccagtacggg     660
ctgttcctgg tagtgttcgc gatcgtgatg ccggtggtct cggcgatcct cgggatcctg     720
ctgggctggg gcctgggcat gagcctgggc ggtacgctgc tgctggctac cctgtacgcg     780
agtgcgtcct acatcgccgc acccgcggcc atgcggatcg cggtccccaa ggccaacccc     840
gcgctgtcga tcggggcctc gctgggggtt accttcccgt tcaatattt cctgggcgtc      900
ccgctgtatt tctggatgac ccagtggctc tactcgttgg gaggctag                  948

<210> SEQ ID NO 63
<211> LENGTH: 315
<212> TYPE: PRT
<213> ORGANISM: Thioalkalivibrio sp. K90mix

<400> SEQUENCE: 63

Met Ala Phe Asp Pro Val Val Leu Phe Phe Leu Leu Gly Ala Ile Ala
1               5                   10                  15

Gly Leu Ala Lys Ser Asp Leu Lys Ile Pro Met Ala Ile Tyr Glu Ala
            20                  25                  30

Leu Ser Ile Tyr Leu Leu Leu Ala Ile Gly Leu His Gly Gly Val Lys
        35                  40                  45

Leu Ala Glu Ser Glu Leu Val Pro Leu Ile Leu Pro Gly Leu Ala Val
    50                  55                  60

Leu Met Val Gly Ala Leu Ile Pro Leu Leu Ala Phe Pro Val Leu Arg
65                  70                  75                  80

Trp Leu Gly His Met Pro Arg Ala Asp Ser Ala Ser Ile Ala Ala His
                85                  90                  95

Tyr Gly Ser Val Ser Val Val Thr Phe Ser Val Ala Val Ala Phe Leu
            100                 105                 110

Ala Ala Arg Gly Ile Asp Tyr Glu Gly His Met Val Val Phe Leu Val
        115                 120                 125

Leu Leu Glu Met Pro Ala Leu Val Ile Gly Ile Leu Leu Ala Arg Met
    130                 135                 140

Gly Thr Lys Gly Pro Val Gln Trp Gly Lys Thr Met His Glu Val Phe
145                 150                 155                 160

Phe Gly Lys Ser Ile Phe Leu Leu Ala Gly Gly Leu Val Ile Gly Phe
                165                 170                 175

Val Ala Gly Pro Glu Leu Met Asp Pro Leu Glu Pro Met Phe Phe Asp
```

-continued

```
             180                 185                 190
Leu Phe Lys Gly Val Leu Ala Leu Phe Leu Leu Glu Met Gly Leu Val
        195                 200                 205

Ala Ser Ser Arg Ile Ala Glu Val Arg Gln Tyr Gly Leu Phe Leu Val
        210                 215                 220

Val Phe Ala Ile Val Met Pro Val Val Ser Ala Ile Leu Gly Ile Leu
225                 230                 235                 240

Leu Gly Trp Gly Leu Gly Met Ser Leu Gly Gly Thr Leu Leu Leu Ala
                245                 250                 255

Thr Leu Tyr Ala Ser Ala Ser Tyr Ile Ala Ala Pro Ala Ala Met Arg
                260                 265                 270

Ile Ala Val Pro Lys Ala Asn Pro Ala Leu Ser Ile Gly Ala Ser Leu
        275                 280                 285

Gly Val Thr Phe Pro Phe Asn Ile Phe Leu Gly Val Pro Leu Tyr Phe
        290                 295                 300

Trp Met Thr Gln Trp Leu Tyr Ser Leu Gly Gly
305                 310                 315
```